US008906386B2

(12) United States Patent
Rosa Calatrava et al.

(10) Patent No.: US 8,906,386 B2

(45) **Date of Patent: *Dec. 9, 2014**

(54) MUTANT PROTEINS OF THE F PROTEIN OF PIV-5 AND PIV-2

(75) Inventors: Manuel Melchior Jean-Pierre Rosa Calatrava, Lyons (FR); Olivier Terrier, Lyons (FR); Francois Edouard Julien Durupt, Lyons (FR)

(73) Assignees: Centre National de la Recherche Scientifique, Paris (FR); Universite Claude Bernard de Lyon 1, Villeurbanne (FR); Les Hospices Civils de Lyon, Lyon (FR)

(*) Notice: Subject to any disclaimer, the term of this patent is extended or adjusted under 35 U.S.C. 154(b) by 292 days.

This patent is subject to a terminal disclaimer.

(21) Appl. No.: 13/130,554

(22) PCT Filed: Nov. 17, 2009

(86) PCT No.: PCT/FR2009/001317

§ 371 (c)(1), (2), (4) Date: Sep. 9, 2011

(87) PCT Pub. No.: WO2010/058099

PCT Pub. Date: May 27, 2010

(65) Prior Publication Data

US 2011/0311541 A1 Dec. 22, 2011

(30) Foreign Application Priority Data

Nov. 21, 2008 (FR) .................................... 08 06548

(51) Int. Cl.

*A61K 39/155* (2006.01)
*A61K 39/12* (2006.01)
*C12N 5/071* (2010.01)
*C07K 14/005* (2006.01)

(52) U.S. Cl.

CPC ..... *C07K 14/005* (2013.01); *C12N 2760/18722* (2013.01); *C12N 2760/18022* (2013.01)

USPC ...................... 424/211.1; 424/186.1; 435/366

(58) Field of Classification Search

None

See application file for complete search history.

(56) References Cited

FOREIGN PATENT DOCUMENTS

WO WO-02/077211 10/2002

OTHER PUBLICATIONS

Paterson et al., PNAS USA, 1984, 81(21):6706-6710.*

Terrier, O. et al., “Engineering of a parainfluenza virus type 5 fusion protein (PIV-5 F): Development of an autonomous and hyperfusogenic protein by a combinational mutagenesis approach,” *Virus Research*, vol. 146, No. 1-2, Dec. 2009, pp. 115-124.

Russell, Charles J. et al., “A dual-functional paramyxovirus F protein regulatory switch segment: Activation and membrane fusion,” *Journal of Cell Biology*, vol. 163, No. 2, Oct. 27, 2003, pp. 363-374.

Kawano, M. et al., “Sequence of the fusion protein gene of human parainfluenza type 2 virus and its 3’ intergenic region: Lack of small hydrophobic (SH) gene,” *Virology*, Academic Press, Orlando, US, vol. 178, No. 1, Sep. 1, 1990, pp. 289-292.

Ito, Morihiro et al., “Role of a single amino acid at the amino terminus of the simian virus 5 F2 subunit in syncytium formation,” *Journal of Virology*, vol. 71, No. 12, Dec. 1997, pp. 9855-9858.

Ito, Morihiro et al., “An amino acid in the heptad repeat 1 domain is important for the haemagglutinin-neuraminidase-independent fusing activity of simian virus 5 fusion protein,” *Journal of General Virology*, vol. 81, 2000, pp. 719-727.

Paterson, Reay G. et al., “Fusion protein of the paramyxovirus SV5: Destabilizing and stabilizing mutants of fusion activation,” *Virology*, vol. 270, 2000, pp. 17-30.

Gardner, Amanda E. et al., “A conserved region between the heptad repeats of paramyxovirus fusion proteins is critical for proper F protein folding,” *Biochemistry*, vol. 46, No. 17, May 1, 2007, pp. 5094-5105.

Chatziandreou, N. et al., “Relationships and host range of human, canine simian and procine isolates of simian virus 5 (parainfluenza virus 5),” *Journal of General Virology*, vol. 85, 2004, pp. 3007-3016.

Dupressoir, et al, “Syncytin—A knockout mice demonstrate the critical role in placentation of a fusogenic, endogenous retrovirus-derived, envelope gene,” PNAS, Jul. 21, 2009, vol. 106, No. 29, pp. 12127-12132.

Gomez-Trevino, et al, “Effects of adenovirus-mediated SV5 fusogenic glycoprotein expression on tumor cells,” The Journal of Gene Medicine, 2003, 5: pp. 483-492.

Lambert, et al, “Peptides from conserved regions of paramyxovirus fusion (F) proteins are potent inhibitors of viral fusion,” Proc. Natl. Acad. Sci. USA, Mar. 1996, vol. 93, pp. 2186-2191.

Yao, et al, “Peptides Corresponding to the Heptad Repeat Sequence of Human Parainfluenza Virus Fusion Protein Are Potent Inhibitors of Virus Infection,” Virology 223, 1996, Article No. 0459, pp. 103-112.

* cited by examiner

*Primary Examiner* — Stacy B Chen

(74) *Attorney, Agent, or Firm* — Birch, Stewart, Kolasch & Birch, LLP

(57) ABSTRACT

The present application concerns mutant proteins of the fusion protein (F protein) of the parainfluenza virus (PIV) which are currently indexed as type 5 PIV (PIV-5 or PIV5) and type 2 PIV (PIV-2 or PIV2). The present application concerns products deriving therefrom, such as: nucleic acids, vectors, cells, fusion inhibitors of the antibody, aptamer, interfering RNA type; myelomas, hybridomas; stem and progenitor cells. The present application also concerns mutant proteins and products derived therefrom for use in medical and biotechnological applications.

23 Claims, 11 Drawing Sheets

>F PIV-5 WR strain (529aa)(GenBank AB021962)

MGTIIQFLVV SCLLAGAGSL DLAALMQIGV IPTNVRQLMY YTEASSAFIV VKLMPTIDSP 60

ISGCNITSIS SYNATVTKLL QPIGENLETI RNQLIPTRRR RRFAGVVIGL AALGVATAAQ 120

VTAAVALVKA NENAAAILNL KNAIQKTNAA VADVVQATQS LGTAVQAVQD HINSVVSPAI 180

TAANCKAQD AIIGSILNLYL TELTTIFHNQ ITNPALSPIT IQALRILLGS TLPTVVEKSF 240

NTQISAAELL SSGLLTGQIV GLDLTYMQMV IKIELPTLTV QPATQIIDLA TISAFINNQE 300

VMAQLPTRVM VTGSLIQAYP ASQCTITPNT VYCRYNDAQV LSDDTMACLQ GNLTRCTFSP 360

VVGSFLTRFV LFDGIVYANC RSMLCKCMQP AAVILQPSSS PVTVIDMYKC VSLQLDNLRF 420

TITQLANVTY NSTIKLESSQ ILPIDPLDIS QNLAAVNKSL SDALQHLAQS DTYLSAITSA 480

TTTSVLSIIA ICLGSLGLIL IILLSVVVWK LLTIVAANRN RMENFVYHK 529

SEQ ID NO: 31 (reference sequence for the F protein of PIV-5)

```
  30                                a tgggtactat tattcaattt ctggtggtct
  61 cctgtctatt ggcaggagca ggcagccttg atctagcagc cctcatgcaa atcggtgtca
 121 ttccaacaaa tgtccggcaa cttatgtatt atactgaggc ctcatcggca ttcattgttg
 181 tgaagttaat gcctacaatt gactcgccga ttagtggatg taatataaca tcaatttcaa
 241 gctataatgc aacagtgaca aaactcctac agccgatcgg tgagaatttg gagacgatta
 301 ggaaccagtt gattccaact cggagaagac gccggtttgc aggggtggtg attggattag
 361 ctgcattagg agtagctact gccgcacagg tcactgccgc agtagcacta gtaaaggcaa
 421 atgaaaatgc tgcggctata ctcaatctca aaaatgcaat ccaaaaaaca aatgcagcag
 481 ttgcagatgt ggtccaggcc acacaatcac taggaacggc agttcaagca gttcaagatc
 541 acataaacag tgtggtaagt ccagcaatta cagcagccaa ttgtaaggcc caagatgcta
 601 tcattggctc aatcctcaat ctctatttga ccgagttgac aaccatcttc cacaatcaaa
 661 ttacaaaccc tgcattgagt cccattacaa ttcaagcttt aaggatccta ctggggagta
 721 ccttgccgac tgtggtcgaa aaatctttca atacccagat aagtgcagct gagcttctct
 781 catcagggtt attgacaggc cagattgtgg gattagattt gacctatatg cagatggtca
 841 taaaaattga gctgccaact ttaactgtac aacctgcaac ccagatcata gatctggcca
 901 ccatttctgc attcattaac aatcaagaag tcatggccca attaccaaca cgtgttatgg
 961 tgactggcag cttgatccaa gcctatcccg catcgcaatg caccattaca cccaacactg
1021 tgtactgtag gtataatgat gcccaagtac tctcagatga tactatggct tgcctccaag
1081 gtaacttgac aagatgcacc ttctctccag tggttgggag ctttctcact cgattcgtgc
1141 tgttcgatgg aatagtttat gcaaattgca ggtcgatgtt gtgcaagtgc atgcaacctg
1201 ctgctgtgat cctacagccg agttcatccc ctgtaactgt cattgacatg tacaaatgtg
1261 tgagtctgca gcttgacaat ctcagattca ccatcactca attggccaat gtaacctaca
1321 atagcaccat caagcttgaa tcatcccaga tcttgcctat tgatccgttg gatatatccc
1381 agaatctagc tgcggtgaat aagagtctaa gtgatgcact acaacactta gcacaaagtg
1441 acacatatct ttctgcaatc acatcagcta cgactacaag tgtattatcc ataatagcaa
1501 tctgtcttgg atcgttaggt ttaatattaa taatcttgct cagtgtagtt gtgtggaagt
1561 tattgaccat tgtcgctgct aatcgaaata gaatggagaa ttttgtttat cataaataa
```

// SEQ ID NO: 30

(CDS sequence: nucleic acid sequence encoding the F protein of PIV-5 referenced as SEQ ID NO : 31)

Figure 1A

>F hPIV-2 Greer strain (551 aa)(Genbank complete genome NC 003443)

MHHLHPMIVC IFVMYTGIVG SDAIAGDQLL NIGVIQSKIR SLMYYTDGGA SFIVVKLLPN 60
LPPSNGTCNI TSLDAYNVTL FKLLTPLIEN LSKISTVTDT KTRQKRFAGV VVGLAALGVA 120
TAAQITAAVA IVKANANAAA INNLASSIQS TNKAVSDVID ASRTIATAVQ AIQDRINGAI 180
VNGITSASCR AHDALIGSIL NLYLTELTTI FHNQITNPAL TPLSIQALRI LLGSTLPIVI 240
ESKLNTNFNT AELLSSGLLT GQIISISPMY MQMLIQINVP TFIMQPGAKV IDLIAISANH 300
KLQEVVVQVP NRILEYANEL QNYPANDCVV TPNSVFCRYN EGSPIPESQY QCLRGNLNSC 360
TFTPIIGNFL KRFAFANGVL YANCKSLLCR CADPPHVVSQ DDTQGISIID IKRCSEMMLD 420
TFSFRITSTF NATYVTDFSM INANIVHLSP LDLSNQINSI NKSLKSAEDW IADSNFFANQ 480
ARTAKTLYSL SAIALILSVI TLVVVGLLIA YIIKLVSQIH QFRSLAATTM FHRENPAFFS 540
KNNHGNIYGI S 551

SEQ ID NO: 33 (reference sequence for F protein of PIV-2)

```
4789                                                     at gcatcacctg
4801 catccaatga tagtatgcat ctttgttatg tacactggaa ttgtaggttc agatgccatt
4861 gctggagatc aactacttaa tataggggtc attcaatcaa agataagatc actcatgtac
4921 tatactgatg gtggtgctag ctttattgtt gtaaaattgc tacctaatct tcccccaagc
4981 aatggaacat gcaacatcac cagtctagat gcatataatg ttaccctatt taagttacta
5041 acacccctga ttgagaacct gagtaaaatt tccactgtta cagataccaa aacccgccaa
5101 aaacgatttg caggagtagt tgttggactt gctgcattag gagtagccac agccgcacaa
5161 ataactgcag ctgtagcaat agtgaaagct aatgcaaatg ctgctgcgat aaacaatctt
5221 gcatcttcaa ttcaatccac caacaaggca gtatccgatg tgatagatgc atcaagaaca
5281 attgcaaccg cagttcaagc aattcaggat cgcatcaatg gagctattgt taatgggata
5341 acatctgcat catgccgtgc ccatgatgca ctcattgggt caatattaaa tctttatctc
5401 actgagctta ccacaatatt tcataatcaa ataacaaacc ctgcgctgac accactctcc
5461 atccaagctt taagaatcct cctcggtagc accttgccaa ttgtcattga gtccaaactc
5521 aacacaaact tcaacacagc agagctgctc agttccggac tgttaactgg tcaaataatt
5581 tccatttccc caatgtacat gcaaatgcta attcaaatca atgttccgac atttataatg
5641 caacccggtg cgaaggtaat tgatctaatt gctatctccg caaaccataa attgcaagaa
5701 gtggttgtac aagttccgaa taggattcta gagtatgcaa atgaactaca aaattaccca
5761 gccaatgact gtgtcgtgac accgaactct gtattttgta gatacaatga gggttcccct
5821 atccctgaat cacaatatca atgcttgagg gggaatctta attcttgcac ttttacccct
5881 attatcggga actttcttaa gcgattcgca tttgctaatg gtgtgctcta tgccaactgc
5941 aaatctttgc tatgtaggtg tgccgacccc ccccatgttg tatcccagga tgatacccaa
6001 ggcatcagca taattgatat taagagatgc tctgagatga tgcttgacac tttttcattt
6061 aggatcacat ctactttcaa tgctacgtac gtgacagact tctcaatgat taatgcaaat
6121 attgtacatc taagtcctct agatttgtca aatcaaatca attcaataaa caaatctctt
6181 aaaagtgctg aggattggat tgcagatagc aacttctttg ctaatcaagc caggacagcc
6241 aagacacttt attcactaag tgcaatagca ttaatactat cagtgattac tttggttgtc
6301 gtgggattgc tgattgccta catcatcaag ctggtttctc aaatccatca attcagatcg
6361 ctagctgcta caacaatgtt ccacagggaa aatcctgcct tcttttccaa gaataaccat
6421 ggaaacatat atgggatatc ttaa
```

// SEQ ID NO: 32 (CDS sequence: nucleic acid sequence encoding the F protein of PIV-2 referenced as SEQ ID NO : 33)

Figure 1B

```
# Program: matcher
# 1: F PIV5 (aa 4 to 529 of SEQ ID NO: 31)
# 2: F PIV2 (aa 8 to 533 of SEQ ID NO: 33)
# Matrix: EBLOSUM62
# Gap_penalty: 14
# Extend_penalty: 4
# Length: 526
# Identity:     251/526 (47.7%)
# Similarity:   361/526 (68.6%)
# Gaps:           0/526 ( 0.0%)
            10        20        30        40        50
       IIQFLVVSCLLAGAGSLDLAALMQIGVIPTNVRQLMYYTEASSAFIVVKL
       :.   :.   . :. ..    :. :::: . .: :::::.  ..::::::
       IVCIFVMYTGIVGSDAIAGDQLLNIGVIQSKIRSLMYYTDGGASFIVVKL
        10        20        30        40        50

            60        70        80        90       100
       MPTIDSPISGCNITSISSYNATVTKLLQPIGENLETIRNQLIPTRRRRRF
       .: .      :::::. .:: :. ::: :. :::  :        :..::
       LPNLPPSNGTCNITSLDAYNVTLFKLLTPLIENLSKISTVTDTKTRQKRF
        60        70        80        90       100

           110       120       130       140       150
       AGVVIGLAALGVATAAQVTAAVALVKANENAAAILNLKNAIQKTNAAVAD
       ::::.::::::::::::.:::::.:::: ::::: :: ..:: :: ::.:
       AGVVVGLAALGVATAAQITAAVAIVKANANAAAINNLASSIQSTNKAVSD
       110       120       130       140       150

           160       170       180       190       200
       VVQATQSLGTAVQAVQDHINSVVSPAITAANCKAQDAIIGSILNLYLTEL
       :. :.... :::::.:: ::  .   ::.:.:.: ::.::::::::::::
       VIDASRTIATAVQAIQDRINGAIVNGITSASCRAHDALIGSILNLYLTEL
       160       170       180       190       200

           210       220       230       240       250
       TTIFHNQITNPALSPITIQALRILLGSTLPTVVEKSFNTQISAAELLSSG
       :::::::::::::.:..::::::::::::: :.:   ::  . :::::::
       TTIFHNQITNPALTPLSIQALRILLGSTLPIVIESKLNTNFNTAELLSSG
       210       220       230       240       250

           260       270       280       290       300
       LLTGQIVGLDLTYMQMVIKIELPTLTVQPATQIIDLATISAFINNQEVMA
       ::::::. .   ::::.:.: .::  .::  ..:::  :::    :::. 
       LLTGQIISISPMYMQMLIQINVPTFIMQPGAKVIDLIAISANHKLQEVVV
       260       270       280       290       300

           310       320       330       340       350
       QLPTRVMVTGSLIQAYPASQCTITPNTVYCRYNDAQVLSDDTMACLQGNL
       :.: :..   . .: :::. : .:::.:.::::.   . .    ::.:::
       QVPNRILEYANELQNYPANDCVVTPNSVFCRYNEGSPIPESQYQCLRGNL
       310       320       330       340       350

           360       370       380       390       400
       TRCTFSPVVGSFLTRFVLFDGIVYANCRSMLCKCMQPAAVILQPSSSPVT
         :::.:..:.:: ::   .:..::::.:.::.:  :  :.  :  .  ..
       NSCTFTPIIGNFLKRFAFANGVLYANCKSLLCRCADPPHVVSQDDTQGIS
       360       370       380       390       400

           410       420       430       440       450
       VIDMYKCVSLQLDNLRFTITQLANVTYNSTIKLESSQILPIDPLDISQNL
       .::. .:  . ::   : ::   : ::  .   . .. :. . :::.:  .
       IIDIKRCSEMMLDTFSFRITSTFNATYVTDFSMINANIVHLSPLDLSNQI
       410       420       430       440       450

           460       470       480       490       500
       AAVNKSLSDALQHLAQSDTYLSAITSATTTSVLSIIAICLGSLGLILIIL
        ..::::  :   .: :. . .   .: :   :: ::. :  . :... :
       NSINKSLKSAEDWIADSNFFANQARTAKTLYSLSAIALILSVITLVVVGL
       460       470       480       490       500

           510       520
       LSVVVWKLLTIVAANRNRMENFVYHK
       :   . ::.. .   :.     ..:.
       LIAYIIKLVSQIHQFRSLAATTMFHR
       510       520       530
```

Figure 2A

| F of PIV-5 (SEQ ID NO: 31) | F of hPIV-2 (SEQ ID NO: 33) |
|---|---|
| L22P | I24P |
| K132E | K133E |
| V290A | I294A |
| S443P | S428P |
| L447P | I445P |
| I449P | S439P |
| V402A | I406A |
| I49A | I53A |
| T147V | T151V |
| T158V | S162V |
| A463V | S474V |

Figure 2B

SEQUENCE LISTING

<160> NUMBER OF SEQ ID NOS: 90

<210> SEQ ID NO 1
<211> LENGTH: 23
<212> TYPE: DNA
<213> ORGANISM: Artificial
<220> FEATURE:

<223> OTHER INFORMATION: PIV-5 F primer

<400> SEQUENCE: 1
ttgcggccgc atgggtacta taa 23

<210> SEQ ID NO 2
<211> LENGTH: 30
<212> TYPE: DNA
<213> ORGANISM: Artificial
<220> FEATURE:
<223> OTHER INFORMATION: PIV-5 F primer

<400> SEQUENCE: 2
ccgctcgagt tatgataaac aaaattctcc 30

<210> SEQ ID NO 3
<211> LENGTH: 41
<212> TYPE: DNA
<213> ORGANISM: Artificial
<220> FEATURE:
<223> OTHER INFORMATION: primer for PIV-5 F mutagenesis

<400> SEQUENCE: 3
ggagcaggca gccttgatcc agctgctctc atgcaaatcg g 41

<210> SEQ ID NO 4
<211> LENGTH: 41
<212> TYPE: DNA
<213> ORGANISM: Artificial
<220> FEATURE:
<223> OTHER INFORMATION: primer for PIV-5 F mutagenesis

<400> SEQUENCE: 4
ccgatttgca tgagagcagc tggatcaagg ctgcctgctc c 41

<210> SEQ ID NO 5
<211> LENGTH: 36
<212> TYPE: DNA
<213> ORGANISM: Artificial
<220> FEATURE:
<223> OTHER INFORMATION: primer for PIV-5 F mutagenesis

<400> SEQUENCE: 5
ggcctcatca gcattcgctg ttgtgaagtt aatgcc 36

<210> SEQ ID NO 6
<211> LENGTH: 36
<212> TYPE: DNA
<213> ORGANISM: Artificial
<220> FEATURE:
<223> OTHER INFORMATION: primer for PIV-5 F mutagenesis

<400> SEQUENCE: 6
ggcattaact tcacaacagc gaatgctgat gaggcc 36

<210> SEQ ID NO 7
<211> LENGTH: 39
<212> TYPE: DNA
<213> ORGANISM: Artificial
<220> FEATURE:
<223> OTHER INFORMATION: primer for PIV-5 F mutagenesis

<400> SEQUENCE: 7
cagccaagtt catctcctgc aactgtcatt gacatgtac 39

-continued

<210> SEQ ID NO 8
<211> LENGTH: 40
<212> TYPE: DNA
<213> ORGANISM: Artificial
<220> FEATURE:
<223> OTHER INFORMATION: primer for PIV-5 F mutagenesis

<400> SEQUENCE: 8
gtacatgtca atgacagttg caggagagtg aacttggctg 40

<210> SEQ ID NO 9
<211> LENGTH: 47
<212> TYPE: DNA
<213> ORGANISM: Artificial
<220> FEATURE:
<223> OTHER INFORMATION: primer for PIV-5 F mutagenesis

<400> SEQUENCE: 9
gcttgaatca tctcagatct tgtccattga tccgttggat atatccc 47

<210> SEQ ID NO 10
<211> LENGTH: 47
<212> TYPE: DNA
<213> ORGANISM: Artificial
<220> FEATURE:
<223> OTHER INFORMATION: primer for PIV-5 F mutagenesis

<400> SEQUENCE: 10
gggatatatc caacggatca atggacaaga tctgagatga ttcaagc 47

<210> SEQ ID NO 11
<211> LENGTH: 50
<212> TYPE: DNA
<213> ORGANISM: Artificial
<220> FEATURE:
<223> OTHER INFORMATION: primer for PIV-5 F mutagenesis

<400> SEQUENCE: 11
ctcagatctt gtccattgat ccgccggata tatcccagaa tctagctgcg 50

<210> SEQ ID NO 12
<211> LENGTH: 50
<212> TYPE: DNA
<213> ORGANISM: Artificial
<220> FEATURE:
<223> OTHER INFORMATION: primer for PIV-5 F mutagenesis

<400> SEQUENCE: 12
cgcagctaga ttctgggata tatccggcgg atcaatggac aagatctgag 50

<210> SEQ ID NO 13
<211> LENGTH: 46
<212> TYPE: DNA
<213> ORGANISM: Artificial
<220> FEATURE:
<223> OTHER INFORMATION: primer for PIV-5 F mutagenesis

<400> SEQUENCE: 13
cttgtccatt gatccgttgg atccatccca gaatctagct gcggtg 46

<210> SEQ ID NO 14
<211> LENGTH: 45
<212> TYPE: DNA
<213> ORGANISM: Artificial
<220> FEATURE:
<223> OTHER INFORMATION: primer for PIV-5 F mutagenesis

<400> SEQUENCE: 14
caccgcagct agattcgttg gatttctccc agaatctagc tgcgg 45

<210> SEQ ID NO 15
<211> LENGTH: 41
<212> TYPE: DNA
<213> ORGANISM: Artificial
<220> FEATURE:
<223> OTHER INFORMATION: primer for PIV-5 F mutagenesis

<400> SEQUENCE: 15
gcccattgat ccgttggatt tctcccagaa tctagctgcg g 41

<210> SEQ ID NO 16
<211> LENGTH: 41
<212> TYPE: DNA
<213> ORGANISM: Artificial
<220> FEATURE:
<223> OTHER INFORMATION: primer for PIV-5 F mutagenesis

<400> SEQUENCE: 16
ccgcagctag attctgggag aaatccaacg gatcaatggg c 41

<210> SEQ ID NO 17
<211> LENGTH: 43
<212> TYPE: DNA
<213> ORGANISM: Artificial
<220> FEATURE:
<223> OTHER INFORMATION: primer for PIV-5 F mutagenesis

<400> SEQUENCE: 17
ctcaaaaatg caatccaaaa agtaaatgca gcagttgcag atg 43

<210> SEQ ID NO 18
<211> LENGTH: 43
<212> TYPE: DNA
<213> ORGANISM: Artificial
<220> FEATURE:
<223> OTHER INFORMATION: primer for PIV-5 F mutagenesis

<400> SEQUENCE: 18
catctgcaac tgctgcattt actttttgga ttgcattttt gag 43

<210> SEQ ID NO 19
<211> LENGTH: 38
<212> TYPE: DNA
<213> ORGANISM: Artificial
<220> FEATURE:
<223> OTHER INFORMATION: primer for PIV-5 F mutagenesis

<400> SEQUENCE: 19
gcagatgtgg tccaggccgt acaatcacta ggaacggc 38

<210> SEQ ID NO 20
<211> LENGTH: 38
<212> TYPE: DNA
<213> ORGANISM: Artificial
<220> FEATURE:
<223> OTHER INFORMATION: primer for PIV-5 F mutagenesis

<400> SEQUENCE: 20
gccgttccta gtgattgtac ggcctggacc acatctgc 38

<210> SEQ ID NO 21
<211> LENGTH: 46

<212> TYPE: DNA
<213> ORGANISM: Artificial
<220> FEATURE:
<223> OTHER INFORMATION: primer for PIV-5 F mutagenesis

<400> SEQUENCE: 21
gtgaataaga gtctaagtga tgtactacaa cacttagcac aaagtg 46

<210> SEQ ID NO 22
<211> LENGTH: 46
<212> TYPE: DNA
<213> ORGANISM: Artificial
<220> FEATURE:
<223> OTHER INFORMATION: primer for PIV-5 F mutagenesis

<400> SEQUENCE: 22
cactttgtgc taagtgttgt agtacatcac ttagactctt attcac 46

<210> SEQ ID NO 23
<211> LENGTH: 5
<212> TYPE: PRT
<213> ORGANISM: Parainfluenza type 5

<400> SEQUENCE: 23

Arg Arg Arg Arg Arg
1 5

<210> SEQ ID NO 24
<211> LENGTH: 28
<212> TYPE: PRT
<213> ORGANISM: Parainfluenza type 5

<400> SEQUENCE: 24

Ile Gly Glu Asn Leu Glu Thr Ile Arg Asn Gln Leu Ile Pro Thr Arg
1 5 10 15

Arg Arg Arg Arg Phe Ala Gly Val Val Ile Gly Leu
20 25

<210> SEQ ID NO 25
<211> LENGTH: 6
<212> TYPE: PRT
<213> ORGANISM: Parainfluenza type 2

<400> SEQUENCE: 25

Lys Thr Arg Gln Lys Arg
1 5

<210> SEQ ID NO 26
<211> LENGTH: 37
<212> TYPE: PRT
<213> ORGANISM: Parainfluenza type 2

<400> SEQUENCE: 26

Leu Thr Pro Leu Ile Glu Asn Leu Ser Lys Ile Ser Thr Val Thr Asp
1 5 10 15

Thr Lys Thr Arg Gln Lys Arg Phe Ala Gly Val Val Val Gly Leu Ala
20 25 30

Ala Leu Gly Val Ala
35

<210> SEQ ID NO 27
<211> LENGTH: 5
<212> TYPE: PRT
<213> ORGANISM: Homo sapiens

-continued

<220> FEATURE:
<221> NAME/KEY: MISC_FEATURE
<222> LOCATION: (2)..(3)
<223> OTHER INFORMATION: any amino acid
<220> FEATURE:
<221> NAME/KEY: MISC_FEATURE
<222> LOCATION: (4)..(4)
<223> OTHER INFORMATION: any hydrophobic amino acid (F, M, V, L, I)
<220> FEATURE:
<221> NAME/KEY: MISC_FEATURE
<222> LOCATION: (5)..(5)
<223> OTHER INFORMATION: Ser ou Thr

<400> SEQUENCE: 27

```
Pro Xaa Xaa Xaa Xaa
1               5
```

<210> SEQ ID NO 28
<211> LENGTH: 5
<212> TYPE: PRT
<213> ORGANISM: Homo sapiens

<400> SEQUENCE: 28

```
Pro Arg Arg Ile Thr
1               5
```

<210> SEQ ID NO 29
<211> LENGTH: 28
<212> TYPE: PRT
<213> ORGANISM: Artificial
<220> FEATURE:
<223> OTHER INFORMATION: PIV-5 F MMP-9 site

<400> SEQUENCE: 29

```
Ile Gly Glu Asn Leu Glu Thr Ile Arg Asn Gln Leu Ile Pro Thr Pro
1               5                   10                  15

Arg Arg Ile Thr Phe Ala Gly Val Val Ile Gly Leu
            20                  25
```

<210> SEQ ID NO 30
<211> LENGTH: 1590
<212> TYPE: DNA
<213> ORGANISM: Parainfluenza type 5

<400> SEQUENCE: 30

```
atgggtacta ttattcaatt tctggtggtc tcctgtctat tggcaggagc aggcagcctt     60

gatctagcag ccctcatgca aatcggtgtc attccaacaa atgtccggca acttatgtat    120

tatactgagg cctcatcggc attcattgtt gtgaagttaa tgcctacaat tgactcgccg    180

attagtggat gtaatataac atcaatttca agctataatg caacagtgac aaaactccta    240

cagccgatcg gtgagaattt ggagacgatt aggaaccagt tgattccaac tcggagaaga    300

cgccggtttg caggggtggt gattggatta gctgcattag gagtagctac tgccgcacag    360

gtcactgccg cagtagcact agtaaaggca aatgaaaatg ctgcggctat actcaatctc    420

aaaaatgcaa tccaaaaaac aaatgcagca gttgcagatg tggtccaggc cacacaatca    480

ctaggaacgg cagttcaagc agttcaagat cacataaaca gtgtggtaag tccagcaatt    540

acagcagcca attgtaaggc ccaagatgct atcattggct caatcctcaa tctctatttg    600

accgagttga caaccatctt ccacaatcaa attacaaacc ctgcattgag tcccattaca    660

attcaagctt taaggatcct actggggagt accttgccga ctgtggtcga aaaatctttc    720

aatacccaga taagtgcagc tgagcttctc tcatcagggt tattgacagg ccagattgtg    780
```

```
ggattagatt tgacctatat gcagatggtc ataaaaattg agctgccaac tttaactgta    840

caacctgcaa cccagatcat agatctggcc accatttctg cattcattaa caatcaagaa    900

gtcatggccc aattaccaac acgtgttatg gtgactggca gcttgatcca agcctatccc    960

gcatcgcaat gcaccattac acccaacact gtgtactgta ggtataatga tgcccaagta   1020

ctctcagatg atactatggc ttgcctccaa ggtaacttga caagatgcac cttctctcca   1080

gtggttggga gctttctcac tcgattcgtg ctgttcgatg gaatagttta tgcaaattgc   1140

aggtcgatgt tgtgcaagtg catgcaacct gctgctgtga tcctacagcc gagttcatcc   1200

cctgtaactg tcattgacat gtacaaatgt gtgagtctgc agcttgacaa tctcagattc   1260

accatcactc aattggccaa tgtaacctac aatagcacca tcaagcttga atcatcccag   1320

atcttgccta ttgatccgtt ggatatatcc cagaatctag ctgcggtgaa taagagtcta   1380

agtgatgcac tacaacactt agcacaaagt gacacatatc tttctgcaat cacatcagct   1440

acgactacaa gtgtattatc cataatagca atctgtcttg gatcgttagg tttaatatta   1500

ataatcttgc tcagtgtagt tgtgtggaag ttattgacca ttgtcgctgc taatcgaaat   1560

agaatggaga attttgttta tcataaataa                                    1590
```

<210> SEQ ID NO 31
<211> LENGTH: 529
<212> TYPE: PRT
<213> ORGANISM: Parainfluenza type 5

<400> SEQUENCE: 31

```
Met Gly Thr Ile Ile Gln Phe Leu Val Val Ser Cys Leu Leu Ala Gly
1               5                   10                  15

Ala Gly Ser Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
```

-continued

```
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys
```

```
<210> SEQ ID NO 32
<211> LENGTH: 1656
<212> TYPE: DNA
<213> ORGANISM: Parainfluenza type 2

<400> SEQUENCE: 32

atgcatcacc tgcatccaat gatagtatgc atctttgtta tgtacactgg aattgtaggt      60

tcagatgcca ttgctggaga tcaactactt aatatagggg tcattcaatc aaagataaga     120

tcactcatgt actatactga tggtggtgct agctttattg ttgtaaaatt gctacctaat     180

cttcccccaa gcaatggaac atgcaacatc accagtctag atgcatataa tgttacccta     240

tttaagttac taacacccct gattgagaac ctgagtaaaa tttccactgt tacagatacc     300

aaaacccgcc aaaaacgatt tgcaggagta gttgttggac ttgctgcatt aggagtagcc     360

acagccgcac aaataactgc agctgtagca atagtgaaag ctaatgcaaa tgctgctgcg     420
```

```
ataaacaatc ttgcatcttc aattcaatcc accaacaagg cagtatccga tgtgatagat    480
gcatcaagaa caattgcaac cgcagttcaa gcaattcagg atcgcatcaa tggagctatt    540
gttaatggga taacatctgc atcatgccgt gcccatgatg cactcattgg gtcaatatta    600
aatctttatc tcactgagct taccacaata tttcataatc aaataacaaa ccctgcgctg    660
acaccactct ccatccaagc tttaagaatc ctcctcggta gcaccttgcc aattgtcatt    720
gagtccaaac tcaacacaaa cttcaacaca gcagagctgc tcagttccgg actgttaact    780
ggtcaaataa tttccatttc cccaatgtac atgcaaatgc taattcaaat caatgttccg    840
acatttataa tgcaacccgg tgcgaaggta attgatctaa ttgctatctc cgcaaaccat    900
aaattgcaag aagtggttgt acaagttccg aataggattc tagagtatgc aaatgaacta    960
caaaattacc cagccaatga ctgtgtcgtg acaccgaact ctgtattttg tagatacaat   1020
gagggttccc ctatccctga atcacaatat caatgcttga gggggaatct taattcttgc   1080
acttttaccc ctattatcgg gaactttctt aagcgattcg catttgctaa tggtgtgctc   1140
tatgccaact gcaaatcttt gctatgtagg tgtgccgacc ccccccatgt tgtatcccag   1200
gatgataccc aaggcatcag cataattgat attaagagat gctctgagat gatgcttgac   1260
actttttcat ttaggatcac atctactttc aatgctacgt acgtgacaga cttctcaatg   1320
attaatgcaa atattgtaca tctaagtcct ctagatttgt caaatcaaat caattcaata   1380
aacaaatctc ttaaaagtgc tgaggattgg attgcagata gcaacttctt tgctaatcaa   1440
gccaggacag ccaagacact ttattcacta agtgcaatag cattaatact atcagtgatt   1500
actttggttg tcgtgggatt gctgattgcc tacatcatca agctggtttc tcaaatccat   1560
caattcagat cgctagctgc tacaacaatg ttccacaggg aaaatcctgc cttcttttcc   1620
aagaataacc atggaaacat atatgggata tcttaa                             1656
```

<210> SEQ ID NO 33
<211> LENGTH: 551
<212> TYPE: PRT
<213> ORGANISM: Parainfluenza type 2

<400> SEQUENCE: 33

```
Met His His Leu His Pro Met Ile Val Cys Ile Phe Val Met Tyr Thr
1               5                   10                  15

Gly Ile Val Gly Ser Asp Ala Ile Ala Gly Asp Gln Leu Leu Asn Ile
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Thr
                85                  90                  95

Val Thr Asp Thr Lys Thr Arg Gln Lys Arg Phe Ala Gly Val Val Val
            100                 105                 110

Gly Leu Ala Ala Leu Gly Val Ala Thr Ala Ala Gln Ile Thr Ala Ala
        115                 120                 125

Val Ala Ile Val Lys Ala Asn Ala Asn Ala Ala Ala Ile Asn Asn Leu
    130                 135                 140

Ala Ser Ser Ile Gln Ser Thr Asn Lys Ala Val Ser Asp Val Ile Asp
```

```
145                 150                 155                 160

Ala Ser Arg Thr Ile Ala Thr Ala Val Gln Ala Ile Gln Asp Arg Ile
                165                 170                 175

Asn Gly Ala Ile Val Asn Gly Ile Thr Ser Ala Ser Cys Arg Ala His
            180                 185                 190

Asp Ala Leu Ile Gly Ser Ile Leu Asn Leu Tyr Leu Thr Glu Leu Thr
        195                 200                 205

Thr Ile Phe His Asn Gln Ile Thr Asn Pro Ala Leu Thr Pro Leu Ser
    210                 215                 220

Ile Gln Ala Leu Arg Ile Leu Leu Gly Ser Thr Leu Pro Ile Val Ile
225                 230                 235                 240

Glu Ser Lys Leu Asn Thr Asn Phe Asn Thr Ala Glu Leu Leu Ser Ser
                245                 250                 255

Gly Leu Leu Thr Gly Gln Ile Ile Ser Ile Ser Pro Met Tyr Met Gln
            260                 265                 270

Met Leu Ile Gln Ile Asn Val Pro Thr Phe Ile Met Gln Pro Gly Ala
        275                 280                 285

Lys Val Ile Asp Leu Ile Ala Ile Ser Ala Asn His Lys Leu Gln Glu
    290                 295                 300

Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Phe
                325                 330                 335

Cys Arg Tyr Asn Glu Gly Ser Pro Ile Pro Glu Ser Gln Tyr Gln Cys
            340                 345                 350

Leu Arg Gly Asn Leu Asn Ser Cys Thr Phe Thr Pro Ile Ile Gly Asn
        355                 360                 365

Phe Leu Lys Arg Phe Ala Phe Ala Asn Gly Val Leu Tyr Ala Asn Cys
    370                 375                 380

Lys Ser Leu Leu Cys Arg Cys Ala Asp Pro Pro His Val Val Ser Gln
385                 390                 395                 400

Asp Asp Thr Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
            420                 425                 430

Thr Tyr Val Thr Asp Phe Ser Met Ile Asn Ala Asn Ile Val His Leu
        435                 440                 445

Ser Pro Leu Asp Leu Ser Asn Gln Ile Asn Ser Ile Asn Lys Ser Leu
    450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
                485                 490                 495

Leu Ser Val Ile Thr Leu Val Val Val Gly Leu Leu Ile Ala Tyr Ile
            500                 505                 510

Ile Lys Leu Val Ser Gln Ile His Gln Phe Arg Ser Leu Ala Ala Thr
        515                 520                 525

Thr Met Phe His Arg Glu Asn Pro Ala Phe Phe Ser Lys Asn Asn His
    530                 535                 540

Gly Asn Ile Tyr Gly Ile Ser
545                 550
```

<210> SEQ ID NO 34

```
<211> LENGTH: 526
<212> TYPE: PRT
<213> ORGANISM: Parainfluenza
<220> FEATURE:
<221> NAME/KEY: MISC_FEATURE
<223> OTHER INFORMATION: X=any amino acid
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(12)
<223> OTHER INFORMATION: Xaa can be any naturally occurring amino acid
<220> FEATURE:
<221> NAME/KEY: misc_feature
<222> LOCATION: (14)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (29)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (40)..(44)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(60)
<223> OTHER INFORMATION: Xaa can be any naturally occurring amino acid
<220> FEATURE:
<221> NAME/KEY: misc_feature
<222> LOCATION: (66)..(68)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(74)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
<220> FEATURE:
<221> NAME/KEY: misc_feature
<222> LOCATION: (85)..(86)
<223> OTHER INFORMATION: Xaa can be any naturally occurring amino acid
<220> FEATURE:
<221> NAME/KEY: misc_feature
<222> LOCATION: (88)..(96)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
```

<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (138)..(140)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(159)
<223> OTHER INFORMATION: Xaa can be any naturally occurring amino acid
<220> FEATURE:
<221> NAME/KEY: misc_feature
<222> LOCATION: (165)..(165)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (171)..(176)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid -continued
<220> FEATURE:
<221> NAME/KEY: misc_feature
<222> LOCATION: (231)..(231)
<223> OTHER INFORMATION: Xaa can be any naturally occurring amino acid
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (235)..(237)
<223> OTHER INFORMATION: Xaa can be any naturally occurring amino acid
<220> FEATURE:
<221> NAME/KEY: misc_feature
<222> LOCATION: (240)..(243)
<223> OTHER INFORMATION: Xaa can be any naturally occurring amino acid
<220> FEATURE:
<221> NAME/KEY: misc_feature
<222> LOCATION: (257)..(262)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (274)..(277)
<223> OTHER INFORMATION: Xaa can be any naturally occurring amino acid
<220> FEATURE:
<221> NAME/KEY: misc_feature
<222> LOCATION: (280)..(283)
<223> OTHER INFORMATION: Xaa can be any naturally occurring amino acid
<220> FEATURE:
<221> NAME/KEY: misc_feature
<222> LOCATION: (287)..(288)
<223> OTHER INFORMATION: Xaa can be any naturally occurring amino acid
<220> FEATURE:
<221> NAME/KEY: misc_feature
<222> LOCATION: (292)..(295)
<223> OTHER INFORMATION: Xaa can be any naturally occurring amino acid
<220> FEATURE:
<221> NAME/KEY: misc_feature
<222> LOCATION: (299)..(300)
<223> OTHER INFORMATION: Xaa can be any naturally occurring amino acid
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (304)..(304)
<223> OTHER INFORMATION: Xaa can be any naturally occurring amino acid
<220> FEATURE:
<221> NAME/KEY: misc_feature
<222> LOCATION: (306)..(313)
<223> OTHER INFORMATION: Xaa can be any naturally occurring amino acid
<220> FEATURE:
<221> NAME/KEY: misc_feature
<222> LOCATION: (315)..(315)
<223> OTHER INFORMATION: Xaa can be any naturally occurring amino acid
<220> FEATURE:
<221> NAME/KEY: misc_feature
<222> LOCATION: (319)..(320)
<223> OTHER INFORMATION: Xaa can be any naturally occurring amino acid
<220> FEATURE:
<221> NAME/KEY: misc_feature
<222> LOCATION: (322)..(323)
<223> OTHER INFORMATION: Xaa can be any naturally occurring amino acid
<220> FEATURE:
<221> NAME/KEY: misc_feature
<222> LOCATION: (327)..(327)

<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (334)..(344)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid
<220> FEATURE:
<221> NAME/KEY: misc_feature
<222> LOCATION: (351)..(352)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid
<220> FEATURE:
<221> NAME/KEY: misc_feature
<222> LOCATION: (358)..(359)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid
<220> FEATURE:
<221> NAME/KEY: misc_feature
<222> LOCATION: (364)..(364)
<223> OTHER INFORMATION: Xaa can be any naturally occurring amino acid
<220> FEATURE:
<221> NAME/KEY: misc_feature
<222> LOCATION: (367)..(370)
<223> OTHER INFORMATION: Xaa can be any naturally occurring amino acid
<220> FEATURE:
<221> NAME/KEY: misc_feature
<222> LOCATION: (372)..(373)
<223> OTHER INFORMATION: Xaa can be any naturally occurring amino acid
<220> FEATURE:
<221> NAME/KEY: misc_feature
<222> LOCATION: (378)..(378)
<223> OTHER INFORMATION: Xaa can be any naturally occurring amino acid
<220> FEATURE:
<221> NAME/KEY: misc_feature
<222> LOCATION: (380)..(380)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (385)..(386)
<223> OTHER INFORMATION: Xaa can be any naturally occurring amino acid
<220> FEATURE:
<221> NAME/KEY: misc_feature
<222> LOCATION: (388)..(389)
<223> OTHER INFORMATION: Xaa can be any naturally occurring amino acid
<220> FEATURE:
<221> NAME/KEY: misc_feature
<222> LOCATION: (391)..(392)
<223> OTHER INFORMATION: Xaa can be any naturally occurring amino acid
<220> FEATURE:
<221> NAME/KEY: misc_feature
<222> LOCATION: (394)..(401)
<223> OTHER INFORMATION: Xaa can be any naturally occurring amino acid
<220> FEATURE:
<221> NAME/KEY: misc_feature
<222> LOCATION: (404)..(406)
<223> OTHER INFORMATION: Xaa can be any naturally occurring amino acid
<220> FEATURE:
<221> NAME/KEY: misc_feature
<222> LOCATION: (408)..(411)
<223> OTHER INFORMATION: Xaa can be any naturally occurring amino acid
<220> FEATURE:
<221> NAME/KEY: misc_feature
<222> LOCATION: (414)..(416)
<223> OTHER INFORMATION: Xaa can be any naturally occurring amino acid
<220> FEATURE:
<221> NAME/KEY: misc_feature
<222> LOCATION: (418)..(418)
<223> OTHER INFORMATION: Xaa can be any naturally occurring amino acid
<220> FEATURE:
<221> NAME/KEY: misc_feature
<222> LOCATION: (421)..(423)
<223> OTHER INFORMATION: Xaa can be any naturally occurring amino acid
<220> FEATURE:
<221> NAME/KEY: misc_feature
<222> LOCATION: (425)..(425)
<223> OTHER INFORMATION: Xaa can be any naturally occurring amino acid
<220> FEATURE:
<221> NAME/KEY: misc_feature
<222> LOCATION: (428)..(437)
<223> OTHER INFORMATION: Xaa can be any naturally occurring amino acid
<220> FEATURE:
<221> NAME/KEY: misc_feature
<222> LOCATION: (439)..(442)
<223> OTHER INFORMATION: Xaa can be any naturally occurring amino acid
<220> FEATURE:
<221> NAME/KEY: misc_feature
<222> LOCATION: (446)..(446)
<223> OTHER INFORMATION: Xaa can be any naturally occurring amino acid
<220> FEATURE:
<221> NAME/KEY: misc_feature
<222> LOCATION: (448)..(453)
<223> OTHER INFORMATION: Xaa can be any naturally occurring amino acid
<220> FEATURE:
<221> NAME/KEY: misc_feature
<222> LOCATION: (458)..(459)
<223> OTHER INFORMATION: Xaa can be any naturally occurring amino acid
<220> FEATURE:
<221> NAME/KEY: misc_feature
<222> LOCATION: (461)..(464)
<223> OTHER INFORMATION: Xaa can be any naturally occurring amino acid
<220> FEATURE:
<221> NAME/KEY: misc_feature
<222> LOCATION: (466)..(466)
<223> OTHER INFORMATION: Xaa can be any naturally occurring amino acid
<220> FEATURE:
<221> NAME/KEY: misc_feature
<222> LOCATION: (468)..(476)
<223> OTHER INFORMATION: Xaa can be any naturally occurring amino acid
<220> FEATURE:
<221> NAME/KEY: misc_feature
<222> LOCATION: (478)..(478)
<223> OTHER INFORMATION: Xaa can be any naturally occurring amino acid
<220> FEATURE:
<221> NAME/KEY: misc_feature
<222> LOCATION: (480)..(482)
<223> OTHER INFORMATION: Xaa can be any naturally occurring amino acid
<220> FEATURE:
<221> NAME/KEY: misc_feature
<222> LOCATION: (485)..(485)
<223> OTHER INFORMATION: Xaa can be any naturally occurring amino acid
<220> FEATURE:
<221> NAME/KEY: misc_feature
<222> LOCATION: (488)..(488)
<223> OTHER INFORMATION: Xaa can be any naturally occurring amino acid
<220> FEATURE:
<221> NAME/KEY: misc_feature
<222> LOCATION: (490)..(494)
<223> OTHER INFORMATION: Xaa can be any naturally occurring amino acid
<220> FEATURE:
<221> NAME/KEY: misc_feature
<222> LOCATION: (496)..(499)
<223> OTHER INFORMATION: Xaa can be any naturally occurring amino acid
<220> FEATURE:
<221> NAME/KEY: misc_feature
<222> LOCATION: (502)..(506)
<223> OTHER INFORMATION: Xaa can be any naturally occurring amino acid
<220> FEATURE:
<221> NAME/KEY: misc_feature
<222> LOCATION: (509)..(515)
<223> OTHER INFORMATION: Xaa can be any naturally occurring amino acid
<220> FEATURE:

```
<221> NAME/KEY: misc_feature
<222> LOCATION: (517)..(524)
<223> OTHER INFORMATION: Xaa can be any naturally occurring amino acid
<220> FEATURE:
<221> NAME/KEY: misc_feature
<222> LOCATION: (526)..(526)
<223> OTHER INFORMATION: Xaa can be any naturally occurring amino acid

<400> SEQUENCE: 34

Ile Xaa Xaa Xaa Xaa Val Xaa Xaa Xaa Xaa Xaa Xaa Gly Xaa Xaa Xaa
1               5                   10                  15

Xaa Xaa Xaa Xaa Xaa Leu Xaa Xaa Ile Gly Val Ile Xaa Xaa Xaa Xaa
            20                  25                  30

Arg Xaa Leu Met Tyr Tyr Thr Xaa Xaa Xaa Xaa Xaa Phe Ile Val Val
        35                  40                  45

Lys Leu Xaa Pro Xaa Xaa Xaa Xaa Xaa Xaa Xaa Xaa Cys Asn Ile Thr
    50                  55                  60

Ser Xaa Xaa Xaa Tyr Asn Xaa Thr Xaa Xaa Lys Leu Leu Xaa Pro Xaa
65                  70                  75                  80

Xaa Glu Asn Leu Xaa Xaa Ile Xaa Xaa Xaa Xaa Xaa Xaa Xaa Xaa Xaa
                85                  90                  95

Arg Xaa Arg Phe Ala Gly Val Val Xaa Gly Leu Ala Ala Leu Gly Val
            100                 105                 110

Ala Thr Ala Ala Gln Xaa Thr Ala Ala Val Ala Xaa Val Lys Ala Asn
        115                 120                 125

Xaa Asn Ala Ala Ala Ile Xaa Asn Leu Xaa Xaa Xaa Ile Gln Xaa Thr
    130                 135                 140

Asn Xaa Ala Val Xaa Asp Val Xaa Ala Xaa Xaa Xaa Xaa Xaa Xaa Thr
145                 150                 155                 160

Ala Val Gln Ala Xaa Gln Asp Xaa Ile Asn Xaa Xaa Xaa Xaa Xaa Xaa
                165                 170                 175

Ile Thr Xaa Ala Xaa Cys Xaa Ala Xaa Asp Ala Xaa Ile Gly Ser Ile
            180                 185                 190

Leu Asn Leu Tyr Leu Thr Glu Leu Thr Thr Ile Phe His Asn Gln Ile
        195                 200                 205

Thr Asn Pro Ala Leu Xaa Pro Val Xaa Ile Gln Ala Leu Arg Ile Leu
    210                 215                 220

Leu Gly Ser Thr Leu Pro Xaa Val Xaa Glu Xaa Xaa Xaa Asn Thr Xaa
225                 230                 235                 240

Xaa Xaa Xaa Ala Glu Leu Leu Ser Ser Gly Leu Leu Thr Gly Gln Ile
                245                 250                 255

Xaa Xaa Xaa Xaa Xaa Xaa Tyr Met Gln Met Xaa Ile Xaa Ile Xaa Pro
            260                 265                 270

Thr Xaa Xaa Xaa Xaa Gln Pro Xaa Xaa Xaa Xaa Ile Asp Leu Xaa Xaa
        275                 280                 285

Ile Ser Ala Xaa Xaa Xaa Xaa Gln Glu Val Xaa Xaa Gln Xaa Pro Xaa
    290                 295                 300

Arg Xaa Xaa Xaa Xaa Xaa Xaa Xaa Xaa Gln Xaa Tyr Pro Ala Xaa Xaa
305                 310                 315                 320

Cys Xaa Xaa Thr Pro Asn Xaa Val Xaa Cys Arg Tyr Asn Xaa Xaa Xaa
                325                 330                 335

Xaa Xaa Xaa Xaa Xaa Xaa Xaa Xaa Cys Leu Xaa Gly Asn Leu Xaa Xaa
            340                 345                 350

Cys Thr Phe Xaa Pro Xaa Xaa Gly Xaa Phe Leu Xaa Arg Phe Xaa Xaa
        355                 360                 365
```

-continued

```
Xaa Xaa Gly Xaa Xaa Tyr Ala Asn Cys Xaa Ser Xaa Leu Cys Xaa Cys
    370                 375                 380

Xaa Xaa Pro Xaa Xaa Val Xaa Xaa Gln Xaa Xaa Xaa Xaa Xaa Xaa Xaa
385                 390                 395                 400

Xaa Ile Asp Xaa Xaa Xaa Cys Xaa Xaa Xaa Xaa Leu Asp Xaa Xaa Xaa
                405                 410                 415

Phe Xaa Ile Thr Xaa Xaa Xaa Asn Xaa Thr Tyr Xaa Xaa Xaa Xaa Xaa
            420                 425                 430

Xaa Xaa Xaa Xaa Xaa Ile Xaa Xaa Xaa Xaa Pro Leu Asp Xaa Ser Xaa
        435                 440                 445

Xaa Xaa Xaa Xaa Xaa Asn Lys Ser Leu Xaa Xaa Ala Xaa Xaa Xaa Xaa
    450                 455                 460

Ala Xaa Ser Xaa Xaa Xaa Xaa Xaa Xaa Xaa Xaa Xaa Ala Xaa Thr Xaa
465                 470                 475                 480

Xaa Xaa Leu Ser Xaa Ile Ala Xaa Leu Xaa Xaa Xaa Xaa Xaa Leu Xaa
                485                 490                 495

Xaa Xaa Xaa Leu Leu Xaa Xaa Xaa Xaa Xaa Lys Leu Xaa Xaa Xaa Xaa
            500                 505                 510

Xaa Xaa Xaa Arg Xaa Xaa Xaa Xaa Xaa Xaa Xaa Xaa His Xaa
        515                 520                 525


<210> SEQ ID NO 35
<211> LENGTH: 529
<212> TYPE: PRT
<213> ORGANISM: Parainfluenza type 5

<400> SEQUENCE: 35

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220
```

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Ile Ser His Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Val Ala Asn Arg Asn Arg Met Glu Asn Phe Val Tyr His
        515                 520                 525

Lys

<210> SEQ ID NO 36
<211> LENGTH: 551
<212> TYPE: PRT
<213> ORGANISM: Parainfluenza type 5

<400> SEQUENCE: 36

Met Gly Ile Ile Ile Gln Phe Leu Val Val Ser Cys Leu Leu Ala Gly
1               5                   10                  15

Ala Gly Gly Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

```
Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480
```

-continued

```
Thr Thr Thr Ser Val Leu Ser Ile Ile Ala Ile Cys Leu Gly Ser Leu
                485                 490                 495

Gly Phe Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Asn Gln Ala Phe His His Ser Gln Ser Asp Leu Ser Glu Lys Asn Gln
    530                 535                 540

Pro Ala Thr Leu Gly Thr Arg
545                 550


<210> SEQ ID NO 37
<211> LENGTH: 551
<212> TYPE: PRT
<213> ORGANISM: Parainfluenza type 5

<400> SEQUENCE: 37

Met Gly Ile Ile Ile Gln Phe Leu Val Val Ser Cys Leu Leu Ala Gly
1               5                   10                  15

Ala Gly Gly Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300
```

```
Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Phe Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Asn Gln Ala Phe His His Ser Gln Ser Asp Leu Ser Glu Lys Asn Gln
    530                 535                 540

Pro Ala Thr Leu Gly Thr Arg
545                 550


<210> SEQ ID NO 38
<211> LENGTH: 551
<212> TYPE: PRT
<213> ORGANISM: Parainfluenza type 5

<400> SEQUENCE: 38

Met Gly Ile Ile Ile Gln Phe Leu Val Val Ser Cys Leu Leu Ala Gly
1               5                   10                  15

Ala Gly Gly Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
```

-continued

```
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Met Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Phe Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Phe Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Asn Gln Ala Phe His His Ser Gln Ser Asp Leu Ser Glu Lys Asn Gln
    530                 535                 540
```

Pro Ala Thr Leu Gly Thr Arg
545 550

<210> SEQ ID NO 39
<211> LENGTH: 534
<212> TYPE: PRT
<213> ORGANISM: Parainfluenza type 5

<400> SEQUENCE: 39

Met Gly Ile Ile Ile Gln Phe Leu Val Val Ser Cys Leu Leu Ala Gly
1 5 10 15

Ala Gly Gly Leu Asp Leu Ala Ala Leu Met Gln Ile Gly Val Ile Pro
20 25 30

Thr Asn Val Arg Gln Leu Met Tyr Tyr Thr Glu Ala Ser Ser Ala Phe
35 40 45

Ile Val Val Lys Leu Met Pro Thr Ile Asp Ser Pro Ile Ser Gly Cys
50 55 60

Asn Ile Thr Ser Ile Ser Ser Tyr Asn Ala Thr Val Thr Lys Leu Leu
65 70 75 80

Gln Pro Ile Gly Glu Asn Leu Glu Thr Ile Arg Asn Gln Leu Ile Pro
85 90 95

Thr Arg Arg Arg Arg Arg Phe Ala Gly Val Val Ile Gly Leu Ala Ala
100 105 110

Leu Gly Val Ala Thr Ala Ala Gln Val Thr Ala Ala Val Ala Leu Val
115 120 125

Lys Ala Asn Glu Asn Ala Ala Ala Ile Leu Asn Leu Lys Asn Ala Ile
130 135 140

Gln Lys Thr Asn Ala Ala Val Ala Asp Val Val Gln Ala Thr Gln Ser
145 150 155 160

Leu Gly Thr Ala Val Gln Ala Val Gln Asp His Ile Asn Ser Val Val
165 170 175

Ser Pro Ala Ile Thr Ala Ala Asn Cys Lys Ala Gln Asp Ala Ile Ile
180 185 190

Gly Ser Ile Leu Asn Leu Tyr Leu Thr Glu Leu Thr Thr Ile Phe His
195 200 205

Asn Gln Ile Thr Asn Pro Ala Leu Ser Pro Ile Thr Ile Gln Ala Leu
210 215 220

Arg Ile Leu Leu Gly Ser Thr Leu Pro Thr Val Val Glu Lys Ser Phe
225 230 235 240

Asn Thr Gln Ile Ser Ala Ala Glu Leu Leu Ser Ser Gly Leu Leu Thr
245 250 255

Gly Gln Ile Val Gly Leu Asp Leu Thr Tyr Met Gln Met Val Ile Lys
260 265 270

Ile Glu Leu Pro Thr Leu Thr Val Gln Pro Ala Thr Gln Ile Ile Asp
275 280 285

Leu Ala Thr Ile Ser Ala Phe Ile Asn Asn Gln Glu Val Met Ala Gln
290 295 300

Leu Pro Thr Arg Val Met Val Thr Gly Ser Leu Ile Gln Ala Tyr Pro
305 310 315 320

Ala Ser Gln Cys Thr Ile Thr Pro Asn Thr Val Tyr Cys Arg Tyr Asn
325 330 335

Asp Ala Gln Val Leu Ser Asp Asp Thr Arg Ala Cys Leu Gln Gly Asn
340 345 350

Leu Thr Arg Cys Thr Phe Ser Pro Val Val Gly Ser Phe Leu Thr Arg

```
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Phe Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Asn Gln Ala Phe His His
    530


<210> SEQ ID NO 40
<211> LENGTH: 551
<212> TYPE: PRT
<213> ORGANISM: Parainfluenza type 5

<400> SEQUENCE: 40

Met Ser Thr Ile Ile Gln Ser Leu Val Val Ser Cys Leu Leu Ala Gly
1               5                   10                  15

Ala Gly Ser Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Thr Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Ile
                165                 170                 175

Ser Pro Ala Ile Thr Ala Ala Asn Cys Lys Ala Gln Asp Ala Ile Ile
            180                 185                 190
```

-continued

```
Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Ile Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met His Lys Cys Val Ser Leu Gln Leu Asp
                405                 410                 415

Asp Leu Arg Phe Thr Ile Thr Gln Leu Ala Asn Val Thr Tyr Asn Ser
            420                 425                 430

Thr Ile Lys Leu Glu Thr Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Asn Ser Ala Phe His His Pro Arg Ser Asp Leu Ser Glu Lys Asn Gln
    530                 535                 540

Pro Ala Thr Leu Gly Thr Arg
545                 550


<210> SEQ ID NO 41
<211> LENGTH: 551
<212> TYPE: PRT
<213> ORGANISM: Parainfluenza type 5

<400> SEQUENCE: 41

Met Gly Thr Ile Ile Gln Phe Leu Val Val Ser Cys Leu Leu Ala Gly
1               5                   10                  15
```

-continued

```
Ala Gly Ser Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Pro Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Lys Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Lys Arg Val Ile Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Ile His Lys Cys Val Ser Leu Gln Leu Asp
                405                 410                 415

Asn Leu Arg Leu Thr Ile Thr Gln Leu Ala Asn Val Thr Tyr Asn Ser
            420                 425                 430
```

```
Thr Ile Lys Leu Glu Thr Ser Gln Ile Leu Pro Ile Asp Pro Leu Asp
        435                 440                 445

Ile Ser Asn Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Ser Ile Ile Leu Leu Ser Val Ala Val Trp Arg Leu Leu
            500                 505                 510

Thr Ile Val Ala Ala Asn Arg Asn Arg Met Glu Asn Phe Val Tyr His
        515                 520                 525

Asn Ser Ala Phe Tyr His Ser Arg Ser Asp Leu Ser Glu Lys Asn Gln
    530                 535                 540

Pro Ala Thr Leu Gly Thr Arg
545                 550


<210> SEQ ID NO 42
<211> LENGTH: 551
<212> TYPE: PRT
<213> ORGANISM: Parainfluenza type 5

<400> SEQUENCE: 42

Met Gly Thr Ile Ile Gln Phe Leu Val Val Ser Cys Leu Leu Ala Gly
1               5                   10                  15

Ala Gly Ser Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Pro Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Lys Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255
```

```
Gly Gln Ile Val Gly Leu Asp Leu Thr Tyr Met Gln Met Val Ile Lys
            260                 265                 270

Ile Glu Leu Pro Thr Leu Ala Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Lys Arg Val Ile Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Ile His Lys Cys Val Ser Leu Gln Leu Asp
                405                 410                 415

Asn Leu Arg Leu Thr Ile Thr Gln Leu Ala Asn Val Thr Tyr Asn Ser
            420                 425                 430

Thr Ile Lys Leu Glu Thr Ser Gln Ile Leu Pro Ile Asp Pro Leu Asp
        435                 440                 445

Ile Ser Asn Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Ser Ile Ile Leu Leu Ser Val Ala Val Trp Arg Leu Leu
            500                 505                 510

Thr Ile Val Ala Ala Asn Arg Asn Arg Met Glu Asn Phe Val Tyr His
        515                 520                 525

Asn Ser Ala Phe Tyr His Ser Arg Ser Asp Leu Ser Glu Lys Asn Gln
    530                 535                 540

Pro Ala Thr Leu Gly Thr Arg
545                 550


<210> SEQ ID NO 43
<211> LENGTH: 551
<212> TYPE: PRT
<213> ORGANISM: Parainfluenza type 5

<400> SEQUENCE: 43

Met Gly Thr Arg Ile Gln Phe Leu Val Val Ser Cys Leu Leu Ala Gly
1               5                   10                  15

Ser Gly Ser Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
```

-continued

```
65                  70                  75                  80

Gln Pro Ile Gly Glu Asn Leu Glu Thr Ile Arg Tyr Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Lys Asn Ala Val Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Ile Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Phe Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Thr Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495
```

```
Gly Leu Ile Leu Ile Ile Leu Leu Ser Ala Val Val Trp Lys Leu Leu
            500                 505                 510

Thr Ile Val Ala Ala Asn Arg Asn Arg Met Glu Asn Phe Val Tyr His
        515                 520                 525

Asn Ser Ala Phe His His Ser Arg Ser Asp Leu Ser Glu Lys Asn Gln
    530                 535                 540

Pro Ala Thr Leu Gly Thr Arg
545                 550


<210> SEQ ID NO 44
<211> LENGTH: 551
<212> TYPE: PRT
<213> ORGANISM: Parainfluenza type 5

<400> SEQUENCE: 44

Met Gly Thr Arg Ile Gln Phe Leu Val Val Ser Cys Leu Leu Ala Gly
1               5                   10                  15

Ser Gly Ser Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Tyr Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Lys Asn Ala Val Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Ile Val Thr Gly Ser Leu Ile Gln Ala Tyr Pro
```

305 310 315 320

Ala Ser Gln Cys Thr Ile Thr Pro Asn Thr Val Tyr Cys Arg Tyr Asn
325 330 335

Asp Ala Gln Val Leu Ser Asp Asp Thr Met Ala Cys Leu Gln Gly Asn
340 345 350

Leu Thr Arg Cys Thr Phe Ser Pro Val Val Gly Ser Phe Leu Thr Arg
355 360 365

Phe Val Leu Phe Asp Gly Ile Val Phe Ala Asn Cys Arg Ser Met Leu
370 375 380

Cys Lys Cys Met Gln Pro Ala Ala Val Ile Leu Gln Pro Ser Ser Ser
385 390 395 400

Pro Val Thr Val Ile Asp Met Tyr Lys Cys Val Ser Leu Gln Leu Asp
405 410 415

Asn Leu Arg Phe Thr Ile Thr Gln Leu Ala Asn Val Thr Tyr Asn Ser
420 425 430

Thr Ile Lys Leu Glu Thr Ser Gln Ile Leu Pro Ile Asp Pro Leu Asp
435 440 445

Ile Ser Gln Asn Leu Ala Ala Val Asn Lys Ser Leu Ser Asp Ala Leu
450 455 460

Gln His Leu Ala Gln Ser Asp Thr Tyr Leu Ser Ala Ile Thr Ser Ala
465 470 475 480

Thr Thr Thr Ser Val Leu Ser Ile Ile Ala Ile Cys Leu Gly Ser Leu
485 490 495

Gly Leu Ile Leu Ile Ile Leu Leu Ser Ala Val Val Trp Lys Leu Leu
500 505 510

Thr Ile Val Ala Ala Asn Arg Asn Arg Met Glu Asn Phe Val Tyr His
515 520 525

Asn Ser Ala Phe His His Ser Arg Ser Asp Leu Ser Glu Lys Asn Gln
530 535 540

Pro Ala Thr Leu Gly Thr Arg
545 550

<210> SEQ ID NO 45
<211> LENGTH: 551
<212> TYPE: PRT
<213> ORGANISM: Parainfluenza type 5

<400> SEQUENCE: 45

Met Gly Thr Arg Ile Gln Phe Leu Val Val Ser Cys Leu Leu Ala Gly
1 5 10 15

Thr Gly Ser Leu Asp Leu Ala Ala Leu Met Gln Ile Gly Val Ile Pro
20 25 30

Thr Asn Val Arg Gln Leu Met Tyr Tyr Thr Glu Ala Ser Ser Ala Phe
35 40 45

Ile Val Val Lys Leu Met Pro Thr Ile Asp Ser Pro Ile Ser Gly Cys
50 55 60

Asn Ile Thr Ser Ile Ser Ser Tyr Asn Ala Thr Met Thr Lys Leu Leu
65 70 75 80

Gln Pro Ile Gly Glu Asn Leu Glu Thr Ile Arg Tyr Gln Leu Ile Pro
85 90 95

Thr Arg Arg Arg Arg Arg Phe Ala Gly Val Val Ile Gly Leu Ala Ala
100 105 110

Leu Gly Val Ala Thr Ala Ala Gln Val Thr Ala Ala Val Ala Leu Val
115 120 125

-continued

```
Lys Ala Asn Lys Asn Ala Val Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Val Thr Ile Ser Ala Phe Ile Asn Asn Gln Glu Val Met Ala Gln
    290                 295                 300

Leu Pro Thr Arg Val Ile Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Ile Thr Tyr Asn Ser
            420                 425                 430

Thr Ile Lys Leu Glu Thr Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Ala Val Val Trp Lys Leu Leu
            500                 505                 510

Thr Ile Val Ala Ala Asn Arg Asn Arg Met Glu Asn Phe Val Tyr His
        515                 520                 525

Asn Ser Ala Phe His His Ser Arg Ser Asp Leu Ser Glu Lys Asn Gln
    530                 535                 540

Pro Ala Thr Leu Gly Thr Arg
```

545 550

<210> SEQ ID NO 46
<211> LENGTH: 551
<212> TYPE: PRT
<213> ORGANISM: Parainfluenza type 5

<400> SEQUENCE: 46

Met Gly Thr Ile Ile Gln Phe Leu Val Val Ser Cys Leu Leu Ala Gly
1 5 10 15

Ala Gly Ser Leu Asp Leu Ala Ala Leu Met Gln Ile Gly Val Ile Pro
20 25 30

Thr Asn Val Arg Gln Leu Met Tyr Tyr Thr Glu Ala Ser Ser Ala Phe
35 40 45

Ile Val Val Lys Leu Met Pro Thr Ile Asp Ser Pro Ile Ser Gly Cys
50 55 60

Asn Ile Thr Ser Ile Ser Ser Tyr Asn Ala Thr Val Thr Lys Leu Leu
65 70 75 80

Gln Pro Ile Gly Glu Asn Leu Glu Thr Ile Arg Asn Gln Leu Ile Pro
85 90 95

Thr Arg Arg Arg Arg Arg Phe Ala Gly Val Val Ile Gly Leu Ala Ala
100 105 110

Leu Gly Val Ala Thr Ala Ala Gln Val Thr Ala Ala Val Ala Leu Val
115 120 125

Lys Ala Asn Lys Asn Ala Ala Ala Ile Leu Asn Leu Lys Asn Ala Ile
130 135 140

Gln Lys Thr Asn Thr Ala Val Ala Asp Val Val Gln Ala Thr Gln Ser
145 150 155 160

Leu Gly Thr Ala Val Gln Ala Val Gln Asp His Ile Asn Ser Val Val
165 170 175

Ser Pro Ala Ile Thr Ala Ala Asn Cys Lys Ala Gln Asp Ala Ile Ile
180 185 190

Gly Ser Ile Leu Asn Leu Tyr Leu Thr Glu Leu Thr Thr Ile Phe His
195 200 205

Asn Gln Ile Thr Asn Pro Ala Leu Ser Pro Ile Thr Ile Gln Ala Leu
210 215 220

Arg Ile Leu Leu Gly Ser Thr Leu Pro Thr Val Val Glu Lys Ser Phe
225 230 235 240

Asn Thr Gln Ile Ser Ala Ala Glu Leu Leu Ser Ser Gly Leu Leu Thr
245 250 255

Gly Gln Ile Val Gly Leu Asp Leu Thr Tyr Met Gln Met Val Ile Lys
260 265 270

Ile Glu Leu Pro Thr Leu Thr Val Gln Pro Ala Thr Gln Ile Ile Asp
275 280 285

Leu Ala Thr Ile Ser Ala Phe Ile Asn Asn Gln Glu Val Met Ala Gln
290 295 300

Leu Pro Thr Arg Val Ile Val Thr Gly Ser Leu Ile Gln Ala Tyr Pro
305 310 315 320

Ala Ser Gln Cys Thr Ile Thr Pro Asn Thr Val Tyr Cys Arg Tyr Asn
325 330 335

Asp Ala Gln Val Leu Ser Asp Asp Thr Met Ala Cys Leu Gln Gly Asn
340 345 350

Leu Thr Arg Cys Thr Phe Ser Pro Val Val Gly Ser Phe Leu Thr Arg
355 360 365

-continued

```
Phe Met Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Thr Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Met Ala Ile Cys Leu Gly Ser Leu
                485                 490                 495

Gly Leu Ile Leu Ile Ile Leu Leu Ser Thr Val Val Trp Lys Leu Leu
            500                 505                 510

Thr Ile Val Ala Ala Asn Arg Asn Arg Met Glu Asn Phe Val Tyr His
        515                 520                 525

Asn Ser Ala Phe His His Ser Arg Ser Asp Leu Ser Glu Lys Asn Gln
    530                 535                 540

Pro Ala Thr Leu Gly Thr Arg
545                 550


<210> SEQ ID NO 47
<211> LENGTH: 529
<212> TYPE: PRT
<213> ORGANISM: Artificial
<220> FEATURE:
<223> OTHER INFORMATION: PIV-5 F mutant protein

<400> SEQUENCE: 47

Met Gly Thr Ile Ile Gln Phe Leu Val Val Ser Cys Leu Leu Ala Gly
1               5                   10                  15

Ala Gly Ser Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175
```

-continued

```
Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 48
<211> LENGTH: 529
<212> TYPE: PRT
<213> ORGANISM: Artificial
<220> FEATURE:
<223> OTHER INFORMATION: PIV-5 F mutant protein

<400> SEQUENCE: 48

Met Gly Thr Ile Ile Gln Phe Leu Val Val Ser Cys Leu Leu Ala Gly
```

-continued

```
1               5                   10                  15

Ala Gly Ser Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ala Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430
```

```
Thr Ile Lys Leu Glu Ser Ser Gln Ile Leu Ser Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 49
<211> LENGTH: 529
<212> TYPE: PRT
<213> ORGANISM: Artificial
<220> FEATURE:
<223> OTHER INFORMATION: PIV-5 F mutant protein

<400> SEQUENCE: 49

Met Gly Thr Ile Ile Gln Phe Leu Val Val Ser Cys Leu Leu Ala Gly
1               5                   10                  15

Ala Gly Ser Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255
```

-continued

```
Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Ala Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 50
<211> LENGTH: 529
<212> TYPE: PRT
<213> ORGANISM: Artificial
<220> FEATURE:
<223> OTHER INFORMATION: PIV-5 F mutant protein

<400> SEQUENCE: 50

Met Gly Thr Ile Ile Gln Phe Leu Val Val Ser Cys Leu Leu Ala Gly
1               5                   10                  15

Ala Gly Ser Leu Asp Leu Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
```

```
            85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510
```

```
Thr Ile Val Ala Ala Asn Arg Asn Arg Met Glu Asn Phe Val Tyr His
        515                 520                 525

Lys


<210> SEQ ID NO 51
<211> LENGTH: 529
<212> TYPE: PRT
<213> ORGANISM: Artificial
<220> FEATURE:
<223> OTHER INFORMATION: PIV-5 F mutant protein

<400> SEQUENCE: 51

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335
```

```
Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 52
<211> LENGTH: 529
<212> TYPE: PRT
<213> ORGANISM: Artificial
<220> FEATURE:
<223> OTHER INFORMATION: PIV-5 F mutant protein

<400> SEQUENCE: 52

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Val Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
```

-continued

```
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys
```

<210> SEQ ID NO 53
<211> LENGTH: 529
<212> TYPE: PRT
<213> ORGANISM: Artificial
<220> FEATURE:
<223> OTHER INFORMATION: PIV-5 F mutant protein

<400> SEQUENCE: 53

-continued

```
Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Val Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415
```

```
Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 54
<211> LENGTH: 529
<212> TYPE: PRT
<213> ORGANISM: Artificial
<220> FEATURE:
<223> OTHER INFORMATION: PIV-5 F mutant protein

<400> SEQUENCE: 54

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
```

-continued

```
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 55
<211> LENGTH: 529
<212> TYPE: PRT
<213> ORGANISM: Artificial
<220> FEATURE:
<223> OTHER INFORMATION: PIV-5 F mutant protein

<400> SEQUENCE: 55

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ala Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80
```

-continued

```
Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495
```

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys

<210> SEQ ID NO 56
<211> LENGTH: 529
<212> TYPE: PRT
<213> ORGANISM: Artificial
<220> FEATURE:
<223> OTHER INFORMATION: PIV-5 F mutant protein

<400> SEQUENCE: 56

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn

```
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Ala Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 57
<211> LENGTH: 529
<212> TYPE: PRT
<213> ORGANISM: Artificial
<220> FEATURE:
<223> OTHER INFORMATION: PIV-5 F mutant protein

<400> SEQUENCE: 57

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160
```

-continued

```
Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys
```

<210> SEQ ID NO 58
<211> LENGTH: 529
<212> TYPE: PRT
<213> ORGANISM: Artificial
<220> FEATURE:
<223> OTHER INFORMATION: PIV-5 F mutant protein

<400> SEQUENCE: 58

Met Gly Thr Ile Ile Gln Phe Leu Val Val Ser Cys Leu Leu Ala Gly
1 5 10 15

Ala Gly Ser Leu Asp Pro Ala Ala Leu Met Gln Ile Gly Val Ile Pro
20 25 30

Thr Asn Val Arg Gln Leu Met Tyr Tyr Thr Glu Ala Ser Ser Ala Phe
35 40 45

Ile Val Val Lys Leu Met Pro Thr Ile Asp Ser Pro Ile Ser Gly Cys
50 55 60

Asn Ile Thr Ser Ile Ser Ser Tyr Asn Ala Thr Val Thr Lys Leu Leu
65 70 75 80

Gln Pro Ile Gly Glu Asn Leu Glu Thr Ile Arg Asn Gln Leu Ile Pro
85 90 95

Thr Arg Arg Arg Arg Arg Phe Ala Gly Val Val Ile Gly Leu Ala Ala
100 105 110

Leu Gly Val Ala Thr Ala Ala Gln Val Thr Ala Ala Val Ala Leu Val
115 120 125

Lys Ala Asn Glu Asn Ala Ala Ala Ile Leu Asn Leu Lys Asn Ala Ile
130 135 140

Gln Lys Val Asn Ala Ala Val Ala Asp Val Val Gln Ala Thr Gln Ser
145 150 155 160

Leu Gly Thr Ala Val Gln Ala Val Gln Asp His Ile Asn Ser Val Val
165 170 175

Ser Pro Ala Ile Thr Ala Ala Asn Cys Lys Ala Gln Asp Ala Ile Ile
180 185 190

Gly Ser Ile Leu Asn Leu Tyr Leu Thr Glu Leu Thr Thr Ile Phe His
195 200 205

Asn Gln Ile Thr Asn Pro Ala Leu Ser Pro Ile Thr Ile Gln Ala Leu
210 215 220

Arg Ile Leu Leu Gly Ser Thr Leu Pro Thr Val Val Glu Lys Ser Phe
225 230 235 240

Asn Thr Gln Ile Ser Ala Ala Glu Leu Leu Ser Ser Gly Leu Leu Thr
245 250 255

Gly Gln Ile Val Gly Leu Asp Leu Thr Tyr Met Gln Met Val Ile Lys
260 265 270

Ile Glu Leu Pro Thr Leu Thr Val Gln Pro Ala Thr Gln Ile Ile Asp
275 280 285

Leu Ala Thr Ile Ser Ala Phe Ile Asn Asn Gln Glu Val Met Ala Gln
290 295 300

Leu Pro Thr Arg Val Met Val Thr Gly Ser Leu Ile Gln Ala Tyr Pro
305 310 315 320

Ala Ser Gln Cys Thr Ile Thr Pro Asn Thr Val Tyr Cys Arg Tyr Asn
325 330 335

Asp Ala Gln Val Leu Ser Asp Asp Thr Met Ala Cys Leu Gln Gly Asn
340 345 350

Leu Thr Arg Cys Thr Phe Ser Pro Val Val Gly Ser Phe Leu Thr Arg
355 360 365

Phe Val Leu Phe Asp Gly Ile Val Tyr Ala Asn Cys Arg Ser Met Leu
370 375 380

Cys Lys Cys Met Gln Pro Ala Ala Val Ile Leu Gln Pro Ser Ser Ser
385 390 395 400

Pro Val Thr Val Ile Asp Met Tyr Lys Cys Val Ser Leu Gln Leu Asp

-continued

```
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 59
<211> LENGTH: 529
<212> TYPE: PRT
<213> ORGANISM: Artificial
<220> FEATURE:
<223> OTHER INFORMATION: PIV-5 F mutant protein

<400> SEQUENCE: 59

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240
```

```
Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 60
<211> LENGTH: 529
<212> TYPE: PRT
<213> ORGANISM: Artificial
<220> FEATURE:
<223> OTHER INFORMATION: PIV-5 F mutant protein

<400> SEQUENCE: 60

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60
```

-continued

```
Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Val Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Pro Ile Asp Pro Leu Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
```

```
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 61
<211> LENGTH: 529
<212> TYPE: PRT
<213> ORGANISM: Artificial
<220> FEATURE:
<223> OTHER INFORMATION: PIV-5 F mutant protein

<400> SEQUENCE: 61

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320
```

```
Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Pro Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 62
<211> LENGTH: 529
<212> TYPE: PRT
<213> ORGANISM: Artificial
<220> FEATURE:
<223> OTHER INFORMATION: PIV-5 F mutant protein

<400> SEQUENCE: 62

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140
```

-continued

```
Gln Lys Val Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Pro Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys
```

<210> SEQ ID NO 63
<211> LENGTH: 529
<212> TYPE: PRT
<213> ORGANISM: Artificial

<220> FEATURE:
<223> OTHER INFORMATION: PIV-5 F mutant protein

<400> SEQUENCE: 63

```
Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400
```

```
Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Pro Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 64
<211> LENGTH: 529
<212> TYPE: PRT
<213> ORGANISM: Artificial
<220> FEATURE:
<223> OTHER INFORMATION: PIV-5 F mutant protein

<400> SEQUENCE: 64

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Val Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220
```

```
Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Pro Asp
        435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys
```

```
<210> SEQ ID NO 65
<211> LENGTH: 529
<212> TYPE: PRT
<213> ORGANISM: Artificial
<220> FEATURE:
<223> OTHER INFORMATION: PIV-5 F mutant protein

<400> SEQUENCE: 65

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
```

-continued

```
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480
```

```
Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 66
<211> LENGTH: 529
<212> TYPE: PRT
<213> ORGANISM: Artificial
<220> FEATURE:
<223> OTHER INFORMATION: PIV-5 F mutant protein

<400> SEQUENCE: 66

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300
```

```
Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Phe Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys
```

<210> SEQ ID NO 67
<211> LENGTH: 529
<212> TYPE: PRT
<213> ORGANISM: Artificial
<220> FEATURE:
<223> OTHER INFORMATION: PIV-5 F mutant protein

<400> SEQUENCE: 67

```
Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ala Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
```

```
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys
```

<210> SEQ ID NO 68
<211> LENGTH: 529

```
<212> TYPE: PRT
<213> ORGANISM: Artificial
<220> FEATURE:
<223> OTHER INFORMATION: PIV-5 F mutant protein

<400> SEQUENCE: 68

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Val Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380
```

```
Cys Lys Cys Met Gln Pro Ala Ala Val Ile Leu Gln Pro Ser Ser Ser
385                 390                 395                 400

Pro Ala Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Val Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 69
<211> LENGTH: 529
<212> TYPE: PRT
<213> ORGANISM: Artificial
<220> FEATURE:
<223> OTHER INFORMATION: PIV-5 F mutant protein

<400> SEQUENCE: 69

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ala Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Val Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
```

```
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Ala Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Val Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 70
<211> LENGTH: 529
<212> TYPE: PRT
<213> ORGANISM: Artificial
<220> FEATURE:
<223> OTHER INFORMATION: PIV-5 F mutant protein

<400> SEQUENCE: 70

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45
```

-continued

```
Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Ala Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Ala Leu
    450                 455                 460
```

```
Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 71
<211> LENGTH: 529
<212> TYPE: PRT
<213> ORGANISM: Artificial
<220> FEATURE:
<223> OTHER INFORMATION: PIV-5 F mutant protein

<400> SEQUENCE: 71

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Val Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
```

```
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 72
<211> LENGTH: 529
<212> TYPE: PRT
<213> ORGANISM: Artificial
<220> FEATURE:
<223> OTHER INFORMATION: PIV-5 F mutant protein

<400> SEQUENCE: 72

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125
```

-continued

```
Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys
```

```
<210> SEQ ID NO 73
<211> LENGTH: 529
<212> TYPE: PRT
<213> ORGANISM: Artificial
<220> FEATURE:
<223> OTHER INFORMATION: PIV-5 F mutant protein

<400> SEQUENCE: 73

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Val Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
```

```
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 74
<211> LENGTH: 529
<212> TYPE: PRT
<213> ORGANISM: Artificial
<220> FEATURE:
<223> OTHER INFORMATION: PIV-5 F mutant protein

<400> SEQUENCE: 74

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Val Asn Ala Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205
```

```
Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Val Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 75
<211> LENGTH: 529
<212> TYPE: PRT
<213> ORGANISM: Artificial
<220> FEATURE:
<223> OTHER INFORMATION: PIV-5 F mutant protein

<400> SEQUENCE: 75

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30
```

-continued

```
Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Val Leu
```

```
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 76
<211> LENGTH: 529
<212> TYPE: PRT
<213> ORGANISM: Artificial
<220> FEATURE:
<223> OTHER INFORMATION: PIV-5 F mutant protein

<400> SEQUENCE: 76

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Val Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285
```

```
Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Val Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 77
<211> LENGTH: 529
<212> TYPE: PRT
<213> ORGANISM: Artificial
<220> FEATURE:
<223> OTHER INFORMATION: PIV-5 F mutant protein

<400> SEQUENCE: 77

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ala Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110
```

```
Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Thr Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys
```

<210> SEQ ID NO 78
<211> LENGTH: 529
<212> TYPE: PRT
<213> ORGANISM: Artificial
<220> FEATURE:
<223> OTHER INFORMATION: PIV-5 F mutant protein

<400> SEQUENCE: 78

Met Gly Thr Ile Ile Gln Phe Leu Val Val Ser Cys Leu Leu Ala Gly
1 5 10 15

Ala Gly Ser Leu Asp Pro Ala Ala Leu Met Gln Ile Gly Val Ile Pro
20 25 30

Thr Asn Val Arg Gln Leu Met Tyr Tyr Thr Glu Ala Ser Ser Ala Phe
35 40 45

Ala Val Val Lys Leu Met Pro Thr Ile Asp Ser Pro Ile Ser Gly Cys
50 55 60

Asn Ile Thr Ser Ile Ser Ser Tyr Asn Ala Thr Val Thr Lys Leu Leu
65 70 75 80

Gln Pro Ile Gly Glu Asn Leu Glu Thr Ile Arg Asn Gln Leu Ile Pro
85 90 95

Thr Arg Arg Arg Arg Arg Phe Ala Gly Val Val Ile Gly Leu Ala Ala
100 105 110

Leu Gly Val Ala Thr Ala Ala Gln Val Thr Ala Ala Val Ala Leu Val
115 120 125

Lys Ala Asn Glu Asn Ala Ala Ala Ile Leu Asn Leu Lys Asn Ala Ile
130 135 140

Gln Lys Val Asn Ala Ala Val Ala Asp Val Val Gln Ala Val Gln Ser
145 150 155 160

Leu Gly Thr Ala Val Gln Ala Val Gln Asp His Ile Asn Ser Val Val
165 170 175

Ser Pro Ala Ile Thr Ala Ala Asn Cys Lys Ala Gln Asp Ala Ile Ile
180 185 190

Gly Ser Ile Leu Asn Leu Tyr Leu Thr Glu Leu Thr Thr Ile Phe His
195 200 205

Asn Gln Ile Thr Asn Pro Ala Leu Ser Pro Ile Thr Ile Gln Ala Leu
210 215 220

Arg Ile Leu Leu Gly Ser Thr Leu Pro Thr Val Val Glu Lys Ser Phe
225 230 235 240

Asn Thr Gln Ile Ser Ala Ala Glu Leu Leu Ser Ser Gly Leu Leu Thr
245 250 255

Gly Gln Ile Val Gly Leu Asp Leu Thr Tyr Met Gln Met Val Ile Lys
260 265 270

Ile Glu Leu Pro Thr Leu Thr Val Gln Pro Ala Thr Gln Ile Ile Asp
275 280 285

Leu Ala Thr Ile Ser Ala Phe Ile Asn Asn Gln Glu Val Met Ala Gln
290 295 300

Leu Pro Thr Arg Val Met Val Thr Gly Ser Leu Ile Gln Ala Tyr Pro
305 310 315 320

Ala Ser Gln Cys Thr Ile Thr Pro Asn Thr Val Tyr Cys Arg Tyr Asn
325 330 335

Asp Ala Gln Val Leu Ser Asp Asp Thr Met Ala Cys Leu Gln Gly Asn
340 345 350

Leu Thr Arg Cys Thr Phe Ser Pro Val Val Gly Ser Phe Leu Thr Arg
355 360 365

```
Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys


<210> SEQ ID NO 79
<211> LENGTH: 529
<212> TYPE: PRT
<213> ORGANISM: Artificial
<220> FEATURE:
<223> OTHER INFORMATION: PIV-5 F mutant protein

<400> SEQUENCE: 79

Met Gly Thr Ile Ile Gln Phe Leu Val Val Ser Cys Leu Leu Ala Gly
1               5                   10                  15

Ala Gly Ser Leu Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ala Val Val Lys Leu Met Pro Thr Ile Asp Ser Pro Ile Ser Gly Cys
    50                  55                  60

Asn Ile Thr Ser Ile Ser Ser Tyr Asn Ala Thr Val Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Glu Asn Ala Ala Ala Ile Leu Asn Leu Lys Asn Ala Ile
    130                 135                 140

Gln Lys Val Asn Ala Ala Val Ala Asp Val Val Gln Ala Val Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190
```

-continued

```
Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
                325                 330                 335

Asp Ala Gln Val Leu Ser Asp Asp Thr Met Ala Cys Leu Gln Gly Asn
            340                 345                 350

Leu Thr Arg Cys Thr Phe Ser Pro Val Val Gly Ser Phe Leu Thr Arg
        355                 360                 365

Phe Val Leu Phe Asp Gly Ile Val Tyr Ala Asn Cys Arg Ser Met Leu
    370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Ser Ser Gln Ile Leu Ser Ile Asp Pro Leu Asp
        435                 440                 445

Pro Ser Gln Asn Leu Ala Ala Val Asn Lys Ser Leu Ser Asp Val Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Ile Ala Ile Cys Leu Gly Ser Leu
                485                 490                 495

Gly Leu Ile Leu Ile Ile Leu Leu Ser Val Val Val Trp Lys Leu Leu
            500                 505                 510

Thr Ile Val Ala Ala Asn Arg Asn Arg Met Glu Asn Phe Val Tyr His
        515                 520                 525

Lys
```

<210> SEQ ID NO 80
<211> LENGTH: 36
<212> TYPE: DNA
<213> ORGANISM: Artificial
<220> FEATURE:
<223> OTHER INFORMATION: primer for mutagenesis of PIV-5 F cleavage site

<400> SEQUENCE: 80
ccagttgatt ccaactccga ggagacgccg gtttgc 36

<210> SEQ ID NO 81

<211> LENGTH: 36
<212> TYPE: DNA
<213> ORGANISM: Artificial
<220> FEATURE:
<223> OTHER INFORMATION: primer for mutagenesis of PIV-5 F cleavage site

<400> SEQUENCE: 81
gcaaaccggc gtctcctcgg agttggaatc aactgg 36

<210> SEQ ID NO 82
<211> LENGTH: 40
<212> TYPE: DNA
<213> ORGANISM: Artificial
<220> FEATURE:
<223> OTHER INFORMATION: primer for mutagenesis of PIV-5 F cleavage site

<400> SEQUENCE: 82
gattccaact ccgaggagaa tccggtttgc aggagtggtg 40

<210> SEQ ID NO 83
<211> LENGTH: 40
<212> TYPE: DNA
<213> ORGANISM: Artificial
<220> FEATURE:
<223> OTHER INFORMATION: primer for mutagenesis of PIV-5 F cleavage site

<400> SEQUENCE: 83
caccactcct gcaaaccgga ttctcctcgg agttggaatc 40

<210> SEQ ID NO 84
<211> LENGTH: 45
<212> TYPE: DNA
<213> ORGANISM: Artificial
<220> FEATURE:
<223> OTHER INFORMATION: primer for mutagenesis of PIV-5 F cleavage site

<400> SEQUENCE: 84
gattccaact ccgaggagaa tcacgtttgc aggagtggtg attgg 45

<210> SEQ ID NO 85
<211> LENGTH: 45
<212> TYPE: DNA
<213> ORGANISM: Artificial
<220> FEATURE:
<223> OTHER INFORMATION: primer for mutagenesis of PIV-5 F cleavage site

<400> SEQUENCE: 85
ccaatcacca ctcctgcaaa cgtgattctc ctcggagttg gaatc 45

<210> SEQ ID NO 86
<211> LENGTH: 7
<212> TYPE: PRT
<213> ORGANISM: Parainfluenza type 2

<400> SEQUENCE: 86

Met His His Leu His Pro Met
1 5

<210> SEQ ID NO 87
<211> LENGTH: 18
<212> TYPE: PRT
<213> ORGANISM: Parainfluenza type 2

<400> SEQUENCE: 87

Glu Asn Pro Ala Phe Phe Ser Lys Asn Asn His Gly Asn Ile Tyr Gly
1 5 10 15

Ile Ser

<210> SEQ ID NO 88
<211> LENGTH: 551
<212> TYPE: PRT
<213> ORGANISM: Artificial
<220> FEATURE:
<223> OTHER INFORMATION: PIV-2 mutant protein

<400> SEQUENCE: 88

```
Met His His Leu His Pro Met Ile Val Cys Ile Phe Val Met Tyr Thr
1               5                   10                  15

Gly Ile Val Gly Ser Asp Ala Pro Ala Gly Asp Gln Leu Leu Asn Ile
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Thr
                85                  90                  95

Val Thr Asp Thr Lys Thr Arg Gln Lys Arg Phe Ala Gly Val Val Val
            100                 105                 110

Gly Leu Ala Ala Leu Gly Val Ala Thr Ala Ala Gln Ile Thr Ala Ala
        115                 120                 125

Val Ala Ile Val Glu Ala Asn Ala Asn Ala Ala Ala Ile Asn Asn Leu
    130                 135                 140

Ala Ser Ser Ile Gln Ser Val Asn Lys Ala Val Ser Asp Val Ile Asp
145                 150                 155                 160

Ala Ser Arg Thr Ile Ala Thr Ala Val Gln Ala Ile Gln Asp Arg Ile
                165                 170                 175

Asn Gly Ala Ile Val Asn Gly Ile Thr Ser Ala Ser Cys Arg Ala His
            180                 185                 190

Asp Ala Leu Ile Gly Ser Ile Leu Asn Leu Tyr Leu Thr Glu Leu Thr
        195                 200                 205

Thr Ile Phe His Asn Gln Ile Thr Asn Pro Ala Leu Thr Pro Leu Ser
    210                 215                 220

Ile Gln Ala Leu Arg Ile Leu Leu Gly Ser Thr Leu Pro Ile Val Ile
225                 230                 235                 240

Glu Ser Lys Leu Asn Thr Asn Phe Asn Thr Ala Glu Leu Leu Ser Ser
                245                 250                 255

Gly Leu Leu Thr Gly Gln Ile Ile Ser Ile Ser Pro Met Tyr Met Gln
            260                 265                 270

Met Leu Ile Gln Ile Asn Val Pro Thr Phe Ile Met Gln Pro Gly Ala
        275                 280                 285

Lys Val Ile Asp Leu Ala Ala Ile Ser Ala Asn His Lys Leu Gln Glu
    290                 295                 300

Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Phe
                325                 330                 335

Cys Arg Tyr Asn Glu Gly Ser Pro Ile Pro Glu Ser Gln Tyr Gln Cys
            340                 345                 350
```

-continued

```
Leu Arg Gly Asn Leu Asn Ser Cys Thr Phe Thr Pro Ile Ile Gly Asn
        355                 360                 365

Phe Leu Lys Arg Phe Ala Phe Ala Asn Gly Val Leu Tyr Ala Asn Cys
    370                 375                 380

Lys Ser Leu Leu Cys Arg Cys Ala Asp Pro Pro His Val Val Ser Gln
385                 390                 395                 400

Asp Asp Thr Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
            420                 425                 430

Thr Tyr Val Thr Asp Phe Ser Met Ile Asn Ala Asn Pro Val His Leu
        435                 440                 445

Ser Pro Leu Asp Leu Ser Asn Gln Ile Asn Ser Ile Asn Lys Ser Leu
    450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
                485                 490                 495

Leu Ser Val Ile Thr Leu Val Val Val Gly Leu Leu Ile Ala Tyr Ile
            500                 505                 510

Ile Lys Leu Val Ser Gln Ile His Gln Phe Arg Ser Leu Ala Ala Thr
        515                 520                 525

Thr Met Phe His Arg Glu Asn Pro Ala Phe Phe Ser Lys Asn Asn His
    530                 535                 540

Gly Asn Ile Tyr Gly Ile Ser
545                 550


<210> SEQ ID NO 89
<211> LENGTH: 551
<212> TYPE: PRT
<213> ORGANISM: Artificial
<220> FEATURE:
<223> OTHER INFORMATION: PIV-2 mutant protein

<400> SEQUENCE: 89

Met His His Leu His Pro Met Ile Val Cys Ile Phe Val Met Tyr Thr
1               5                   10                  15

Gly Ile Val Gly Ser Asp Ala Pro Ala Gly Asp Gln Leu Leu Asn Ile
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Thr
                85                  90                  95

Val Thr Asp Thr Lys Thr Arg Gln Lys Arg Phe Ala Gly Val Val Val
            100                 105                 110

Gly Leu Ala Ala Leu Gly Val Ala Thr Ala Ala Gln Ile Thr Ala Ala
        115                 120                 125

Val Ala Ile Val Glu Ala Asn Ala Asn Ala Ala Ala Ile Asn Asn Leu
    130                 135                 140

Ala Ser Ser Ile Gln Ser Thr Asn Lys Ala Val Ser Asp Val Ile Asp
145                 150                 155                 160
```

```
Ala Val Arg Thr Ile Ala Thr Ala Val Gln Ala Ile Gln Asp Arg Ile
            165                 170                 175

Asn Gly Ala Ile Val Asn Gly Ile Thr Ser Ala Ser Cys Arg Ala His
            180                 185                 190

Asp Ala Leu Ile Gly Ser Ile Leu Asn Leu Tyr Leu Thr Glu Leu Thr
        195                 200                 205

Thr Ile Phe His Asn Gln Ile Thr Asn Pro Ala Leu Thr Pro Leu Ser
    210                 215                 220

Ile Gln Ala Leu Arg Ile Leu Leu Gly Ser Thr Leu Pro Ile Val Ile
225                 230                 235                 240

Glu Ser Lys Leu Asn Thr Asn Phe Asn Thr Ala Glu Leu Leu Ser Ser
            245                 250                 255

Gly Leu Leu Thr Gly Gln Ile Ile Ser Ile Ser Pro Met Tyr Met Gln
            260                 265                 270

Met Leu Ile Gln Ile Asn Val Pro Thr Phe Ile Met Gln Pro Gly Ala
        275                 280                 285

Lys Val Ile Asp Leu Ala Ala Ile Ser Ala Asn His Lys Leu Gln Glu
    290                 295                 300

Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Phe
                325                 330                 335

Cys Arg Tyr Asn Glu Gly Ser Pro Ile Pro Glu Ser Gln Tyr Gln Cys
            340                 345                 350

Leu Arg Gly Asn Leu Asn Ser Cys Thr Phe Thr Pro Ile Ile Gly Asn
        355                 360                 365

Phe Leu Lys Arg Phe Ala Phe Ala Asn Gly Val Leu Tyr Ala Asn Cys
    370                 375                 380

Lys Ser Leu Leu Cys Arg Cys Ala Asp Pro Pro His Val Val Ser Gln
385                 390                 395                 400

Asp Asp Thr Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
            420                 425                 430

Thr Tyr Val Thr Asp Phe Ser Met Ile Asn Ala Asn Pro Val His Leu
        435                 440                 445

Ser Pro Leu Asp Leu Ser Asn Gln Ile Asn Ser Ile Asn Lys Ser Leu
    450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
                485                 490                 495

Leu Ser Val Ile Thr Leu Val Val Val Gly Leu Leu Ile Ala Tyr Ile
            500                 505                 510

Ile Lys Leu Val Ser Gln Ile His Gln Phe Arg Ser Leu Ala Ala Thr
        515                 520                 525

Thr Met Phe His Arg Glu Asn Pro Ala Phe Phe Ser Lys Asn Asn His
    530                 535                 540

Gly Asn Ile Tyr Gly Ile Ser
545                 550
```

<210> SEQ ID NO 90
<211> LENGTH: 551
<212> TYPE: PRT

<213> ORGANISM: Artificial
<220> FEATURE:
<223> OTHER INFORMATION: PIV-2 mutant protein

<400> SEQUENCE: 90

```
Met His His Leu His Pro Met Ile Val Cys Ile Phe Val Met Tyr Thr
1               5                   10                  15

Gly Ile Val Gly Ser Asp Ala Pro Ala Gly Asp Gln Leu Leu Asn Ile
            20                  25                  30

Gly Val Ile Gln Ser Lys Ile Arg Ser Leu Met Tyr Tyr Thr Asp Gly
        35                  40                  45

Gly Ala Ser Phe Ile Val Val Lys Leu Leu Pro Asn Leu Pro Pro Ser
    50                  55                  60

Asn Gly Thr Cys Asn Ile Thr Ser Leu Asp Ala Tyr Asn Val Thr Leu
65                  70                  75                  80

Phe Lys Leu Leu Thr Pro Leu Ile Glu Asn Leu Ser Lys Ile Ser Thr
                85                  90                  95

Val Thr Asp Thr Lys Thr Arg Gln Lys Arg Phe Ala Gly Val Val Val
            100                 105                 110

Gly Leu Ala Ala Leu Gly Val Ala Thr Ala Ala Gln Ile Thr Ala Ala
        115                 120                 125

Val Ala Ile Val Glu Ala Asn Ala Asn Ala Ala Ala Ile Asn Asn Leu
    130                 135                 140

Ala Ser Ser Ile Gln Ser Val Asn Lys Ala Val Ser Asp Val Ile Asp
145                 150                 155                 160

Ala Val Arg Thr Ile Ala Thr Ala Val Gln Ala Ile Gln Asp Arg Ile
                165                 170                 175

Asn Gly Ala Ile Val Asn Gly Ile Thr Ser Ala Ser Cys Arg Ala His
            180                 185                 190

Asp Ala Leu Ile Gly Ser Ile Leu Asn Leu Tyr Leu Thr Glu Leu Thr
        195                 200                 205

Thr Ile Phe His Asn Gln Ile Thr Asn Pro Ala Leu Thr Pro Leu Ser
    210                 215                 220

Ile Gln Ala Leu Arg Ile Leu Leu Gly Ser Thr Leu Pro Ile Val Ile
225                 230                 235                 240

Glu Ser Lys Leu Asn Thr Asn Phe Asn Thr Ala Glu Leu Leu Ser Ser
                245                 250                 255

Gly Leu Leu Thr Gly Gln Ile Ile Ser Ile Ser Pro Met Tyr Met Gln
            260                 265                 270

Met Leu Ile Gln Ile Asn Val Pro Thr Phe Ile Met Gln Pro Gly Ala
        275                 280                 285

Lys Val Ile Asp Leu Ala Ala Ile Ser Ala Asn His Lys Leu Gln Glu
    290                 295                 300

Val Val Val Gln Val Pro Asn Arg Ile Leu Glu Tyr Ala Asn Glu Leu
305                 310                 315                 320

Gln Asn Tyr Pro Ala Asn Asp Cys Val Val Thr Pro Asn Ser Val Phe
                325                 330                 335

Cys Arg Tyr Asn Glu Gly Ser Pro Ile Pro Glu Ser Gln Tyr Gln Cys
            340                 345                 350

Leu Arg Gly Asn Leu Asn Ser Cys Thr Phe Thr Pro Ile Ile Gly Asn
        355                 360                 365

Phe Leu Lys Arg Phe Ala Phe Ala Asn Gly Val Leu Tyr Ala Asn Cys
    370                 375                 380

Lys Ser Leu Leu Cys Arg Cys Ala Asp Pro Pro His Val Val Ser Gln
```

-continued

```
385                 390                 395                 400

Asp Asp Thr Gln Gly Ile Ser Ile Ile Asp Ile Lys Arg Cys Ser Glu
                405                 410                 415

Met Met Leu Asp Thr Phe Ser Phe Arg Ile Thr Ser Thr Phe Asn Ala
            420                 425                 430

Thr Tyr Val Thr Asp Phe Ser Met Ile Asn Ala Asn Pro Val His Leu
        435                 440                 445

Ser Pro Leu Asp Leu Ser Asn Gln Ile Asn Ser Ile Asn Lys Ser Leu
    450                 455                 460

Lys Ser Ala Glu Asp Trp Ile Ala Asp Ser Asn Phe Phe Ala Asn Gln
465                 470                 475                 480

Ala Arg Thr Ala Lys Thr Leu Tyr Ser Leu Ser Ala Ile Ala Leu Ile
                485                 490                 495

Leu Ser Val Ile Thr Leu Val Val Val Gly Leu Leu Ile Ala Tyr Ile
            500                 505                 510

Ile Lys Leu Val Ser Gln Ile His Gln Phe Arg Ser Leu Ala Ala Thr
        515                 520                 525

Thr Met Phe His Arg Glu Asn Pro Ala Phe Phe Ser Lys Asn Asn His
    530                 535                 540

Gly Asn Ile Tyr Gly Ile Ser
545                 550
```

MUTANT PROTEINS OF THE F PROTEIN OF PIV-5 AND PIV-2

This Application is in the National Phase Under 35 U.S.C. §371 of PCT International Application No. PCT/FR2009/001317 filed on Nov. 17, 2009, which claims priority on French application Ser. No. 08/06548 filed on Nov. 21, 2008. The entire contents of which are hereby incorporated by reference.

TECHNICAL FIELD

The present application relates to mutant proteins of the fusion protein (F protein) of parainfluenza virus (PIV) which are currently indexed as type 5 PIV (PIV-5 or PIV5) and type 2 IV (PIV-2 or PIV2).

The present application relates to products derived therefrom, such as:

- nucleic acids, vectors, cells;
- fusion inhibitors of the antibody, aptamer, interfering RNA type;
- myelomas, hybridomas;
- stem and progenitor cells.

The present application also relates to these mutant proteins and products derived therefrom for their use in medical and biotechnological applications.

PRIOR ART

The parainfluenza virus (PIV) which is currently indexed as type 5 PIV (PIV-5 or PIV5) is an enveloped virus of the genus rubulavirus in the paramyxoviridae family. PIV-5 was previously known by the name SV5 (simian virus 5), since it was initially isolated from primary monkey cell cultures. However, the natural host of PIV-5 appears to be the dog, in which it causes a cough known as kennel cough.

Subsequently, several PIV-5 isolates were obtained from samples collected from humans, but which were cultured on animal cells. Further, no symptoms or disease are associated with PIV-5 in the human being. The question of whether the human being is actually a host for PIV-5 is thus still being hotly debated.

In any event, the PIV-5 virus is currently considered to be an animal virus.

The parainfluenza virus (PIV) which is currently indexed as type 2 PIV (PIV-2 or PIV2) is also an enveloped virus of the genus rubulavirus in the paramyxoviridae family.

Currently, only human isolates of PIV-2 have been identified (hPIV-2), and so PIV-2 is considered to be a human virus.

PIV-5 and PIV-2 viruses are very similar to each other in terms of nucleic acid sequences, protein sequences, organisation, structure and morphology.

Selected from human parainfluenza viruses, PIV-2 is the closest virus to PIV-5 which has been found in the human being.

PIV-2 may be considered, and is at least considered to be so by the inventors, to be the human equivalent of PIV-5.

Infection by PIV-5 or PIV-2 leads to the formation of plurinuclear structures known as syncytia, which result from the fusion of cells from the infected host.

PIV-5 and PIV-2 viruses enter the host cell by fusion of the viral envelope with the cell membrane.

This fusion involves two viral glycoproteins: the haemagglutinin-neuraminidase attachment protein (FIN) and the fusion protein (F).

The fusion protein F of PIV-5 and PIV-2 is synthetized in the form of a simple precursor (F0) and is in the form of a glycosylated homotrimer. The fusion protein F of PIV-5 and PIV-2 requires proteolytic cleavage by host furines of the host to generate a "pre-activated" form consisting of two subunits linked via disulphide bridges: a large carboxy-terminal subunit F1 and a small amino-terminal subunit F2.

The subunit F1 is composed of a hydrophobic fusion peptide (FP) as well as two heptade repeat domains (HR-1 and HR-2) having a coiled-coil type conformation. After activation by HN, the fusion protein undergoes a series of conformational changes resulting in insertion of the fusion peptide into the target cell membrane. Next, interaction occurs between the HR-1 and HR-2 domains which bring the viral envelope close to the cell membrane (Russell et al, 2006). These domains are known to form a very stable bundle of six helices constituted by a trimeric coiled-coil structure in which three HR-I domains are linked with three HR-2 domains in an anti-parallel orientation. This conformation represents the post-fusion form of the F protein (Baker et al, 1999, Sergel-Germano et al, 2000, West et al, 2005).

The fusion protein F of PIV-5 and PIV-2 requires a HN protein deriving from the same viral type for there to be promotion of fusion (Yao et al, 1997). However, the precise nature of the interactions which exist between F and HN is still not properly known.

Nevertheless, several studies have shown that certain strains of PIV-5 and PIV-2 differ in their requirement for HN to trigger fusion.

As an example, Ito et al, 1997 describe two strains of "SV5" (PIV-5), namely W3A and WR, the F proteins of which differ by only three amino acids (residues 22, 443 and 516). The F protein of the W3A strain is capable of inducing fusion in an autonomous manner, i.e. in the absence of the HN protein, while the F protein of the WR strain is not capable thereof.

Ito et al, 1997 indicate that the fusogenic activity of the F protein of the WR strain can be re-established by replacing the amino acid in position 22 of this protein by the amino acid proline.

Ito et al, 2000 suggest that the amino acid E in position 132 and the amino acid A in position 290 of the F protein of the W3A and WR strains could be involved in the capacity of the F protein of these strains to be autonomous of the HN protein.

Paterson et al, 2000 indicate that the presence of the amino acid proline in position 22 of the F protein of the W3A strain, and the presence of the amino acid 443 of the F protein of the WR strain could increase the fusogenic capacity of these viral strains.

Russell et al, 2003 indicate that replacing the residues L447 and 1449 of the F protein of the strain W3A by aromatic amino acids could increase the fusogenic activity of the F protein of this viral strain.

Gardner and Dutch, 2007, indicate that the mutation 149A of the F protein of a wild type "SV5" (PIV-5) virus should have a pro-fusogenic effect.

Gardner et al, 2007, indicate that the mutation V402A of the F protein of a wild type "SV5" (PIV-5) virus should have a pro-fusogenic effect.

Concerning the protein PIV-2, there does not appear to be a prior art document which describes the introduction of mutation(s) into the sequence for the F protein of this virus, of the type to attempt to thereby increase the autonomy and fusogenic capacity.

Furthermore, there are many other viral proteins capable of fusion, such as the influenza proteins HA1/HA2, the rhabdovirus G protein, or the gp41/gp120 proteins of HIV.

Current knowledge concerning the fusogenicity capacities and autonomy of these various viral proteins is still very limited.

In any event, current knowledge concerning viral fusion proteins does not provide sufficient technical know-how to envisage effective medical and/or biotechnological applications.

SUMMARY OF THE INVENTION

The inventors have assumed that having available a fusion protein which was hyperfusogenic and which also exhibited substantial autonomy in its capacity for fusion could provide a solution to a certain number of medical and biotechnological situations.

The inventors have thus selectively selected the F protein of PIV-5 and/or PIV-2 from a series of other viral fusion proteins, such as the HA1/HA2 proteins from influenza, the G protein from rhabdovirus, or the gp41/gp120 proteins from HIV, for example.

They then constructed and produced mutant F proteins which are capable of fusogenicity in the absence of the HN protein.

The mutant proteins of the invention proved to have a high capacity for fusogenicity and high autonomy. They did not require the presence of the HN protein to induce cell fusion and the formation of syncytia.

The inventors also showed that it is possible to introduce into these mutant proteins a cleavage site which is different from that which the F protein presents in the natural state, and more particularly a tissue-specific cleavage site.

The inventors also propose medical (therapeutic, preventative, palliative, but also diagnostic) and/or biotechnological applications for the mutant proteins of the invention and/or products derived or following therefrom.

More particularly, the inventors propose the use of the mutant proteins of the invention or nucleic acids encoding them, to treat, prevent or mitigate, in vivo or ex vivo, diseases or dysfunctions for which it is desirable to induce or increase the formation of syncytia, such as cancers (more particularly metastatic cancers, preferably metastatic melanomas) or deficiencies in placental development.

The inventors further propose agents blocking the F protein of PIV-5 and/or PIV-2, such as antibodies, recombinant dendritic cells, antisense cells, siRNAs, nucleic acid aptamers, to treat, prevent or mitigate, in vivo or ex vivo, diseases or dysfunctions for which it is desired to inhibit or block the formation of syncytia, such as enveloped virus infections, allergies, auto-immune diseases or graft rejections.

The inventors further propose diagnostic means for detecting the excessive or, in contrast, insufficient formation of syncytia.

The inventors further propose different biotechnological means, especially for screening active principles capable of reducing the formation of syncytia.

The inventors further propose cancer cells, more particularly myelomas, which comprise a mutant protein of the invention. The inventors further propose hybridomas comprising a mutant protein of the invention. The cancer cells, more particularly myelomas, of the invention are capable of fusing with another cell, and more particularly with a B lymphocyte, without the use of polyethylene glycol (PEG), nor of electroporation, nor any other fusion-inducing means. The cancer cells, more particularly myelomas, of the invention are capable of autonomous fusion.

The hybridomas of the invention may be produced by fusion (of B lymphocytes to myelomas) which does not require the use of polyethylene glycol (PEG), nor of electroporation, nor of any other fusion-inducing means. The hybridomas of the invention may in fact be produced by employing at least one cancer cell, more particularly at least one myeloma of the invention.

The inventors further propose recombinant stem or progenitor cells which express a mutant protein of the invention, and their applications in the production of muscle fibres.

Other aspects of the invention will be described in the "detailed description" section below.

BRIEF DESCRIPTION OF THE FIGURES

The set of figures for the application as filed was filed in colour. It can be accessed by consulting the file at the Office.

FIG. 1A: reference sequence for the F protein of PIV-5 (SEQ ID NO: 31; sequence for the F protein of the WR isolate) and corresponding CDS sequence (SEQ ID NO: 30; nucleic acid sequence encoding the protein of SEQ ID NO: 31). The bold and underlined characters in the sequence of SEQ ID NO: 31 indicate the amino acids of positions:

22 (L),
49 (I),
132 (E, pre-existing mutation in this isolate),
147 (T),
158 (T),
290 (A, pre-existing mutation in this isolate),
402 (V),
443 (P, mutation theoretically pre-existing in this isolate),
447 (L),
449 (I), and
463 (A), FIG. 1B: reference sequence for the F protein of PIV-2 (SEQ ID NO: 33; sequence for the F protein of the Greer isolate) and corresponding CDS sequence (SEQ ID NO: 32; nucleic acid sequence encoding the protein of SEQ ID NO: 33).

The bold and underlined characters in the sequence of SEQ ID NO: 33, indicate the amino acids of positions:

24 (I),
53 (I),
133 (K),
151 (T),
162 (S),
294 (I),
406 (A),
428 (S),
439 (S),
445 (I),
474 (S).

FIG. 2 A: alignment of the F protein of PIV-5 (amino acids 4 to 529 of SEQ ID NO: 31) on that of PIV-2 (amino acids 8 to 533 of SEQ ID NO: 33): the protein identity is 47.7% between these two proteins. The consensus sequence resulting from this alignment is referenced as SEQ ID NO: 34.

FIG. 2B: amino acid(s) and mutation(s) in the PIV-2 F protein which correspond to those of the F protein of PIV-5.

Figure 3:
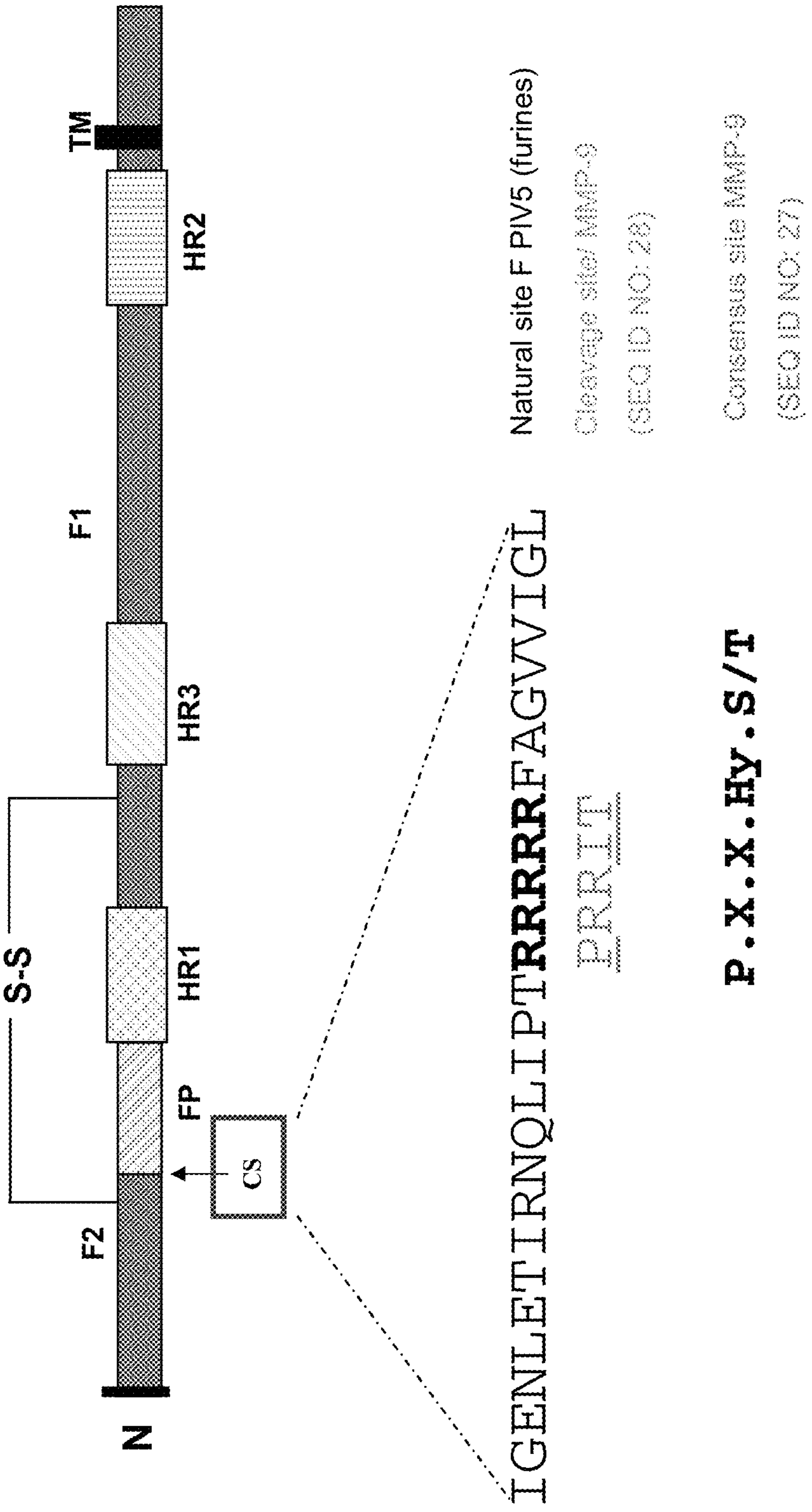

FIG. 3: illustration of the substitution of the natural cleavage site (SEQ ID NO: 23) of the F protein of PIV-5 by a tissue-specific cleavage site, in this case the site of an enzyme specifically expressed by metastatic tumour tissue, namely matrix metallo-protease 9 (MMP-9).

Consensus site of a MMP-9 site: sequence of SEQ ID NO: 27 (PXXhyS/T site where X=any amino acid and Hy=any hydrophobic amino acid, i.e. any amino acid selected from F, M, V, L, I).

Illustrative sequence for a MMP-9 site: sequence of SEQ ID NO: 28, sequence of SEQ ID NO: 29.

Figure 4:
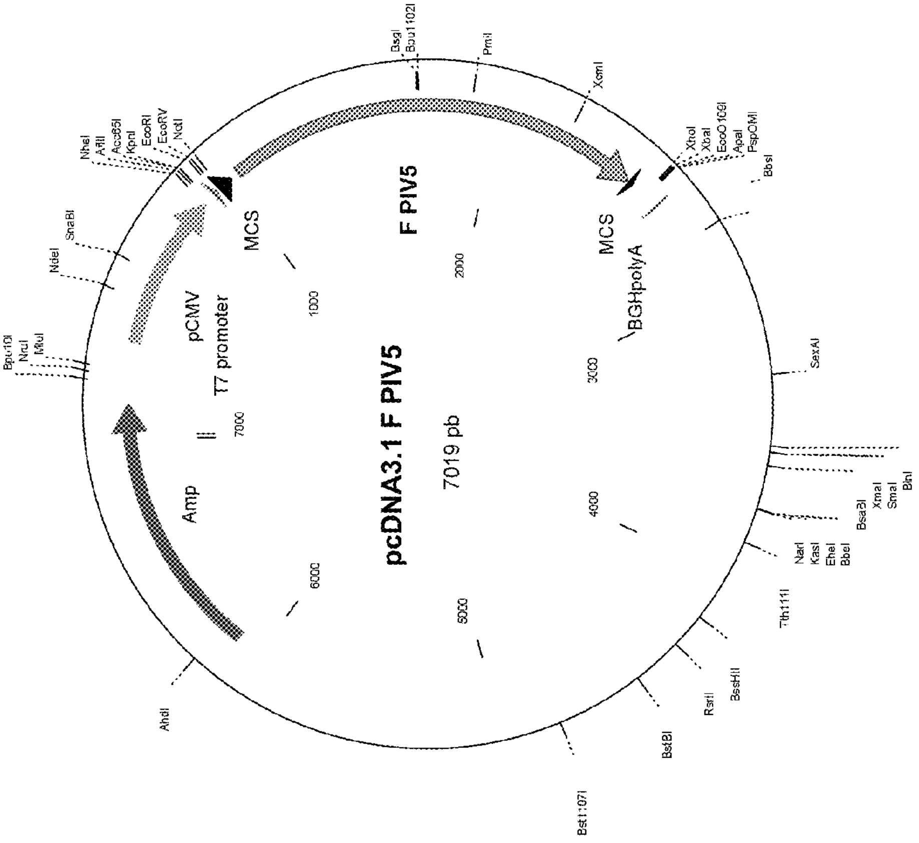
Figure 5A:
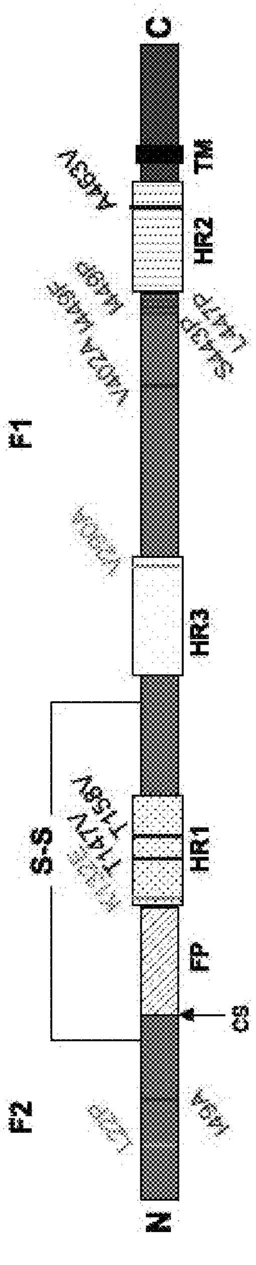
Figure 5B:
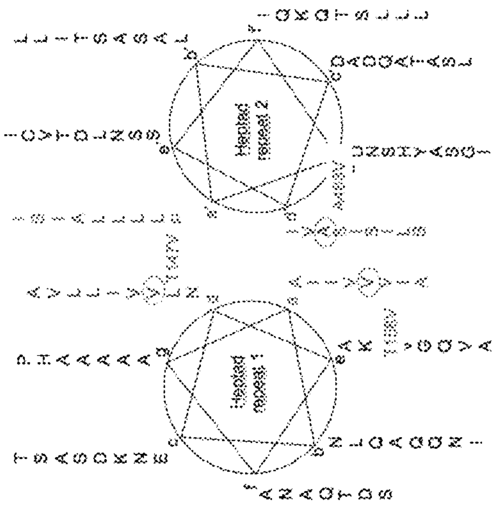
Figure 5D:
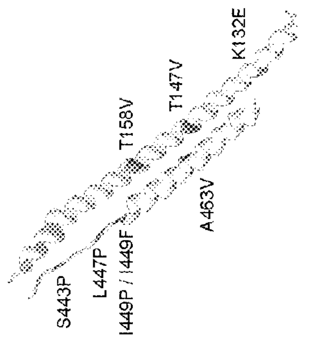
Figure 5C:
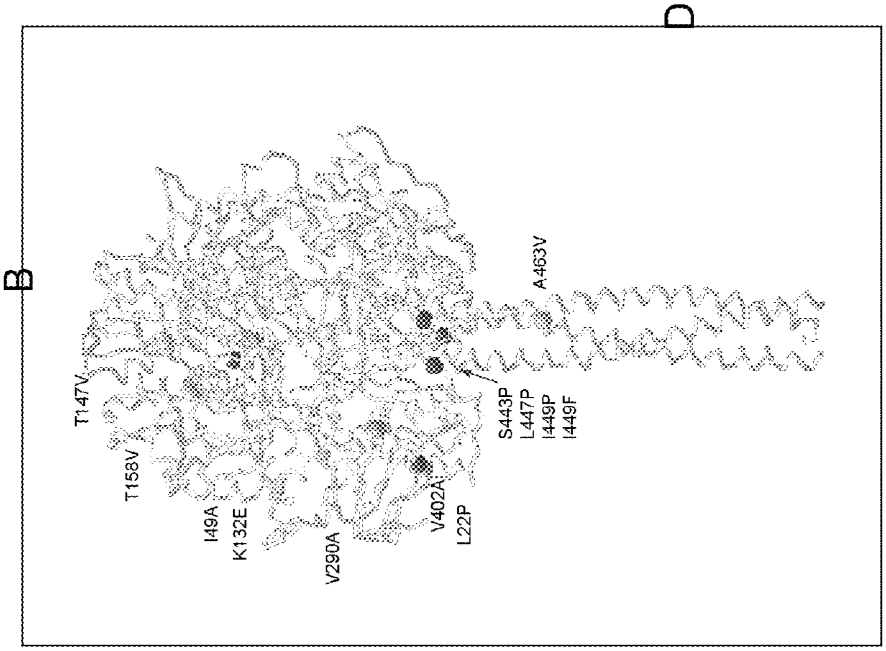

FIG. 4: structure of plasmid pcDNA3.1 onto which the sequence encoding the F protein of PIV-5 has been cloned.

Amp: ampicillin resistance gene pCMV: cytomegalovirus promoter

MCS: multiple cloning site

F PIV5: F protein of PIV-5

BGHpolyA: bovine growth hormone polyA.

FIGS. 5A, 5B, 5C, 5D: visualisation of mutations produced by the inventors in the F protein of PIV-5.

Figure 6A:
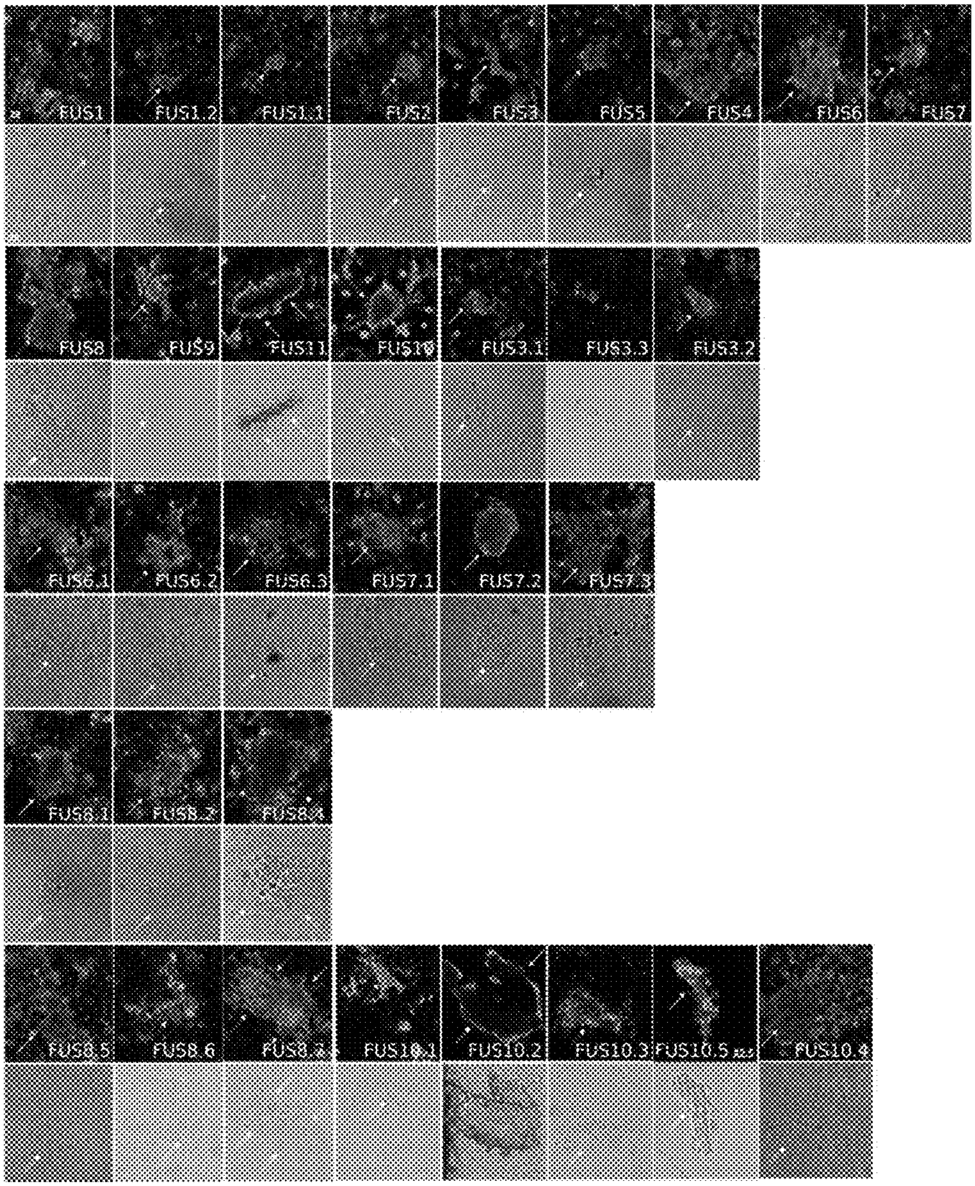

FIG. 6A: illustration of microscope observations carried out during semi-quantitative fusion tests (large panel of mutants produced by the inventors).

Figure 6B:
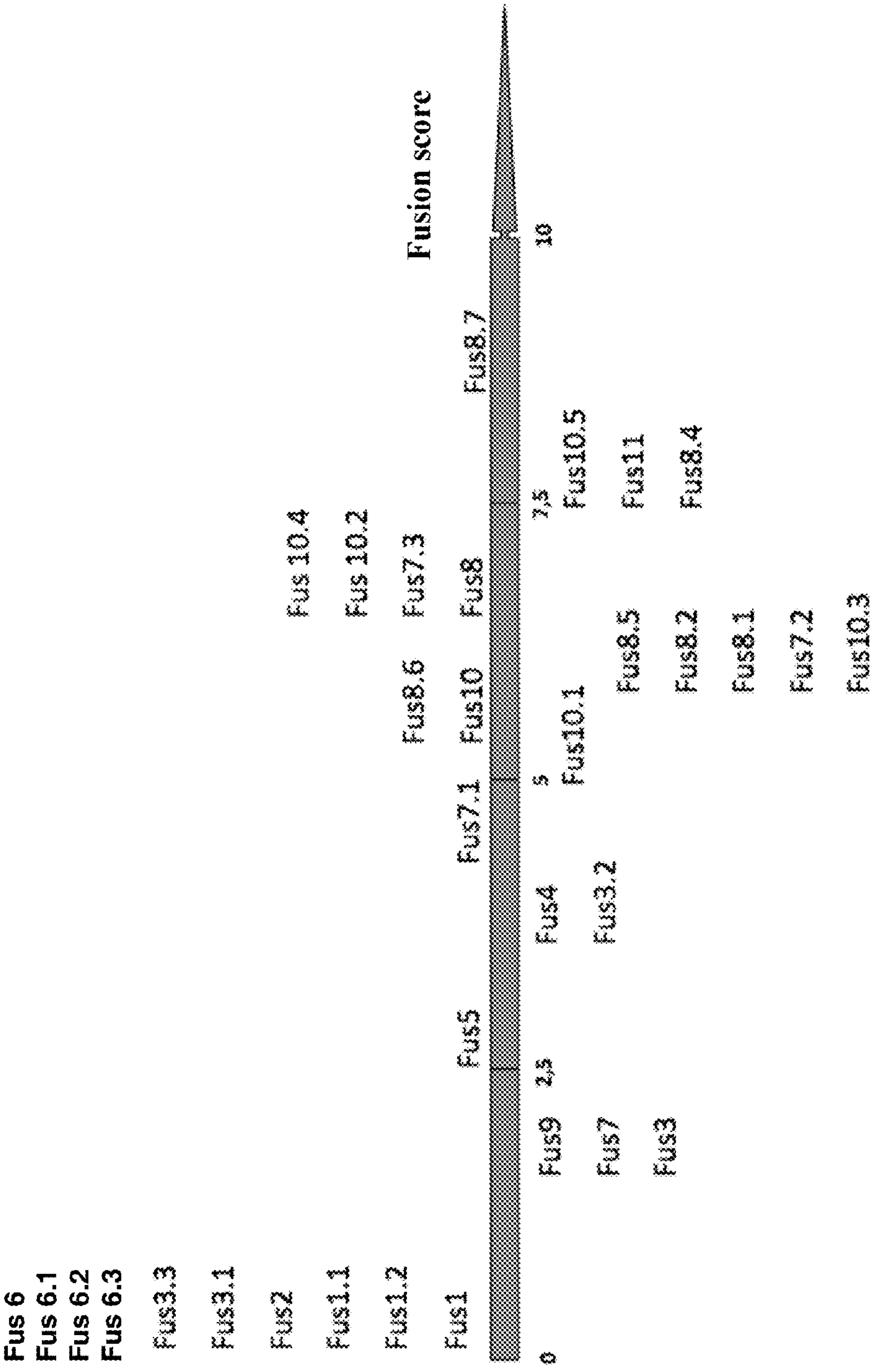

FIG. 6B: diagram presenting the fusion scores obtained after semi-quantitative fusion tests (large panel of mutants produced by the inventors).

Figure 7A:
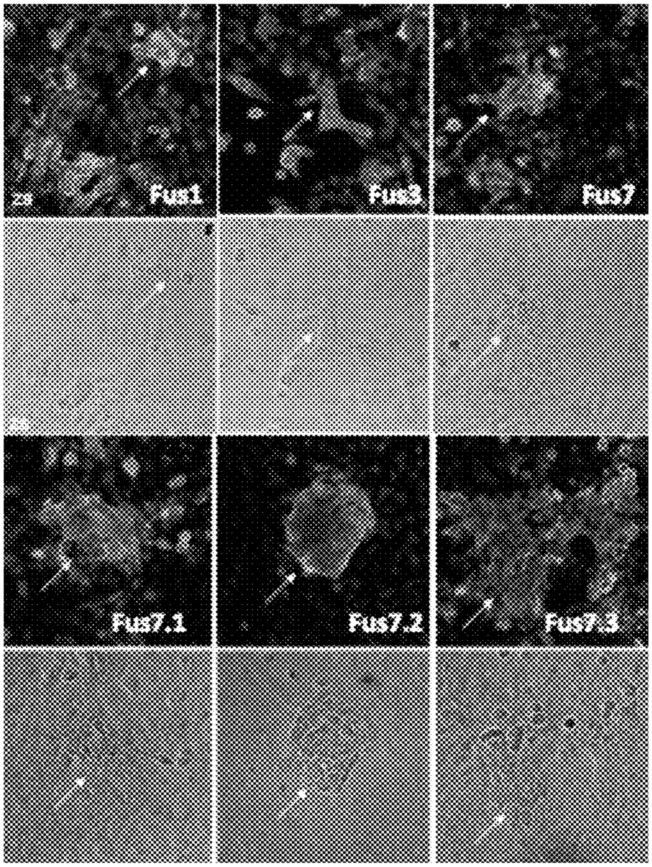

FIG. 7A: illustration of microscope observations carried out during semi-quantitative fusion tests (selection of mutants produced by the inventors).

Figure 7B:
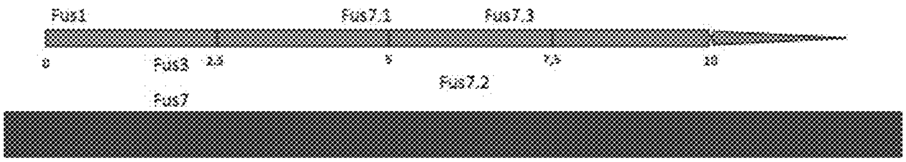

FIG. 7B: diagram presenting the fusion scores obtained after semi-quantitative fusion tests (selection of mutants produced by the inventors).

DETAILED DESCRIPTION

In the present application, the term "protein" includes the term "glycoprotein" in its scope. This is especially the case for the F and HN proteins which are in fact glycoproteins.

F Protein of PIV-5 and PIV-2 (Non-Mutant Protein):

A sequence for the F protein of PIV-5 is presented in FIG. 1A (protein sequence of SEQ ID NO: 31; coding nucleic acid sequence of SEQ ID NO: 30). It is the sequence for the WR isolate, which is a simian isolate. These sequences are those available from the Genbank database with accession number AB021962.

The sample of the WR isolate which the inventors received from the ATCC and which they used for the construction and the production of the mutant proteins described in the examples below do not, however, have the amino acid P in position 443 of the F protein (in contrast to that which was expected in view of the sequence available from Genbank), but rather the amino acid S. This alternative sequence for the F protein of the WR isolate is thus identical to the sequence of SEQ ID NO: 31, with the exception of the amino acid in position 443 which is S and not P. For the purposes of brevity, this alternative sequence will herein be denoted "SEQ ID NO: 31 with S at 443".

The sequence of SEQ ID NO: 31 and the alternative sequence "SEQ ID NO: 31 with S at 443", preferably the alternative sequence "SEQ ID NO: 31 with S at 443", act as reference sequence(s) for the F protein of PIV-5 in the context of the present patent application.

However, clearly, isolates other than the WR isolate exist, in particular:

- other simian isolates, such as the W3A isolate, for example;
- isolates from other non-human animals, such as:
  - canine isolates, for example the canine isolates CPI+, CPI−, H221, 78524, T1;
  - porcine isolates, for example the porcine isolate SER;
- isolates termed "human" isolates which are derived from samples taken from human beings but which have been cultured on animal cells (see introduction section above), such as the MIL isolate, the DEN isolate, the LN isolate, the MEL isolate and the isolate which, in WO 02 077211, is described as being a "cryptovirus".

The variations in the sequences for the F proteins of these various PIV-5 isolates are very slight.

A description of these variations is given by Chatziandreou et al, 2004, the contents of which, and more particularly Table 3 and the comments associated therewith in that article, are herewith incorporated into the present patent application by reference.

Table 3 of that article is reproduced here:

TABLE 1

(reproduced from the article by Chatziandreou et al, 2004):

| Strain | | | | | | | | | | | | | |
|---|---|---|---|---|---|---|---|---|---|---|---|---|---|
| W3A (SEQ ID NO: 35) | WR (SEQ ID NO: 31) | MIL (SEQ ID NO: 36) | DEN (SEQ ID NO: 37) | LN (SEQ ID NO: 38) | MEL (SEQ ID NO: 39) | cryptovirus (SEQ ID NO: 40) | CPI+ (SEQ ID NO: 41) | CPI− (SEQ ID NO: 42) | H221 (SEQ ID NO: 43) | 78524 (SEQ ID NO: 44) | T1 (SEQ ID NO: 45) | SER (SEQ ID NO: 46) | aa |
| G | | | | | | S | | | | | | | 2 |
| T | | I | I | I | I | | | | | | | | 3 |
| I | | | | | | | | | R | R | R | | 4 |
| F | | | | | | S | | | | | | | 7 |
| A | | | | | | | | | S | S | T | | 17 |
| S | | G | G | G | G | | | | | | | | 19 |
| P | L | | | | | | | | | | | | 22 |
| S | | | | | | | P | P | | | | | 71 |
| V | | | | | | | | | | | M | | 76 |
| N | | | | | | | | | Y | Y | Y | | 92 |
| E | | | | | | | K | K | K | K | K | K | 132 |
| A | | | | | | T | | | | | | | 134 |
| A | | | | | | | | | V | V | V | | 135 |
| A | | | | | | | | | | | | T | 149 |
| V | | | | | | I | | | | | | | 176 |
| I | | | | M | | | | | | | | | 271 |
| T | | | | | | | | A | | | | | 279 |
| A | | | | | | | | | | | V | | 290 |
| T | | | | | | | K | K | | | | | 307 |
| M | | | | | | I | I | I | I | I | I | I | 310 |
| M | | | | | R | | | | | | | | 346 |
| L | | | | F | | | | | | | | | 366 |
| V | | | | | | | | | | | | M | 370 |

TABLE 1-continued (reproduced from the article by Chatziandreou et al, 2004):

| Strain | | | | | | | | | | | | | |
|---|---|---|---|---|---|---|---|---|---|---|---|---|---|
| W3A (SEQ ID NO: 35) | WR (SEQ ID NO: 31) | MIL (SEQ ID NO: 36) | DEN (SEQ ID NO: 37) | LN (SEQ ID NO: 38) | MEL (SEQ ID NO: 39) | cryptovirus (SEQ ID NO: 40) | CPI+ (SEQ ID NO: 41) | CPI− (SEQ ID NO: 42) | H221 (SEQ ID NO: 43) | 78524 (SEQ ID NO: 44) | T1 (SEQ ID NO: 45) | SER (SEQ ID NO: 46) | aa |
| Y | | | | | | | | | F | F | | | 377 |
| M | | | | | | | I | I | | | | | 407 |
| Y | | | | | | H | H | H | | | | | 408 |
| N | | | | | | D | | | | | | | 417 |
| F | | | | | | | L | L | | | | | 420 |
| V | | | | | | | | | | | I | | 428 |
| S | | | | | | T | T | T | T | T | T | T | 438 |
| S | P | P | P | P | P | P | P | P | P | P | P | P | 443 |
| H | | | | | | | N | N | | | | | 451 |
| I | | | | | | | | | | | | M | 489 |
| L | | F | F | F | F | | | | | | | | 498 |
| L | | | | | | | S | S | | | | | 500 |
| V | | | | | | | A | A | | | | | 507 |
| K | | | | | | | R | R | | | | | 510 |
| V | A | A | A | A | A | A | A | A | A | A | A | T | 516 |
| K | | N | N | N | N | N | N | N | N | N | N | N | 529 |
| Stop | Stop | Q | | | | S | S | S | S | S | S | S | 530 |
| | | H | | | | | Y | Y | | | | | 533 |
| | | S | | | Stop | P | | | | | | | 535 |
| | | Q | | | | R | R | R | R | R | R | R | 536 |

aa: position of the amino acid

In Table 1 above, an empty box indicates that the F protein concerned has the same amino acid as the F protein of the W3A strain indicated in the left hand column. The amino acids for which their positions are not expressly listed in this table are of course identical to those which correspond to them in the sequence for the F protein of W3A. These amino acids are themselves identical to those which correspond to them in the sequence for the F protein of the WR isolate (see sequence of SEQ ID NO: 31).

Hence, the sequences for SEQ ID NO: 35 to 46 are the sequences which result from replacement in the sequence of SEQ ID NO: 31 of the amino acids indicated in Table 1 for each of these sequences (and, if appropriate, addition at the C-terminal portion to the sequence of SEQ ID NO: 31 of the amino acids indicated).

The F protein of the W3A isolate, as well as that of the other isolates mentioned above, has:

in position 147, the amino acid T;

in position 158, the amino acid T;

in position 447, the amino acid L; and in position 449, the amino acid I.

Thus, it will be seen that the W3A and WR isolates do not have the cytoplasmic extension which, in the other isolates, extends beyond position 529. Depending on the isolate concerned, this cytoplasmic extension contains two to seven amino acids.

It will also be seen that the sequences for the F proteins of these isolates vary by less than 5% (more particularly, a maximum of 3%) compared with the sequence for the F protein of the WR strain (without taking into account the cytoplasmic extension, i.e. by calculating this percentage from the length of the F protein of WR); see end of page 85 of the article by Chatziandreou et al, 2004.

A F protein of PIV-5 may thus consist of:

the sequence of SEQ ID NO: 31, or said alternative sequence “SEQ ID NO: 31 with S at 443”; or of a variant sequence for this sequence of SEQ ID NO: 31 or of this alternative sequence “SEQ ID NO: 31 with S at 443”; this variant sequence may be defined as:

being identical in size to that of SEQ ID NO: 31 or smaller by a maximum of 7 amino acids than that of SEQ ID NO: 31 or larger by a maximum of 7 amino acids than that of SEQ ID NO: 31 [said alternative sequence “SEQ ID NO: 31 with S at 443” is the same size as the sequence of SEQ ID NO: 31], preferably with a size identical to that of SEQ ID NO: 31 or larger by a maximum of 7 amino acids than that of SEQ ID NO: 31; and having a sequence identity of more than 95%, preferably at least 96%, more preferably at least 97%, with respect to the sequence of SEQ ID NO: 31 or to said alternative sequence “SEQ ID NO: 31 with S at 443” (this identity being calculated using the length of the sequence of SEQ ID NO: 31 or, if appropriate, of said alternative sequence “SEQ ID NO: 31 with S at 443”).

The variant sequences for the F protein of PIV-5 of SEQ ID NO: 31 in particular comprise the sequences for the F proteins of the isolates W3A, MIL, DEN, LN, MEL, cryptovirus, CPI+, CPI−, H221, 78524, T1 and SER mentioned above (see Table 1 above and article by Chatziandreou et al, 2004).

In similar manner, the sequence which in the present application acts as a reference for the PIV-2 F protein is the sequence for the Greer strain which is presented in FIG. 1B (protein sequence of SEQ ID NO: 33, coding nucleic acid sequence of SEQ ID NO: 32).

Clearly, there are PIV-2 isolates other than Greer isolates, such as the V98, V94 Toshiba isolates, for example.

The sequence for the F protein of these other PIV-2 isolates is very close to that of the Greer isolate, but has several small variations which are inter-isolate variations.

Hence, a PIV-2 F protein may thus consist of:

the sequence of SEQ ID NO: 33; or of a variant sequence for this sequence of SEQ ID NO: 33; this variant sequence may be defined as:

being identical in size to that of SEQ ID NO: 33 or smaller by a maximum of two amino acids than that of SEQ ID NO: 33 or larger by a maximum of two amino acids than that of SEQ ID NO: 33, preferably with a size identical to that of SEQ ID NO: 33, preferably being identical in size to that of SEQ ID NO: 33; and having a sequence identity of more than 95%, preferably at least 96%, more preferably at least 97%, with respect to the sequence of SEQ ID NO: 33 (this identity being calculated using the length of the sequence of SEQ ID NO: 33).

The consensus sequence (SEQ ID NO: 34) resulting from alignment of the sequence for the F protein of PIV-5 (SEQ ID NO: 31) on that of PIV-2 (SEQ ID NO: 33) is as follows and may be read in FIG. 2A. This consensus sequence may be re-written as follows:

```
                                 (SEQ ID NO: 34)
I----V------G--------L--IGVI----R-LMYYT-----FIVVKL-

P--------CNITS---YN-T--KLL-P—-ENL--I---------R-RF

AGVV-GLAALGVATAAQ-TAAVA-VKAN-NAAAI-NL---IQ-TN-AV-D

V-A------TAVQA-QD-IN------IT-A-C-A-DA-IGSILNLYLTEL

TTIFHNQITNPAL-P--IQALRILLGSTLP-V-E---NT----AELLSSG

LLTGQI------YMQM-I-I-PT----QP----IDL—-ISA----QEV--

Q-P-R--------Q-YPA—C--TPN-V-CRYN-----------CL-GNL--

CTF-P--G-FL-RF----G--YANC-S-LC-C—P-—V--Q--------

ID---C----LD---F-IT---N-TY----------I----PLD-

S------NKSL--A----A-S---------A-T---LS-1A-L-----

L----LL-----KL-------R--------H-,
```

the symbol “-” indicating that the F proteins of PIV-5 and of PIV-2 have different amino acids in this position.

This consensus sequence may also be formalised as follows:

```
                                 (SEQ ID NO: 34)
IXXXXVXXXXXXGXXXXXXXXLXXIGVIXXXXRXLMYYTXXXXXFIVVKL

XPXXXXXXXXCNITSXXXYNXTXXKLLXPXXENLXXIXXXXXXXXXRXRF

AGVVXGLAALGVATAAQXTAAVAXVKANXNAAAIXNLXXXIQXTNXAVXD

VXAXXXXXXTAVQAXQDXINXXXXXXITXAXCXAXDAXIGSILNLYLTEL

TTIFHNQITNPALXPVXIQALRILLGSTLPXVXEXXXNTXXXXAELLSSG

LLTGQIXXXXXXYMQMXIXIXPTXXXXQPXXXXIDLXXISAXXXXQEVXX

QXPXRXXXXXXXXQXYPAXXCXXTPNXVXCRYNXXXXXXXXXXXCLXGNL

XXCTFXPXXGXFLXRFXXXXGXXYANCXSXLCXCXXPXXVXXQXXXXXXX

XIDXXXCXXXXLDXXXFXITXXXNXTYXXXXXXXXXXIXXXXPLDXSXXX

XXXNKSLXXAXXXXAXSXXXXXXXXXAXTXXXLSXIAXLXXXXXLXXXXL

LXXXXXKLXXXXXXXRXXXXXXXXHX,
```

where X=any amino acid.

The sequence for the F protein of the WR isolate of PIV-5 is the sequence of SEQ ID NO: 34 preceded by the amino acids MGT at the N-terminal end (see FIGS. 1A and 2A).

The sequence for the F protein of the Greer isolate of PIV-2 is the sequence of SEQ ID NO: 34, preceded by the amino acids MHHLHPM (SEQ ID NO: 86) at the N-terminal end and followed by the amino acids ENPAFFSKNNHGNIYGIS (SEQ ID NO: 87) at the C-terminal end (see FIGS. 1B and 2A).

The sequence for the F proteins of PIV-5 and PIV-2 may be considered to be a sequence comprising the sequence of SEQ ID NO: 34, preferably to be the sequence for a F protein of the PIV virus which comprises the sequence of SEQ ID NO: 34. More particularly, the sequence for the F proteins of PIV-5 and PIV-2 may be considered to be:

a) the sequence of SEQ ID NO: 34:

preceded by 3 to 7 amino acids at the N-terminal end, more particularly by 3 amino acids (such as MGT) or by 7 amino acids (such as MHHLHPM) at the N-terminal end; and optionally followed by 18 amino acids at the C-terminal end, more particularly the amino acids ENPAFFSKNNHGNIYGIS at the C-terminal end; or b) a variant sequence for the sequence described in a) above, said variant sequence being:

either:

i. with a size identical to that of SEQ ID NO: 31 or smaller by a maximum of 7 amino acids than that of SEQ ID NO: 31 or larger by a maximum of 7 amino acids than that of SEQ ID NO: 31, preferably with a size identical to that of SEQ ID NO: 31 or larger by a maximum of 7 amino acids than that of SEQ ID NO: 31; and ii. having a sequence identity of more than 95%, preferably at least 96%, more preferably at least 97%, with respect to the sequence of SEQ ID NO: 31 or to said alternative sequence “SEQ ID NO: 31 with S at 443” (this identity being calculated using the length of the sequence of SEQ ID NO: 31 or, if appropriate, of said alternative sequence “SEQ ID NO: 31 with S at 443”);

or:

i. with a size identical to that of SEQ ID NO: 33 or smaller by a maximum of two amino acids than that of SEQ ID NO: 33 or larger by a maximum of two amino acids than that of SEQ ID NO: 33, preferably with a size identical to that of SEQ ID NO: 33; and ii. having a sequence identity of more than 95%, preferably at least 96%, more preferably at least 97%, with respect to the sequence of SEQ ID NO: 33 (this identity being calculated using the length of the sequence of SEQ ID NO: 33).

Mutant Proteins of the Invention:

The present application relates to a mutant protein, the amino acid sequence for which comprises a sequence which is derivable from that of the F protein of a PIV-5 or PIV-2 virus:

by replacement:

of the amino acid which, in the sequence of said PIV-5 F protein, is in position 22, or which, in the sequence of said PIV-2 F protein, is in position 24, by the amino acid P (mutation 22P in the F of PIV-5; mutation 24P in the F of PIV-2); and of the amino acid which, in the sequence of said PIV-5 F protein, is in position 132, or which, in the sequence of said PIV-2 F protein, is in position 133 (mutation 132E in the F of PIV-5; mutation 133E in the F of PIV-2), by the amino acid E; and of the amino acid which, in the sequence of said PIV-5 F protein, is in position 290, or which, in the sequence of said PIV-2 F protein, is in position 294, by the amino acid A (mutation 290A in the F of PIV-5; mutation 294A in the F of PIV-2); and of the amino acid which, in the sequence of said PIV-5 F protein, is in position 447, or which, in the sequence of said PIV-2 F protein, is in position 445, by the amino acid P (mutation 447P in the F of PIV-5; mutation 445P in the F of PIV-2);

and by replacement:

of the amino acid which, in the sequence of said PIV-5 F protein, is in position 147, or which, in the sequence of said PIV-2 F protein, is in position 151, by a hydrophobic amino acid selected from V, I, L, preferably V (mutation 147Hy in the F of PIV-5; mutation 151Hy in the F of PIV-2); and/or of the amino acid which, in the sequence of said PIV-5 F protein, is in position 158, or which, in the sequence of said PIV-2 F protein, is in position 162, by a hydrophobic amino acid selected from V, I, L, preferably V (mutation 158Hy in the F of PIV-5; mutation 162Hy in the F of PIV-2);

and optionally:

by substitution of the native (or natural) cleavage site of said F protein by another enzymatic cleavage site, and/or by insertion into said F protein of an enzymatic cleavage site other than the native (or natural) cleavage site of said F protein; and/or by deletion of a C-terminal portion of said F protein, said C-terminal portion extending in the N-terminal direction from the last amino acid at the C-terminal end of the protein, but without extending beyond the HR2 domain of said F protein.

Said amino acid positions are calculated with respect to the sequence for the precursor form (F0) of said F protein (i.e. the sequence for the F protein before cleaving), counting the positions from the N-terminal end to the C-terminal end.

The positions indicated in the PIV-2 F protein are the positions which correspond to those indicated in the F protein of PIV-5: see FIG. 2B, giving the table for correspondence of positions.

The sequence of said F protein of the PIV-5 or PIV-2 virus is as defined above. Thus, it may in particular be defined as comprising the sequence of SEQ ID NO: 34 (consensus sequence for the F proteins of PIV-5 and PIV-2).

Mutant Protein of PIV-5F Protein:

In accordance with one aspect of the invention, a mutant protein of the invention comprises a sequence which is derivable from that of the F protein of a PIV-5 virus:

the sequence of SEQ ID NO: 31 (sequence for the F protein of the WR isolate of PIV-5 presented in FIG. 1A), or of said alternative sequence "SEQ ID NO: 31 with S at 443"; or of a variant sequence for this sequence of SEQ ID NO: 31 or of said alternative sequence "SEQ ID NO: 31 with S at 443", this variant sequence:

being identical in size to that of SEQ ID NO: 31 (i.e. consisting of 529 amino acids), or being of a size larger by a maximum of 7 amino acids than that of SEQ ID NO: 31 (i.e. consisting of 530, 531, 532, 533, 534, 535 or 536 amino acids), or being of a size smaller by a maximum of 7 amino acids than that of SEQ ID NO: 31 (i.e. consisting of 522, 523, 524, 525, 526, 527 or 528 amino acids); and having a sequence identity of more than 95%, preferably at least 96%, more preferably at least 97%, with respect to the sequence of SEQ ID NO: 31 or to said alternative sequence "SEQ ID NO: 31 with S at 443", this identity being calculated using the length of the sequence of SEQ ID NO: 31 or (if appropriate) of said alternative sequence "SEQ ID NO: 31 with S at 443".

Preferably, the sequence of said F protein of PIV-5 consists of:

the sequence of SEQ ID NO: 31 (sequence for the F protein of the WR isolate of PIV-5 presented in FIG. 1A), or said alternative sequence "SEQ ID NO: 31 with S at 443"; or of a variant sequence for this sequence of SEQ ID NO: 31 or of said alternative sequence "SEQ ID NO: 31 with S at 443", this variant sequence:

being identical in size to that of SEQ ID NO: 31 (i.e. consisting of 529 amino acids), or being of a size larger by a maximum of 7 amino acids than that of SEQ ID NO: 31 (i.e. consisting of 530, 531, 532, 533, 534, 535 or 536 amino acids); and having a sequence identity of more than 95%, preferably at least 96%, more preferably at least 97%, with respect to the sequence of SEQ ID NO: 31 or to said alternative sequence "SEQ ID NO: 31 with S at 443", this identity being calculated using the length of the sequence of SEQ ID NO: 31, or, if appropriate, of said alternative sequence "SEQ ID NO: 31 with S at 443".

Particular examples of such variant sequences comprise the sequence for the F protein of one of the W3A, MIL, DEN, LN, MEL, cryptovirus, CPI+, CPI−, H221, 78524, T1 and SER isolates presented in Table 1 in the present application (see above), i.e. one of the sequences of SEQ ID NO: 35 to 46.

Preferably, the sequence of said F protein of PIV-5 consists of the sequence of SEQ ID NO: 31 (sequence for the F protein of the WR isolate of PIV-5 presented in FIG. 1A), or of said alternative sequence "SEQ ID NO: 31 with S at 443", highly preferably in said alternative sequence "SEQ ID NO: 31 with S at 443".

Preferably, said sequence which is derivable from that of said F protein of PIV-5 is derivable from this F protein sequence by at least said mutations 22P, 132E, 290A, 447P and 158Hy mentioned above.

Preferably, said sequence which is derivable from that of said F protein of PIV-5 is derivable from this F protein sequence by at least said mutations 22P, 132E, 290A, 447P and 147Hy mentioned above.

Preferably, said sequence which is derivable from that of said F protein of NV-5 is derivable from this F protein sequence by at least said mutations 22P, 132E, 290A, 447P, 147Hy and 158Hy mentioned above.

Said sequence derivable from that of the F protein of PIV-5 does not have to comprise a mutation other than the mutations 22P, 132E, 290A, 447P and 147Hy/158Hy mentioned above, with respect to said F protein sequence for PIV-5.

Alternatively, said sequence derivable from that of the F protein of PIV-5 may be derivable from this F protein sequence by said mutations 22P, 132E, 290A, 447P and 147Hy1158FHy mentioned above and by at least one mutation other than these mutations 22P, 132E, 290A, 447P mentioned above, preferably by:

at least one pre-fusion mutation selected from:

replacement of the amino acid in position 49 by the amino acid A;

replacement of the amino acid in position 402 by the amino acid A;

replacement of the amino acid in position 443 by the amino acid P;

replacement of the amino acid in position 449 by the amino acid P;

and/or by at least one post-fusion mutation selected from:

replacement of the amino acid in position 463 by a hydrophobic amino acid.

Preferably, said sequence which is derivable from that of said F protein of PIV-5 is derivable from this F protein sequence by said mutations 22P, 132E, 290A, 447P and 147Hy/158Hy mentioned above, and by:

at least one pre-fusion mutation selected from:
  replacement of the amino acid in position 49 by the amino acid A;
  replacement of the amino acid in position 402 by the amino acid A;

and/or by at least one post-fusion mutation selected from:
  replacement of the amino acid in position 463 by a hydrophobic amino acid.

Preferably, said sequence which is derivable from that of said F protein of PIV-5 is derivable from this F protein sequence by said mutations 22P, 132E, 290A, 447P and 147Hy/158Hy mentioned above, and by at least one post-fusion mutation selected from:

replacement of the amino acid in position 463 by a hydrophobic amino acid.

Said hydrophobic amino acid selected to replace the amino acid in position 463 is advantageously selected from V, I, L, preferably V.

TABLE 4 selection of mutant proteins of the invention (mutant proteins of F protein of PIV-5)

| Fus No In parentheses: nature of the post-fusion mutation(s) over the three mutations for autonomy (22P, 132E, 290A) and the pre-fusion mutation 447P | Fusion score (see FIG. 6B) | SEQ ID NO: |
|---|---|---|
| 7.1 (147V) | approx 5 | 62 |
| 7.2 (158V) | approx 6.5 | 63 |
| 7.3 (147V et 158V) | approx 7 | 64 |

The mutations indicated in Table 4 may be introduced into the F protein of any PIV-5 isolate, i.e. the WR isolate or a variant isolate. More particularly, they may thus be introduced into the F protein sequence of SEQ ID NO: 31 presented in FIG. 1A (F protein of WR available from Genbank database with accession number AB021962).

As indicated above, the sample of the WR isolate which the inventors received from the ATCC and which they used to construct and produce the mutant proteins described in the examples below did not, however, have the amino acid P in position 443 of the F protein (in contrast to that which was expected in view of the sequence available from Genbank), but rather the amino acid S. The mutations indicated in Table 4 may thus be introduced into said alternative sequence "SEQ ID NO: 31 with S at 443" (SEQ ID NO: 62, 63, 64).

Mutant Protein of PIV-2 F Protein;

In accordance with another aspect of the invention, a mutant protein of the invention comprises a sequence which is derivable from that of the F protein of a PIV-2 virus.

The sequence for said PIV-2 F protein is as defined above. In particular, it may consist of the sequence of SEQ ID NO: 33 (sequence for the F protein of the Greer isolate of PIV-2 presented in FIG. 1B); or of
a variant sequence for this sequence of SEQ ID NO: 33, this variant sequence:
  being identical in size to that of SEQ ID NO: 33 (i.e. consisting of 551 amino acids), or being of a size larger by a maximum of 2 amino acids than that of SEQ ID NO: 33 (i.e. consisting of 552 or 553 amino acids), or being of a size smaller by a maximum of 2 amino acids than that of SEQ ID NO: 33 (i.e. consisting of 549 or 550 amino acids); and
  having a sequence identity of more than 95%, preferably at least 96%, more preferably at least 97%, with respect to the sequence of SEQ ID NO: 33, this identity being calculated using the length of the sequence of SEQ ID NO: 33.

Preferably, the sequence of said F protein of PIV-2 consists of:

the sequence of SEQ ID NO: 33 (sequence for the F protein of the Greer isolate of PIV-2 presented in FIG. 1B); or of
a variant sequence for this sequence of SEQ ID NO: 33, this variant sequence:
  being identical in size to that of SEQ ID NO: 33 (i.e. consisting of 551 amino acids), or being of a size larger by a maximum of 2 amino acids than that of SEQ ID NO: 33 (i.e. consisting of 552 or 553 amino acids); and
  having a sequence identity of more than 95%, preferably at least 96%, more preferably at least 97%, with respect to the sequence of SEQ ID NO: 33, this identity being calculated using the length of the sequence of SEQ ID NO: 33.

More preferably, the sequence of said F protein of PIV-2 consists of:

the sequence of SEQ ID NO: 33 (sequence for the F protein of the Greer isolate de PIV-2 presented in FIG. 1B); or of
a variant sequence for this sequence of SEQ ID NO: 33, this variant sequence:
  being identical in size to that of SEQ ID NO: 33 (i.e. consisting of 551 amino acids); and
  having a sequence identity of more than 95%, preferably at least 96%, more preferably at least 97%, with respect to the sequence of SEQ ID NO: 33, this identity being calculated using the length of the sequence of SEQ ID NO: 33.

Highly preferably, the sequence of said F protein consists of the sequence of SEQ ID NO: 33 (sequence for the F protein of the Greer isolate of PIV-2 presented in FIG. 1B).

Preferably, said sequence which is derivable from that of said PIV-2 F protein is derivable from this F protein sequence by at least said mutations 24P, 133E, 294A, 445P and 162Hy mentioned above.

Preferably, said sequence which is derivable from that of said F protein of PIV-2 is derivable from this F protein sequence by at least said mutations 24P, 133E, 294A, 445P and 151Hy mentioned above.

Preferably, said sequence which is derivable from that of said F protein of PIV-2 is derivable from this F protein sequence by at least said mutations 24P, 133E, 294A, 445P, 162Hy and 151Hy mentioned above.

Said sequence which is derivable from that of the F protein of PIV-5 does not have to comprise a mutation other than the mutations 24P, 133E, 294A, 445P and 151Hy/162Hy mentioned above, with respect to said F protein sequence for PIV-2.

Alternatively, said sequence derivable from that of the PIV-2 F protein may be derivable from this F protein sequence by said mutations 24P, 133E, 294A, 445P and 151Hy/162Hy mentioned above and by at least one mutation other than these mutations 24P, 133E, 294 A, 445P mentioned above, preferably by:

at least one pre-fusion mutation selected from:
- replacement of the amino acid in position 53 by the amino acid A;
- replacement of the amino acid in position 406 by the amino acid A;
- replacement of the amino acid in position 428 by the amino acid P;
- replacement of the amino acid in position 439 by the amino acid P;

and/or by at least one post-fusion mutation selected from:
- replacement of the amino acid in position 474 by a hydrophobic amino acid.

Preferably, said sequence which is derivable from that of said F protein of the PIV-2 is derivable from this F protein sequence by said mutations 24P, 133E, 294A, 445P and 151Hy/162Hy mentioned above, and by:

at least one pre-fusion mutation selected from:
- replacement of the amino acid in position 53 by the amino acid A;
- replacement of the amino acid in position 406 by the amino acid A;

and/or by at least one post-fusion mutation selected from:
- replacement of the amino acid in position 474 by a hydrophobic Preferably, said sequence which is derivable from that of said F protein of the PIV-2 is derivable from this F protein sequence by said mutations 24P, 133E, 294A, 445P and 151Hy/162Hy mentioned above, and by at least one post-fusion mutation selected from:
- replacement of the amino acid in position 474 by a hydrophobic amino acid.

Said hydrophobic amino acid selected in replacement of the amino acid in position 474 is advantageously selected from V, I, L, preferably V.

TABLE 5 selection of mutant proteins of the invention (mutant proteins of PIV-2 F protein)

| Nature of post-fusion mutation(s) over the three autonomy mutations (24P, 133E, 294A) and the pre-fusion mutation 445P | SEQ ID NO: |
|---|---|
| 151V | 88 |
| 162V | 89 |
| 151V and 162V | 90 |

The mutations indicated in Table 5 may be introduced into the F protein of any PIV-2 isolate, i.e. the Greer isolate or a variant isolate. Thus, more particularly they may be introduced into the F protein sequence of SEQ ID NO: 33 presented in FIG. 1B (F protein of Greer; SEQ ID NO: 88 to 90).

```
                                                      SEQ ID NO: 88
MHHLHPMIVC IFVMYTGIVG SDAPAGDQLL NIGVIQSKIR SLMYYTDGGA SFIVVKLLPN  60

LPPSNGTCNI TSLDAYNVTL FKLLTPLIEN LSKISTVTDT KTRQKRFAGV VVGLAALGVA 120

TAAQITAAVA IVEANANAAA INNLASSIQS VNKAVSDVID ASRTIATAVQ AIQDRINGAI 180

VNGITSASCR AHDALIGSIL NLYLTELTTI FHNQITNPAL TPLSIQALRI LLGSTLPIVI 240

ESKLNTNFNT AELLSSGLLT GQIISISPMY MQMLIQINVP TFIMQPGAKV IDLAAISANH 300

KLQEVVVQVP NRILEYANEL QNYPANDCVV TPNSVFCRYN EGSPIPESQY QCLRGNLNSC 360

TFTPIIGNFL KRFAFANGVL YANCKSLLCR CADPPHVVSQ DDTQGISIID IKRCSEMMLD 420

TFSFRITSTF NATYVTDFSM INANPVHLSP LDLSNQINSI NKSLKSAEDW IADSNFFANQ 480

ARTAKTLYSL SAIALILSVI TLVVVGLLIA YIIKLVSQIH QFRSLAATTM FHRENPAFFS 540

KNNHGNIYGI S                                                     551

                                                      SEQ ID NO: 89
MHHLHPMIVC IFVMYTGIVG SDAPAGDQLL NIGVIQSKIR SLMYYTDGGA SFIVVKLLPN  60

LPPSNGTCNI TSLDAYNVTL FKLLTPLIEN LSKISTVTDT KTRQKRFAGV VVGLAALGVA 120

TAAQITAAVA IVEANANAAA INNLASSIQS TNKAVSDVID AVRTIATAVQ AIQDRINGAI 180

VNGITSASCR AHDALIGSIL NLYLTELTTI FHNQITNPAL TPLSIQALRI LLGSTLPIVI 240

ESKLNTNFNT AELLSSGLLT GQIISISPMY MQMLIQINVP TFIMQPGAKV IDLAAISANH 300

KLQEVVVQVP NRILEYANEL QNYPANDCVV TPNSVFCRYN EGSPIPESQY QCLRGNLNSC 360

TFTPIIGNFL KRFAFANGVL YANCKSLLCR CADPPHVVSQ DDTQGISIID IKRCSEMMLD 420

TFSFRITSTF NATYVTDFSM INANPVHLSP LDLSNQINSI NKSLKSAEDW IADSNFFANQ 480

ARTAKTLYSL SAIALILSVI TLVVVGLLIA YIIKLVSQIH QFRSLAATTM FHRENPAFFS 540

KNNHGNIYGI S                                                     551

                                                      SEQ ID NO: 90
MHHLHPMIVC IFVMYTGIVG SDAPAGDQLL NIGVIQSKIR SLMYYTDGGA SFIVVKLLPN  60

LPPSNOTCNI TSLDAYNVTL FKLLTPLIEN ISKISTVTDT KTRQKRFAGV VVGLAALGVA 120
```

-continued

```
TAAQITAAVA IVEANANAAA INNLASSIQS VNKAVSDVID AVRTIATAVQ AIQDRINGAI 180

VNGITSASCR AHDALIGSIL NLYLTELTTI FHNQITNPAL TPLSIQALRI LIGSTLPIVI 240

ESKLNTNFNT AELLSSGLLT GQIISISPMY MQMLIQINVP TFIMQPGAKV IDLAAISANH 300

KLQEVVVQVP NRILEYANEL QNYPANDCVV TPNSVFCRYN EGSPIPESQY QCLRGNLNSC 360

TFTPIIGNFL KRFAFANGVL YANCKSLLCR CADPPHVVSQ DDTQGISIID IKRCSEMMLD 420

TFSFRITSTF NATYVTDFSM INANPVHLSP LDLSNQINSI NKSLKSAEDW IADSNFFANQ 480

ARTAKTLYSL SAIALILSVI TLVVVGLLIA YIIKLVSQIH QFRSLAATTM FHRENPAFFS 540

KNNHGNIYGI S                                                     551
```

Cleavage Site:

In accordance with the present invention, a mutant protein of the invention may comprise a sequence which is derivable from that of the F protein of a PIV-5 or PIV-2 virus by:

- the mutations mentioned above; and further by
- substitution of the native cleavage site of said F protein by another enzymatic cleavage site, and/or by insertion into said F protein of an enzymatic cleavage site other than the native cleavage site of this F protein, preferably by substitution of the native cleavage site of said F protein by another enzymatic cleavage site.

The cleavage site of a PIV-5 or PIV-2 F protein is the cleavage site of two subunits (F1 and F2) of this F protein.

In the native form of the F protein of PIV-5 and PIV-2, this cleavage site is a site cleaved by furines.

In the native form of the F protein of PIV-5, this cleavage site consists of the sequence RRRRR (SEQ ID NO: 23). It is in positions 98 to 102 of the native form of the F protein of PIV-5 (see FIG. 1A). An example of a fragment of a PIV-5 F protein sequence comprising the native (or natural) cleavage site of the F protein of PIV-5 is:

IGENLETIRNQLIPTRRRRRFAGVVIGL. (SEQ ID NO: 24)

In the native form of the PIV-2 F protein, the cleavage site consists of the sequence KTRQKR (SEQ ID NO; 25). It is in positions 101 to 106 of the native form of the PIV-2 F protein (see FIG. 1B). An example of a fragment of a PIV-2 F protein sequence comprising the native (or natural) cleavage site of the F protein of PIV-2 is (SEQ ID NO: 26)
LTPLIENLSKISTVTDTKTRQKRFAGVVVGLAALGVA.

Preferably, said cleavage site other than the native cleavage site is a tissue-specific cleavage site.

Preferably, said cleavage site other than the native cleavage site is a cleavage site for an enzyme specifically expressed by tumour tissue or tissues, highly preferably a cleavage site for an enzyme specifically expressed by metastatic tissue or tissues.

As an example, said cleavage site other than the native cleavage site may be a cleavage site for a metallo-protease, such as the cleavage site for matrix metallo-protease 9 (MMP-9); see Example 2 below.

A cleavage site for matrix metallo-protease 9 (MMP-9) may comprise or consist of the sequence PXXHy SIT (SEQ ID NO: 27) where X=any amino acid, and where Hy=any hydrophobic amino acid (i.e. any amino acid selected from F, M, V, L, I).

As an example, a cleavage site for matrix metallo-protease 9 (MMP-9) may comprise or consist of the sequence PRRIT (SEQ ID NO: 28) and/or the sequence

IGENLETIRNQLIPTPRRITFAGVVIGL. (SEQ ID NO: 29)

Nucleic Acids of the Invention:

The present application also relates to a nucleic acid, DNA or RNA, which encodes a mutant protein in accordance with the invention (in accordance with the universal genetic code and allowing for degeneracy of that code), and to a complementary nucleic acid of such a nucleic acid (perfectly complementary nucleic acid of the same length).

Such nucleic acids derive from the sequence of SEQ ID NO: 30 (sequence encoding the native PIV-5 F protein), or of an alternative sequence coding for said alternative sequence “SEQ ID NO: 31 with S at 443”, or of a variant sequence encoding a variant F protein, or even of the sequence of SEQ ID NO: 32 (sequence encoding the native PIV-2 F protein) or of a variant sequence encoding a variant F protein.

Vectors of the Invention:

The present application also relates to a nucleic acid vector, more particularly to a transfection, transduction or transformation vector, comprising at least one nucleic acid in accordance with the invention.

Advantageously, such a vector may be an expression vector.

Preferably, it is a vector allowing expression of said at least one nucleic acid in an animal cell (non-human animal cell and/or human cell), more preferably:

- in a human cell, advantageously in a pathological human cell, more particularly a human tumour cell, more preferably a metastatic melanoma cell; or
- in a placental cell.

Such an expression vector may advantageously be an adenoviral vector.

Said adenoviral vector may comprise elements for regulating the expression of said nucleic acid, preferably a promoter, allowing expression of said nucleic acid in tumour cells, preferably in metastatic cells, more preferably in metastatic melanoma cells.

Preferably, this expression is specific. Advantageously, this expression is sufficiently specific to allow the expression of said nucleic acid in said tumour or metastatic cells, without there being significant expression in non-tumour (or non-metastatic) cells.

Advantageously, such an adenoviral vector is an oncolytic adenoviral vector.

Alternatively, an expression vector of the invention may be an adenoviral vector which comprises elements for regulating the expression of said nucleic acid, preferably a promoter, allowing expression of said nucleic acid in placental cells, preferably in pathological placental cells which have insufficient fusogenicity.

Preferably, this expression is specific. Advantageously, this expression is sufficiently specific to allow the expression of said nucleic acid in said placental cells, without there being significant expression in non-placental cells.

A vector of the invention may alternatively or complementarily be a vector allowing the insertion of said at least one nucleic acid into the genome of an animal cell (non-human animal cell and/or human cell), more preferably a human cell, advantageously a pathological human cell, more particularly a human tumour cell, preferably a metastatic human cell, more preferably in metastatic melanoma cells. Such a vector is more particularly intended for the gene therapy of tumours, particularly metastatic tumours, more particularly metastatic melanomas.

The present application also relates to a vector which comprises at least one nucleic acid of the invention, and which allows the insertion of said at least one nucleic acid into the genome of an animal cell (non-human animal cell and/or human cell), more preferably a human cell, advantageously a placental cell, preferably a human placental cell. Such a vector is more particularly intended for the gene therapy of diseases or conditions involving deficient placental development.

Cells of the Invention:

The present application also relates to a cell which comprises at least one mutant protein in accordance with the invention, and/or at least one nucleic acid, DNA or RNA, in accordance with the invention, and/or at least one vector in accordance with the invention.

Such a cell may be a human cell or a non-human animal cell.

Preferably, such a cell is a tumour cell, preferably a metastatic cell, more preferably a metastatic melanoma cell.

Such a cell finds applications as a cell with a fusogenic capacity capable of inducing the formation of syncytia, as described below.

Alternatively, a cell of the invention may be a non-tumoral cell of the human or non-human animal immune system, preferably a non-tumoral human or non-human animal dendritic cell, said cell expressing at least one mutant protein in accordance with the invention at its surface. Such a cell finds applications as an agent capable of inducing the production of cell fusion inhibitor, for example by active immunisation, as described below.

Medical Applications (Pro-Fusion):

A mutant protein of the invention, and/or a nucleic acid, DNA or RNA, of the invention, and/or a vector of the invention, and/or a cell of the invention may be used in the treatment and/or prevention and/or mitigation of a disease or a condition which involves the presence and/or proliferation of cells which are pathological and/or not favourable to the health of the organism, more particularly in the treatment and/or prevention and/or mitigation of a disease or a condition which involves an insufficiency of cellular fusogenicity, preferably in the treatment and/or prevention and/or mitigation of a disease or a neoplasic condition, such as a tumour, a metastatic tumour, advantageously a metastatic melanoma.

Such diseases or conditions may be treated and/or prevented and/or mitigated by reduction or removal of these pathological and/or non-favourable cells.

A mutant protein of the invention expressed at the surface of such cells will induce fusion of these cells, and consequently the formation of syncytia, leading to the destruction (or at least to a reduction in number) of these cells.

A mutant protein of the invention, and/or a nucleic acid, DNA or RNA, of the invention, and/or a vector of the invention, and/or a cell of the invention, may be used in the treatment and/or prevention and/or mitigation of a disease or a condition which involves a deficiency in placental development.

Such diseases or conditions may be treated and/or prevented and/or mitigated by induction or stimulation of placental cell fusion.

The present application thus also relates to a pharmaceutical composition or a drug which comprises at least one mutant protein of the invention and/or at least one nucleic acid, DNA, RNA, of the invention, and/or at least one vector of the invention and/or a cell of the invention.

Such a pharmaceutical composition or such a drug may in particular be intended for the treatment and/or prevention and/or mitigation of a disease or a condition which involves the presence and/or proliferation of cells which are pathological and/or not favourable to the health of the organism, as indicated above (as an example, tumour, metastatic tumour, metastatic melanoma), or to the treatment and/or prevention and/or mitigation of a disease or a condition which involves an insufficiency of cellular fusogenicity (as an example, deficiency of placental development).

Such a pharmaceutical composition or such a drug may further comprise at least one pharmaceutically and/or physiologically acceptable vehicle.

A mutant protein of the invention (or a nucleic acid, DNA, RNA, or an expression vector of the invention), may be employed to be expressed by a human cell or a non-human animal cell, preferably to be expressed at the surface of such a cell.

This cell may be a pathological cell, preferably a tumour cell, more preferably a metastatic cell, more preferably a metastatic melanoma cell, or it may be a non-tumoral cell, for example a healthy cell.

More particularly, pathological cells which have been removed from a human patient or a sick non-human animal subject, may be treated ex vivo (or in vitro) by contact with at least one mutant protein of the invention and/or at least one nucleic acid, DNA or RNA, of the invention and/or at least one expression vector of the invention so as to cause them to express a mutant protein of the invention.

Alternatively or complementarily, non-pathological cells which are however localized close to pathological cells of the patient or subject may be removed to undergo that treatment.

The cells thus treated ex vivo (or in vitro) may then be intended to be re-administered to said patient or subject.

Such cells are useful for the treatment and/or prevention and/or mitigation of the pathology with which said patient or subject is affected, for example a tumour, a metastatic tumour, a metastatic melanoma.

Alternatively, this cell may be a placental cell, more particularly a placental cell suffering from an insufficiency of fusogenicity. Once treated by expression of a mutant protein of the invention at its surface, such a cell may be intended for the treatment and/or prevention and/or mitigation of a deficiency of placental development.

The present application is thus more particularly relative to a mutant protein in accordance with the invention, a nucleic acid, DNA or RNA, in accordance with the invention, a vector in accordance with the invention, a cell in accordance with the invention, for use in the treatment and/or prevention and/or mitigation of a disease or a neoplasic condition, preferably a tumour, more preferably a metastatic tumour, highly preferably a metastatic melanoma.

The present application is also more particularly relative to a mutant protein in accordance with the invention, a nucleic acid, DNA or RNA, in accordance with the invention, a vector in accordance with the invention, a cell in accordance with the invention, for use in the treatment and/or prevention and/or mitigation of a deficiency of placental development.

Fusion Inhibitors in Accordance with the Invention:

The present application also relates to products which have the capacity to reduce or block cell fusion. These products are inhibitors of one or more mutant proteins of the invention.

Such inhibitors may be used in the treatment and/or prevention and/or mitigation of a disease or a condition which involves an excess of cellular fusogenicity, preferably in the treatment and/or prevention and/or mitigation of an enveloped virus infection (such as an HIV, influenza, parainfluenza or rhabdovirus infection), an allergy, an auto-immune disease or a graft rejection.

Preferably, an inhibitor in accordance with the invention is:

- an antibody directed against a mutant protein in accordance with the invention, or a Fab or F(ab')2 fragment of such an antibody; or
- a nucleic acid aptamer or a peptide aptamer which binds specifically to at least one mutant protein in accordance with the invention, or to a nucleic acid, DNA, RNA, in accordance with the invention; or
- a recombinant immune system cell, preferably a recombinant dendritic cell, which expresses at least one mutant protein in accordance with the invention at its surface; or
- an antisense nucleic acid of a nucleic acid in accordance with the invention; or
- a small interfering RNA, siRNA, comprising a double strand RNA containing 19 to 22 nucleotides, capable of binding (hybridizing) to a nucleic acid in accordance with the invention.

The present application thus also pertains to a non-tumoral cell of the human or non-human animal immune system, preferably a human or non-human animal dendritic cell, said cell expressing at least one mutant protein in accordance with the invention at its surface, as well as to the use of this cell in the treatment and/or prevention and/or mitigation of a disease or a condition which involves an excess of cellular fusogenicity, preferably in the treatment and/or prevention and/or mitigation of an enveloped virus infection (such as a HIV, influenza, parainfluenza or rhabdovirus infection), an allergy, an auto-immune disease or a graft rejection.

The present application also relates to an antibody directed against a mutant protein in accordance with the invention, or against several mutant protein or proteins of the invention. Preferably, this antibody is a specific antibody for said mutant proteins of the invention. Advantageously, this antibody is a monoclonal antibody. An inhibitor of the invention may be a conserved fragment of such an antibody, such as a Fab or F(ab')2 fragment.

Such an antibody or antibody fragment may be intended to block or inhibit a cell fusion mechanism, for example by administration of said antibody or antibody fragment to a patient or subject in need thereof.

Alternatively or complementarily, a mutant protein of the invention may itself be intended to be administered to said patient or subject so as to induce active immunisation against this protein, i.e. so as to induce the production by said patient or subject of anti-mutant protein antibody. If necessary or desired, one or more vaccine adjuvants may be administered jointly with or at a different time to said mutant protein or proteins.

The present application thus also pertains to a therapeutic and/or preventative and/or mitigating vaccine, which comprises at least one mutant protein of the invention as an immunogenic agent, and advantageously at least one immunisation adjuvant. Such a vaccine may be intended for the treatment and/or prevention and/or mitigation of a disease or a condition which involves an excess of cellular fusogenicity, preferably in the treatment and/or prevention and/or mitigation of an enveloped virus infection (such as a HIV, influenza, parainfluenza or rhabdovirus infection), an allergy, an auto-immune disease or a graft rejection.

The present application also relates to:

- a nucleic acid aptamer or a peptide aptamer which binds specifically to at least one mutant protein of the invention, or to a nucleic acid, DNA, RNA, of the invention;
- a recombinant immune system cell, preferably a recombinant dendritic cell, which expresses at least one mutant protein of the invention at its surface;
- an antisense nucleic acid of a nucleic acid of the invention;
- a small interfering RNA, siRNA, comprising a double strand RNA containing 19 to 22 nucleotides, capable of binding (hybridizing) to a nucleic acid of the invention, and advantageously of blocking or inhibiting transcription of said nucleic acid.

Such products are also inhibitors of the invention. They may thus be intended for the treatment and/or prevention and/or mitigation of a disease or a condition which involves an excess of cellular fusogenicity, as indicated above. More particularly, they are intended for the treatment and/or prevention and/or mitigation of a disease or a condition which involves at least one gene for expression or hyper-expression of the F protein.

The present application thus also pertains to a pharmaceutical composition or a drug which comprises at least one inhibitor of the invention.

Such a pharmaceutical composition or such a drug may in particular be intended for the treatment and/or prevention and/or mitigation of a disease or a condition which involves an excess of cellular fusogenicity, as indicated above.

Such a pharmaceutical composition or such a drug may further comprise at least one pharmaceutically and/or physiologically acceptable vehicle.

The present application more particularly pertains to an inhibitor in accordance with the invention, for use in the treatment and/or prevention and/or mitigation of a disease or a condition involving an excess of cellular fusogenicity, said disease or condition being an enveloped virus infection (preferably a HIV and/or influenza and/or parainfluenza and/or rhabdovirus infection), an allergy, an auto-immune disease or a graft rejection.

The present application more particularly pertains to a mutant protein in accordance with the invention, for use as an immunogenic agent in the treatment and/or prevention and/or mitigation of a disease or a condition involving an excess of cellular fusogenicity, said disease or condition being an enveloped virus infection (preferably a HIV and/or influenza and/or parainfluenza and/or rhabdovirus infection), an allergy, an auto-immune disease or a graft rejection.

The present application more particularly pertains to a vaccine or vaccine composition, more particularly a vaccine or vaccine composition intended for the treatment and/or prevention and/or mitigation of a disease or a condition involving an excess of cellular fusogenicity, said disease or condition being an enveloped virus infection (preferably a HIV and/or influenza and/or parainfluenza and/or rhabdovirus infection), an allergy, an auto-immune disease or a graft rejection. Such a vaccine or vaccine composition comprises at least the mutant protein in accordance with the invention, and optionally at least one physiologically acceptable adjuvant.

Diagnostic and Prognostic Applications:

The present application also relates to a method, more particularly an in vitro method, for the diagnosis or prognosis of a disease or a condition involving:

- insufficient formation of syncytia, such as a tumour, a metastatic tumour, a metastatic melanoma or a deficiency in placental development; or in contrast
- an excessive formation of syncytia, such as an enveloped virus infection (preferably a HIV and/or influenza and/or parainfluenza and/or rhabdovirus infection), an allergy, an auto-immune disease or a graft rejection.

The diagnostic or prognostic method of the invention comprises detection of at least one mutant protein in accordance with the invention or at least one nucleic acid in accordance with the invention, for example in a biological sample such as a biological sample which has been taken from the patient or subject undergoing said diagnosis or prognosis.

This detection may, for example, be carried out by sequencing proteins or nucleic acids contained in said sample.

This detection may, for example, be carried out by detection of said at least one mutant protein of the invention using an antibody, a peptide aptamer or an oligonucleotide aptamer binding to said at least one mutant protein, more particularly using an antibody, peptide aptamer or oligonucleotide aptamer of the invention.

This detection may, for example, be carried out by detection of said at least one nucleic acid of the invention using a nucleic acid, a peptide aptamer or an oligonucleotide aptamer binding to said at least one nucleic acid, more particularly using a nucleic acid complementary to a nucleic acid of the invention, a peptide aptamer or an oligonucleotide aptamer of the invention.

The present application also relates to said antibody, peptide aptamer, oligonucleotide aptamer, complementary nucleic acid, for their use in a method for the diagnosis or prognosis of insufficient formation, or in contrast excessive formation, of syncytia.

Biotechnological Applications (Screening):

The present application also relates to a method, more particularly an in vitro method, for screening a compound capable of reducing or blocking the formation of syncytia. The method of the invention comprises bringing a candidate compound into contact with cells expressing at least one mutant protein of the invention, so as to determine whether said candidate compound reduces or blocks fusion of said cells (for example by comparing the degree of fusion achieved in the presence of said candidate compound with that achieved in its absence).

Such compounds are candidate active principles for the treatment and/or prevention and/or mitigation of a disease or a condition involving an excess of cellular fusogenicity, such as enveloped virus infections, allergies, auto-immune diseases or graft rejections.

Biotechnological Applications (Myeloma, Hybridoma):

The present application also relates to a tumour cell, more particularly myeloma, comprising at least one mutant protein in accordance with the invention, preferably comprising at least one such mutant protein on its surface, and/or comprising at least one nucleic acid in accordance with the invention, and/or comprising at least one vector in accordance with the invention, more particularly an expression vector in accordance with the invention.

Such a tumour cell, more particularly such a myeloma, may in particular be used in the production of a hybridoma (by fusion of this tumour cell with a B lymphocyte), more particularly in the production of an antibody-producing hybridoma.

The present application also relates to a hybridoma, more particularly an antibody-producing hybridoma, which comprises at least one mutant protein in accordance with the invention, and/or at least one nucleic acid in accordance with the invention, and/or at least one vector in accordance with the invention. Such a hybridoma may in particular be produced by bringing at least one B lymphocyte into contact with at least one tumour cell, more particularly myeloma, comprising at least one mutant protein in accordance with the invention, preferably comprising at least one such mutant protein on its surface, and/or comprising at least one nucleic acid in accordance with the invention, and/or comprising at least one vector in accordance with the invention. Such a tumour cell has an intrinsic fusogenic capacity: it is thus capable of fusing with said at least one B lymphocyte, without employing polyethylene glycol (PEG) or electroporation means or any other means which, in the prior art, are conventionally used to induce fusion of a tumour cell to a B lymphocyte with the aim of producing a hybridoma.

Biotechnological Applications (Stem or Progenitor Cells):

The present application also relates to a stem or progenitor cell comprising at least one mutant protein in accordance with the invention, preferably comprising at least one such mutant protein on its surface, and/or comprising at least one nucleic acid in accordance with the invention, and/or comprising at least one vector in accordance with the invention, more particularly an expression vector in accordance with the invention.

Such a stem or progenitor cell has an intrinsic fusogenic capacity: it is thus capable of forming syncytia by fusion.

If this stem or progenitor cell also has a capacity for differentiation into muscle cell, it is then capable of forming a muscle fibre (by cell fusion and formation of a syncytium).

The present application thus also pertains to such a stem or progenitor cell for its use in the production, for example in the in vitro production, of a muscle fibre.

This production may, for example, be carried out by placing a plurality of said stem or progenitor cells in mutual contact on or in a culture medium allowing the proliferation of stem cells, or if appropriate progenitor cells, such that the fusogenic capacity of said stem or progenitor cells can be exercised, thereby inducing the formation of a syncytium, more particularly a muscle fibre. Examples of culture media allowing the proliferation of stem cells, or if appropriate progenitor cells, and which are also appropriate to the expression of their possible capacity to differentiate into muscle cell, more particular muscle fibre, are known to the skilled person; an example is MCDB medium.

Examples of cell markers that allow the differentiation of a stem or progenitor cell into muscle cell, more particularly into muscle fibre, to be observed are also known to the skilled person, for example CD56.

In the present application, the term "comprising", which is synonymous with "including" or "containing", is an open term that does not exclude the presence of one or more additional elements, ingredients or steps which will not be explicitly indicated, while the term "consisting" or "constituted" is a closed term which excludes the presence of any other additional element, step or ingredient which is not explicitly disclosed. The term "essentially consisting of" or "essentially constituted by" is a partially open term which does not exclude the presence done or more additional elements, ingredients or steps, provided that those additional elements, ingredients or steps do not materially affect the properties at the basis of the invention.

As a consequence, the term "comprising" (or "comprise(s)") includes the terms "consisting of", "constituted by" as well as terms "essentially consisting of" and "essentially constituted by".

The contents of the documents and the bibliographic references which are cited in the present application are incorporated by reference.

The following examples are given purely by way of illustration and do not in any way limit the invention.

EXAMPLES

Example 1

Construction of Mutants and Measurement of their Fusogenicity

Methods and Apparatus:

Cells and Viruses

The cell line LLC-MK2 (Macaca mulatta kidney cell line) is available from the American Type Culture Collection (ATCC) with accession number CCL-7.

The cell line A549 (human pulmonary carcinoma cell line) is available from the ATCC with accession number CCL-185.

The recombinant line HuH7-Tat (human hepatoma cell line) is available by transduction of cells of the HuH-7 line by HIV-1 Tat.

The HuH-7 line is available from the Japanese Collection of Research Bioresources, reference number JCRB0403.

Transduction of the HuH-7 line by HIV-Tat was carried out with the aid of the retroviral vector LXSN-tat transducing the Tat plasmid.

The cells LLC-MK2, A549 and HuH7-Tat were cultivated in EMEM (Eagle's Minimum Essential Medium) or DMEM (Dulbecco/Vogt Modified Eagles' Essential Minimal Medium) with 5% foetal calf serum.

The PIV-5 WR strain was obtained from the ATCC (number ATCC VR-288), and was cultivated on LLC-MK2 cells as described by Terrier et al, 2008.

Extraction of RNA, RT-PCR and Cloning

Viral RNA was extracted from the supernatant obtained from infection of LLC-MK2 cells by PIV-5, with the aid of the Absolutely RNA® Microprep Kit (Stratagene, USA), following the instructions provided by the supplier. The reverse transcription was carried out with the aid of pd(N)6 random hexamers (Amersham Biosciences, GB) and a reverse transcriptase (Reverse Transcriptase; RT) of the avian myeloblastosis virus, AMV (AMV-RT reverse transcriptase available from Promega).

Amplification of the complete sequence for PIV-5 F was carried out with a primer pair designed from the nucleotide sequence for PIV-5 available from the databases (GenBank accession number AB021962).

The primer pair employed was as follows:

```
Sense primer (SEQ ID NO: 1):
5' TTGCGGCCGCATGGGTACTATAA 3'

Antisense primer (SEQ ID NO: 2):
5' CCGCTCGAGTTATGATAAACAAAATTCTCC 3'
```

Amplification was carried out in accordance with the following protocol: 95° C. for 2 min, then 39 cycles (95° C./30 s, 55° C./1 min, 72° C./3 min) and a final elongation of 10 min at 72° C.

The complementary DNA of PIV-5 F was cloned into the expression plasmid pcDNA3.1(+) at the NotI and XhoI sites at the multiple cloning site (see FIG. 4).

The PCR products and the plasmids were respectively purified using the Nueleospin® ExtractII and Nucleospin® plasmid kits (Macherey Nagel, Germany), following the instructions provided by the supplier.

The sequencing series in this study was executed by MWG Biotech (Ebersberg, Germany).

Directed Mutagenesis Using the Polymerase Chain Reaction (PCR)

The mutant proteins of the F protein of PIV-5 were produced by directed mutation in the plasmid pcDNA3.1 encoding the PIV-5 F fusion protein. The mutation(s) were generated by PCR using complementary primers, following the protocol provided by the supplier (QuickChange® Site-Directed Mutagenesis System available from Stratagene). The list of primers used is given in Table 2 below. Assembly of the plasmids was checked by sequencing.

TABLE 2 list of primers

| Mutation | Region targeted in PIV-5 | | Sequences for primers used for mutagenesis by PCR | SEQ ID NO: |
|---|---|---|---|---|
| L22P | F2 | Sense | 5' GGAGCAGGCAGCCTTGATC<u>C</u>AGC<u>T</u>GCTCTCATGCAAATCGG 3' | 3 |
| | | Antisense | 5' CCGATTTGCATGAGAGC<u>A</u>GCT<u>G</u>GATCAAGGCTGCCTGCTCC 3' | 4 |
| K132E | HR1 | — | Pre-existing mutation | — |
| V290A | HR3 | — | Pre-existing mutation | — |
| I49A | F2 | Sense | 5' GGCCTCATCAGCATTC**<u>GC</u>**TGTTGTGAAGTTAATGCC 3' | 5 |
| | | Antisense | 5' GGCATTAACTTCACAACA**<u>GC</u>**GAATGCTGATGAGGCC 3' | 6 |
| V402A | between HR3 and HR2 | Sense | 5' CAGCCAAGTTCATCTCCTG**<u>C</u>**AACTGTCATTGACATGTAC 3' | 7 |
| | | Antisense | 5' GTACATGTCAATGACAGTT**<u>G</u>**CAGGAGAGTGAACTTGGCTG 3' | 8 |
| S443P | upstream of HR2 | Sense | 5' GCTTGAATCATCTCAGATCTTG**<u>T</u>**CCATTGATCCGTTGGATATATCCC 3' | 9 |
| | | Antisense | 5' GGGATATATCCAACGGATCAATGG**<u>A</u>**CAAGATCTGAGATGATTCAAGC 3' | 10 |

TABLE 2-continued list of primers

| Mutation | Region targeted in PIV-5 | | Sequences for primers used for mutagenesis by PCR | SEQ ID NO: |
|---|---|---|---|---|
| L447p | upstream of HR2 | Sense | 5' CTCAGATCTTGTCCATTGATCCG**CC**GGATATATCCCAGAATCTAGCTGCG 3' | 11 |
| | | Antisense | 5' CGCAGCTAGATTCTGGGATATATCC**GG**CGGATCAATGGACAAGATCTGAG 3' | 12 |
| I449P | upstream of HR2 | Sense | 5' CTTGTCCATTGATCCGTTGGAT**CC**ATCCCAGAATCTAGCTGCGGTG 3' | 13 |
| | | Antisense | 5' CACCGCAGCTAGATTCGTT**GG**ATTTCTCCCAGAATCTAGCTGCGG 3' | 14 |
| I449F | upstream of HR2 | Sense | 5' GCCCATTGATCCGTTGGAT**T**T**C**TCCCAGAATCTAGCTGCGG 3' | 15 |
| | | Antisense | 5' CCGCAGCTAGATTCTGGGA**G**A**A**ATCCAACGGATCAATGGGC 3' | 16 |
| T147V | HR1 | Sense | 5' CTCAAAAATGCAATCCAAAAA**GT**AAATGCAGCAGTTGCAGATG 3' | 17 |
| | | Antisense | 5' CATCTGCAACTGCTGCATTT**AC**TTTTTGGATTGCATTTTTGAG 3' | 18 |
| T158V | HR1 | Sense | 5' GCAGATGTGGTCCAGGCC**GT**ACAATCACTAGGAACGGC 3' | 19 |
| | | Antisense | 5' GCCGTTCCTAGTGATTGT**AC**GGCCTGGACCACATCTGC 3' | 20 |
| A463V | HR2 | Sense | 5' GTGAATAAGAGTCTAAGTGATG**T**ACTACAACACTTAGCACAAAGTG 3' | 21 |
| | | Antisense | 5' CACTTTGTGCTAAGTGTTGTAGT**A**CATCACTTAGACTCTTATTCAC 3' | 22 |

The mutation 443P is theoretically pre-existent in the F protein of the WR isolate. However, in the sample of this isolate that the inventors received from the ATCC, this mutation was in fact not present. It thus had to be introduced by the inventors.

Transfection of Cells

The cells were transfected by the plasmids with the aid of the reagent ExGen500 (Fermentas), following the instructions provided by the supplier. One to three micrograms of plasmidic DNA was added to the cells (at 70 to 80% confluence) for 48 h. The efficiency of transfection was estimated using a plasmid encoding the green fluorescence protein, GFP.

Immunofluorescence by Confocal Microscopy

The transfected cells were fixed using paraformaldehyde (1% v/v) in phosphate buffer saline, PBS, then washed twice. The cell mats were incubated in the presence of a monoclonal antibody directed against the PIV-5 F protein, in this case the monoclonal antibody F1a described by Randall et al, 1987, diluted to 1/10 in PBS for 3 h. The monoclonal antibody F1a had been obtained by immunisation of mice against an isolate of PIV-5 (in this case the LN isolate), preparation of hybridomas and selection of specific anti-F antibodies.

The cell mats were then washed and incubated with a secondary anti-mouse IgG-Alexa Fluor® 633 antibody (Invitrogen) diluted to 1/200 in PBS for 30 minutes. After rinsing, the cells were incubated for 10 minutes with Dapi (4',6'-diamidino-2-phenyl indole) at 1/1000 mixed or not mixed with wheatgerm agglutinin (WGA) coupled to Alexa Fluor® 488 (WGA-Alexa Fluor® available from Invitrogen) at 1/200 in phosphate buffer saline, PBS. The images were acquired using a TCS SP2 confocal microscope (Leica).

Flow Cytometry

Flow cytometry was carried out as described in the literature (Horvat and Lamb 1992). A549 cells were transfected by the plasmids encoding the various Fus and were deposited onto ice. The cell mats were rinsed with phosphate buffer saline, PBS, comprising 1% of sodium azide. A monoclonal anti-F protein of PIV-5 antibody (in this case the monoclonal antibody Fla) was then added to the mat (1/500 PBS phosphate buffer with 1% foetal calf serum), and incubated for 30 minutes at 4° C. The mats were then rinsed and incubated in the presence of a secondary anti-mouse antibody coupled to Alexa Fluor® 488 at 1/1000 (Invitrogen). After rinsing, the cells were gently detached using 500 µL of PBS phosphate buffer, 0.5 mM in EDTA (ethylene-diamine-tetraacetic acid). The cells were transferred into dedicated flow cytometry tubes containing 500 µL of a 1% paraformaldehyde solution. The intensity of fluorescence of 5000 cells was measured using fluorescence-activated cell sorting, FACS, in this case using the FACSVantage™ SE flow from Becton Dickinson.

Semi-Quantitative Fusion Test (Fusion Scores Established as a Function of Syncytium Size and Number of Nuclei)

Mats transfected by the various Fus expression plasmids and observed in immunofluorescence allowed a semi-quantitative analysis to be carried out. This analysis consisted of determining a fusion score for each of the mutants using the following criteria:

fusion or otherwise (simples agglomerates), denoted −/+;

the size of the syncytium, on a scale of 1 to 5;

the number of nuclei, on a scale of 1 to 5.

The score calculated thereby was obtained by adding two marks: the maximum theoretical mark was thus 10 and corresponded to a maximum size of syncytium with a maximum number of nuclei.

Quantitative Fusion Test (Measurement of Luciferase Activity)

In order to quantify cell-cell fusion, "donor" A549 cells (2.5 million cells per well of a E-well plate) were co-transfected with 2 µg of plasmid pcDNA3.1 encoding the various Fus mutant proteins as well as 50 ng of a plasmid expressing luciferase under the dependency of the long terminal repeat, LTR (Lavillette et al, 2007).

The negative control was provided by cells co-transfected with 2 µg of the empty plasmid pcDNA3.1.

Twelve hours post-transfection, the "donor" cells were detached using phosphate buffer (PBS), 0.5 mM in EDTA, and were counted then replaced in fresh 6-well plates ($10^5$ cells/well). "Indicator" HuH7-Tat cells ($4\times10^5$ cells/well) were detached using PBS-EDTA buffer, then rinsed and added to the "donor" cells.

The luciferase activity was measured after 72 h of co-culture using a luciferase activity measuring kit, in this case the Luciferase Assay System (E1500) kit from Promega, following the indications provided by the supplier.

Results:

Mutant proteins constructed and produced by the inventors are shown in Table 3 above.

In this Table 3, the inventors have organized the various mutations as a function of the function attributed to them, namely:

- involvement in the function of autonomy as regards HN: positions 22, 132 and 290 of the F protein of PIV-5;
- involvement in the function of pre-fusion: positions 49, 402, 443, 447 and 449 of the F protein of PIV-5;
- involvement in the function of post-fusion: positions 147, 158 and 463 of the F protein of PIV-5.

FIGS. 5 A, 5B, 5C and 5D illustrate the positions of the mutations of Table 3.

Mutant proteins have thus been constructed, produced and tested by the inventors.

TABLE 3

| list of proteins produced | | | | | | | | | | | | |
|---|---|---|---|---|---|---|---|---|---|---|---|---|
| | Autonomy | | | Pre-fusion | | | | | | Post-fusion | | |
| | L22P | K132E | V290A | I49A | V402A | S443P | L447P | I449P | I449F | T147V | T158V | A463V |
| Fus1 (SEQ ID NO: 47) | | + | + | | | | | | | | | |
| Fus1.1 (SEQ ID NO: 48) | | + | + | + | | | | | | | | |
| Fus 1.2 (SEQ ID NO: 49) | | + | + | | + | | | | | | | |
| Fus2 (SEQ ID NO: 50) | | + | + | | | + | | | | | | |
| Fus3 (SEQ ID NO: 51) | + | + | + | | | | | | | | | |
| Fus3.1 (SEQ ID NO: 52) | + | + | + | | | | | | | + | | |
| Fus3.2 (SEQ ID NO: 53) | + | + | + | | | | | | | + | + | |
| Fus 3.3 (SEQ ID NO: 54) | + | + | + | | | | | | | | + | |
| Fus4 (SEQ ID NO: 55) | + | + | + | + | | | | | | | | |
| Fus5 (SEQ ID NO: 56) | + | + | + | | + | | | | | | | |
| Fus6 (SEQ ID NO: 57) | + | + | + | | | + | | | | | | |
| Fus 6.1 (SEQ ID NO: 58) | + | + | + | | | + | | | | + | | |
| Fus 6.2 (SEQ ID NO: 59) | + | + | + | | | + | | | | | + | |
| Fus 6.3 (SEQ ID NO: 60) | + | + | + | | | + | | | | + | + | |
| Fus7 (SEQ ID NO: 61) | + | + | + | | | | + | | | | | |
| Fus 7.1 (SEQ ID NO: 62) | + | + | + | | | | + | | | + | | |
| Fus 7.2 (SEQ ID NO: 63) | + | + | + | | | | + | | | | + | |
| Fus 7.3 (SEQ ID NO: 64) | + | + | + | | | | + | | | + | + | |
| Fus8 (SEQ ID NO: 65) | + | + | + | | | | | + | | | | |
| Fus9 (SEQ ID NO: 66) | + | + | + | | | | | | + | | | |
| Fus10 (SEQ ID NO: 67) | + | + | + | + | | | | + | | | | |

TABLE 3-continued

| list of proteins produced | | | | | | | | | | | | |
|---|---|---|---|---|---|---|---|---|---|---|---|---|
| | Autonomy | | | Pre-fusion | | | | | | Post-fusion | | |
| | L22P | K132E | V290A | I49A | V402A | S443P | L447P | I449P | I449F | T147V | T158V | A463V |
| Fus 10.4 (SEQ ID NO: 68) | + | + | + | | + | | | + | | + | + | + |
| Fus 10.5 (SEQ ID NO: 69) | + | + | + | + | + | | | + | | + | + | + |
| Fus11 (SEQ ID NO: 70) | + | + | + | | + | | | + | | | | |
| Fus8.1 (SEQ ID NO: 71) | + | + | + | | | | | + | | + | | |
| Fu8.2 (SEQ ID NO: 72) | + | + | + | | | | | + | | | + | |
| Fus8.4 (SEQ ID NO: 73) | + | + | + | | | | | + | | + | + | |
| Fus8.5 (SEQ ID NO: 74) | + | + | + | | | | | + | | + | | + |
| Fus8.6 (SEQ ID NO: 75) | + | + | + | | | | | + | | | + | + |
| Fus8.7 (SEQ ID NO: 76) | + | + | + | | | | | + | | + | + | + |
| Fus10.1 (SEQ ID NO: 77) | + | + | + | + | | | | + | | | + | |
| Fus10.2 (SEQ ID NO: 78) | + | + | + | + | | | | + | | + | + | |
| Fus10.3 (SEQ ID NO: 79) | + | + | + | + | | | | + | | + | + | + |

The F protein sequence for PIV-5 which was used during the construction and production of these mutant proteins was an alternative F protein sequence for the WR isolate. This alternative sequence was identical to the sequence of SEQ ID NO: 31 (Genbank sequence), with the exception of the amino acid in position 443 which was S and not P (alternative sequence "SEQ ID NO: 31 with S at 443").

The sequences for SEQ ID NO: 47 to 79 were thus the sequences which result from replacement within said alternative sequence "SEQ ID NO: 31 with S at 443", of the amino acids indicated for each of these sequences in Table 3 above.

An illustration of the observations made under the microscope during the semi-quantitative fusion tests is presented in FIG. 6A.

The scores obtained at the end of the semi-quantitative fusion tests are presented in FIG. 6B.

The mutant proteins Fus6, Fus 6.1, Fus 6.2 and Fus 6.3 resulted in agglutination of many cells, but not in cell fusion.

The mutant proteins Fus 3.3, Fus 3.1, Fus2, Fus 1.1, Fus 1.2 and Fus 1 produced a zero fusion score.

The mutant proteins Fus 9, Fus7, Fus 3, Fus 5 and Fus 4 produced low fusion scores.

Beyond the fusion score of Fus 4, a series of mutant proteins with a significant fusion score separated out, namely:

- the group of mutant proteins which in common comprise the three mutations for autonomy and the mutation for pre-fusion 449P, such as the mutant proteins Fus8, Fus10, Fus10.4, Fus10.5, Fus11, Fus8.1, Fus8.2, Fus8.4, Fus8.5, Fus8.6, Fus8.7, Fus10.1, Fus10.2, Fus10.3; and
- the group of mutant proteins which in common comprise the three mutations for autonomy, the mutation for pre-fusion 447P and at least one post-fusion mutation (147V or 158V), such as Fus7.1, Fus7.2 or Fus7.3.

FIGS. 7A and 7B present an illustration of the microscope observations and present the fusion scores for a selection of the tested mutant proteins, namely the group of mutant proteins which in common comprise:

- the three mutations for autonomy;
- the mutation for pre-fusion 447P; and
- at least one post-fusion mutation in position 147 and/or 158 to present at this/these positions a hydrophobic amino acid such as V, I or L, for example the post-fusion mutation 147V and/or the post-fusion mutation 158V; such as the mutant proteins Fus7.1, Fus7.2 and Fus7.3.

Example 2

Substitution of Natural Cleavage Site by the Site for an Enzyme Specifically Expressed by Metastatic Tumour Tissue The mutant proteins of the invention, and more particularly those described in Example 1 above, had previously been modified by substitution of the natural cleavage site of the native F protein, for example to replace it with a tissue-specific cleavage site.

By way of illustration, the natural cleavage site of the F protein of PIV-5 has been substituted by the site for an enzyme specifically expressed by metastatic tumour tissue, namely matrix metallo-protease 9 (MMP-9).

The natural cleavage site of the F protein of PIV-5 is:

```
RRRRR.              (SEQ ID NO: 23)
```

An example of a fragment of the F protein sequence comprising the natural cleavage site of the F protein of PIV-5 is:

```
IGENLETIRNQLIPTRRRRRFAGVVIGL.     (SEQ ID NO: 24)
```

The consensus sequence for a MMP-9 cleavage site is:

```
PXXHyS/T            (SEQ ID NO: 27)
```

where X=any amino acid, and
where Hy=any hydrophobic amino acid (i.e. any amino acid selected from F, M, V, L, I).

An example of a MMP-9 cleavage site is:

```
PRRIT.              (SEQ ID NO: 28)
```

An example of a fragment of a mutant F protein sequence of the invention comprising a MMP-9 cleavage site is:

```
IGENLETIRNQLIPTPRRITFAGVVIGL.     (SEQ ID NO: 29)
```

Methods and Apparatus:

The mutant proteins of the F protein of PIV-5 were produced as described in Example 1 above.

Replacement of the natural cleavage site by the selected cleavage site, in this case the MMP-9 cleavage site of SEQ ID NO: 28, was carried out as follows:

Replacement of the cleavage site was carried out by 3 successive directed mutageneses in the plasmid pcDNA3.1 encoding the fusion protein F PIV-5. The mutations were generated by PCR using complementary primers, following the protocol indicated by the supplier (QuickChange® Site-Directed Mutagenesis System available from Stratagene). Assembly of the plasmids was checked by sequencing.

1st MUTATION R98P
SENSE
(SEQ ID NO: 80)
5' CCAGTTGATTCCAACTCCGAGGAGACGCCGGTTTGC 3'

ANTISENSE
(SEQ ID NO: 81)
5' GCAAACCGGCGTCTCCTCGGAGTTGGAATCAACTGG 3'

2nd MUTATION R101I
SENSE
(SEQ ID NO: 82)
5' GATTCCAACTCCGAGGAGAATCCGGTTTGCAGGAGTGGTG 3'

-continued

ANTISENSE
(SEQ ID NO: 83)
5' CACCACTCCTGCAAACCGGATTCTCCTCGGAGTTGGAATC 3'

3rd MUTATIQN R102T
SENSE
(SEQ ID NO: 84)
5' GATTCCAACTCCGAGGAGAATCACGTTTGCAGGAGTGGTGATTGG 3'

ANTISENSE
(SEQ ID NO: 85)
5' CCAATCACCACTCCTGCAAACGTGATTCTCCTCGGAGTTGGAATC 3'

Transfection of Cells

The cells were transfected by the plasmids with the aid of the reagent ExGen500 (Fermentas), following the instructions provided by the supplier. One to three micrograms of plasmidie DNA were added to the cells (70 to 80% confluence) for 48 h. The efficiency of transfection was estimated with the aid of a plasmid encoding green fluorescence protein, GFP.

Immunofluorescence by Confocal Microscopy

The transfected cells were fixed with the aid of paraformaldehyde (1% v/v) in phosphate buffer saline, PBS, then washed twice. The cell mats were incubated in the presence of a monoclonal antibody directed against the fusion protein NV-5 F, in this case the monoclonal antibody F1a described by Randall et al, 1987, diluted to 1/10 in PBS for 3 h. The monoclonal antibody F1a had been obtained by immunisation of mice against un isolate of PIV-5 (in this case the LN isolate), preparation of hybridomas and selection of specific anti-F antibodies.

The cell mats were then washed and incubated with a secondary anti-mouse IgG-Alexa Fluor® 633 antibody (Invitrogen) diluted to 1/200 in PBS for 30 minutes. After rinsing, the cells were incubated for 10 minutes with Dapi (4', 6'-diamidino-2-phenyl indole) at 1/1000 mixed or not mixed with wheatgerm agglutinin, WGA, coupled to Alexa Fluor® 488 (WGA-Alexa Fluor® available from Invitrogen) at 1/200 in phosphate buffer, PBS. The images were acquired using a TCS SP2 confocal microscope (Leica).

BIBLIOGRAPHICAL REFERENCES

Baker et al, 1999, Mol Cell. 3(3):309-19.

Chatziandreou et al, 2004, Journal of General Virology 85: 3007-3016.

Horvat and Lamb 1992, J. Virol. 66(4): 2443-2455.

Ito et al 1997, J Viral. 71(12): 9855-9858.

Ito et al, 2000, J Gen Viral. 81(Pt 3):719-727.

Gardner and Dutch 2007, J. Viral. 81(15):8303-14.

Gardner et al, 2007, Biochemistry 46(17):5094-5105.

Lavillette D. et al, 2007, J. Virol. 81(16): 8752-8765

Paterson et al, 2000, Virology 270(1):17-30.

Randall et al, 1987, J. Gen. Viral. 68(Pt 11): 2769-2780

Russell et al, 2003, J. Cell Biol. 163(2):363-74.

Terrier et al, 2008, Journal of Clinical Virology, 2008, 43(1): 86-92.

West et al, 2005, J Viral. 79(3):1543-1551.

The invention claimed is:

1. A mutant protein, the amino acid sequence of which comprises a sequence which is derivable from that of the wild-type F protein of a PIV-5 virus:

by replacement of the amino acid which, in the sequence of said wild-type PIV-5 F protein, is in position 22; and of the amino acid which, in the sequence of said wild-type PIV-5 F protein, is in position 132; and of the amino acid which, in the sequence of said wild-type PIV-5 F protein, is in position 290; and of the amino acid which, in the sequence of said wild-type PIV-5 F protein, is in position 447;

and by replacement:

of the amino acid which, in the sequence of said wild-type PIV-5 F protein, is in position 147, by a hydrophobic amino acid selected from V, I, L, preferably V; and/or of the amino acid which, in the sequence of said wild-type PIV-5 F protein, is in position 158 by a hydrophobic amino acid selected from V, I, L, preferably V;

wherein said positions are computed by alignment with respect to the reference wild-type PIV-5 F protein of SEQ ID NO: 31.

2. The mutant protein of claim 1, characterized in that the sequence of said wild-type PIV-5 F protein comprises or consists of:

i. the sequence of SEQ ID NO: 31, or ii. the sequence, which is identical to the sequence of SEQ ID NO: 31 except for the amino acid at position 443, which is S instead of P, or iii. a sequence, which is of the same amino acid length as said sequence of i. or ii. and which is more than 95% identical to said sequence of i. or ii., but which does not simultaneously comprise the amino acids P, E, A, P at positions 22, 132, 290 and 447, respectively, and the amino acid V, I or L at position(s) 147 and/or 158, wherein said positions are computed by alignment with respect to the reference wild-type PIV-5 F protein of SEQ ID NO: 31.

3. The mutant protein of claim 1, wherein said wild-type PIV-5 F protein comprises or consists of i. the sequence of SEQ ID NO: 31, or ii. the sequence, which is identical to the sequence of SEQ ID NO: 31 except for the amino acid at position 443, which is S instead of P iii. the sequence of SEQ ID NO: 35.

4. The mutant protein of claim 1, wherein said hydrophobic amino acid, which replaces the amino acid, which, in the sequence of said wild-type PIV-5 F protein, is in position 158, is V.

5. The mutant protein of claim 1, wherein said hydrophobic amino acid, which replaces the amino acid, which, in the sequence of said wild-type PIV-5 F protein, is in position 147, is V.

6. The mutant protein of claim 1, the amino acid sequence of which comprises a sequence, which is derivable from said wild-type PIV 5 F protein by the amino acid replacements indicated in claim 1 and, which is further derivable from that of said wild-type PIV 5 F protein by substitution of the native cleavage site of said F protein by another enzymatic cleavage site, and/or by insertion into said F protein of an enzymatic cleavage site other than the native cleavage site of this F protein, and/or by deletion of a C-terminal portion of said F protein, said C-terminal portion extending in the N-terminal direction from the last amino acid at the C-terminal end of the protein, but without extending beyond the HR2 domain of said F protein.

7. The mutant protein of claim 6, wherein said cleavage site other than the native cleavage site is a tissue-specific cleavage site.

8. An isolated cell, which comprises at least one mutant protein of claim 1.

9. An isolated immune system cell, which expresses at its surface at least one mutant protein of claim 1.

10. An isolated cell of the human or non-human animal immune system, wherein said cell expresses at its surface at least one mutant protein of claim 1.

11. A composition comprising at least one mutant protein of claim 1.

12. An isolated tumor cell, comprising at least one mutant protein of claim 1.

13. A hybridoma, which comprises at least one mutant protein of claim 1.

14. An isolated stem or progenitor cell, having a capacity for differentiation into muscle cell, which comprises at least one mutant protein of claim 1, said cell not being a human embryo cell.

15. The mutant protein of claim 1, wherein the sequence of said wild-type PIV-5 F protein consists of i. the sequence of SEQ ID NO: 31, or ii. the sequence, which is identical to the sequence of SEQ ID NO: 31 except for the amino acid in position 443, which is S instead of P, or iii. a sequence, which is:

which is identical in size to that of SEQ ID NO: 31, or of a size larger than that of SEQ ID NO: 31 by a maximum of 7 C-terminal amino acids, or of a size smaller than that of SEQ ID NO: 31 by a maximum of 7 C-terminal amino acids, and which is more than 95% identical to said sequence of i. or ii., this identity percentage being calculated over the length of said sequence of i. or ii. respectively, but which does not simultaneously comprise the amino acids P, E, A and P at positions 22, 132, 290 and 447, respectively, and the amino acid V, I or L at position(s) 147 and/or 158, wherein said positions are computed by alignment with respect to the reference wild-type PIV-5 F protein of SEQ ID NO: 31.

16. The mutant protein of any one of claims 2, 3 and 15, the amino acid sequence of which comprises a sequence, which is derivable from said wild-type PIV-5 F protein by the amino acid replacements indicated in claim 1 and, which is further derivable from said wild-type PIV-5 F protein sequence by at least one mutation selected from the group consisting of the replacement of the amino acid in position 49 by the amino acid A, the replacement of the amino acid in position 402 by the amino acid A, the replacement of the amino acid in position 443 by the amino acid P, and the replacement of the amino acid in position 449 by the amino acid P, and/or by the replacement of the amino acid in position 463 by a hydrophobic amino acid, wherein said positions are computed by alignment with respect to the reference wild-type PIV-5 F protein of SEQ ID NO: 31.

17. The isolated immune system cell of claim 9, which is a dendritic cell.

18. The isolated cell of claim 10, which is a dendritic cell.

19. The isolated tumor cell of claim 12, which is a myeloma cell.

20. An isolated tumor cell which expresses said at least one mutant protein of claim 1 at its surface.

21. A composition comprising at least one isolated immune system cell of claim 9.

22. The mutant protein of claim 1, which is a fusogenic protein.

23. A composition comprising at least one isolated cell of claim 10.

* * * * *